US012594307B2

(12) United States Patent
Hasty et al.

(10) Patent No.: US 12,594,307 B2
(45) Date of Patent: Apr. 7, 2026

(54) COMPOSITIONS AND METHODS OF USING INDUCIBLE SIGNALING FOR TUNABLE DYNAMICS IN MICROBIAL COMMUNITIES

(71) Applicant: The Regents of the University of California, Oakland, CA (US)

(72) Inventors: Jeff Hasty, San Diego, CA (US); Arianna Miano, La Jolla, CA (US); Michael Julius Liao, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 758 days.

(21) Appl. No.: 17/784,547

(22) PCT Filed: Dec. 11, 2020

(86) PCT No.: PCT/US2020/064525
§ 371 (c)(1),
(2) Date: Jun. 10, 2022

(87) PCT Pub. No.: WO2021/119436
PCT Pub. Date: Jun. 17, 2021

(65) Prior Publication Data
US 2023/0044530 A1 Feb. 9, 2023

Related U.S. Application Data

(60) Provisional application No. 62/947,932, filed on Dec. 13, 2019.

(51) Int. Cl.
| | |
|---|---|
| *A61K 35/74* | (2015.01) |
| *A61K 35/00* | (2006.01) |
| *C07K 14/195* | (2006.01) |
| *C12N 9/00* | (2006.01) |
| *C12N 9/10* | (2006.01) |
| *C12N 15/63* | (2006.01) |
| *C12N 15/70* | (2006.01) |

(52) U.S. Cl.
CPC .............. *A61K 35/74* (2013.01); *A61K 35/00* (2013.01); *C07K 14/195* (2013.01); *C12N 9/1029* (2013.01); *C12N 9/93* (2013.01); *C12N 15/635* (2013.01); *C12N 15/70* (2013.01); *C12Y 203/01184* (2013.01)

(58) Field of Classification Search
CPC ...... A61K 35/74; A61K 35/00; C07K 14/195; C12N 9/1029; C12N 9/93; C12N 15/635; C12N 15/70; C12Y 203/01184
See application file for complete search history.

(56) References Cited

U.S. PATENT DOCUMENTS

| | | |
|---|---|---|
| 5,196,318 A | 3/1993 | Baldwin |
| 8,293,478 B2 | 10/2012 | Souno et al. |
| 9,593,339 B1 | 3/2017 | Bermudes |
| 11,174,486 B2 | 11/2021 | Hasty et al. |
| 11,613,758 B2 | 3/2023 | Hasty et al. |
| 11,896,626 B2 | 2/2024 | Hasty et al. |
| 2004/0180829 A1 | 9/2004 | Bassler et al. |
| 2008/0286310 A1 | 11/2008 | Zhu et al. |
| 2010/0104607 A1 | 4/2010 | Engelberg-Kulka et al. |
| 2011/0217282 A1 | 9/2011 | Inouye et al. |
| 2012/0069914 A1 | 3/2012 | Shental et al. |
| 2013/0023035 A1 | 1/2013 | Bielinski et al. |
| 2013/0052164 A1 | 2/2013 | Chang et al. |
| 2013/0209405 A1 | 8/2013 | Curtiss |
| 2015/0209393 A1 | 7/2015 | Chang et al. |
| 2017/0037363 A1 | 2/2017 | Whitlock et al. |
| 2017/0044570 A1 | 2/2017 | Weiss et al. |
| 2022/0251579 A1 | 8/2022 | Hasty et al. |
| 2023/0126966 A1 | 4/2023 | Hasty et al. |
| 2024/0350559 A1 | 10/2024 | Hasty et al. |

FOREIGN PATENT DOCUMENTS

| | | |
|---|---|---|
| CN | 201362719 | 12/2009 |
| CN | 103635571 | 3/2014 |
| CN | 104131018 | 11/2014 |

(Continued)

OTHER PUBLICATIONS

Machine Translation of WO-2016013844-A1; Original Document Published Jan. 28, 2016 (Year: 2016).*
Bao et al., Quorum-sensing based small RNA regulation for dynamic and tuneable gene expression. Biotechnol Lett., 2019, vol. 41:1147-1154. (Year: 2019).*
DeLateur NA., Engineering LuxR-type quorum sensing proteins for new functions. PhD., Thesis, MIT, Aug. 16, 2019, pp. 1-115. (Year: 2019).*

(Continued)

*Primary Examiner* — Ganapathirama Raghu

(74) *Attorney, Agent, or Firm* — Fish & Richardson P.C.

(57) ABSTRACT

Provided herein are compositions and methods for modulating induction of quorum sensing in bacterial cells. For example, provided herein is a method of inducing method of inducing quorum sensing, where the method includes: culturing a bacterial strain, wherein the bacterial strain comprises a first nucleic acid sequence encoding a first activator polypeptide, wherein expression of the first activator polypeptide produces a quorum sensing molecule precursor; a second nucleic acid sequence encoding a second activator polypeptide, wherein expression of the second activator polypeptide produces a quorum sensing; a third nucleic acid sequence encoding a third activator polypeptide that is capable of activating the quorum sensing system; a fourth nucleic acid sequence encoding a gene of interest, and contacting the bacterial strain with an inducer molecule; and converting the inducer molecule into a quorum sensing molecule, thereby allowing induction of quorum sensing.

12 Claims, 27 Drawing Sheets

Specification includes a Sequence Listing.

(56) References Cited

FOREIGN PATENT DOCUMENTS

| EP | 2182068 | 5/2010 | | |
| JP | 2008519002 | 6/2008 | | |
| KR | 20160000979 | 1/2016 | | |
| WO | WO 2013/003597 | 1/2013 | | |
| WO | WO 2014/043593 | 3/2014 | | |
| WO | WO 2014/046593 | 3/2014 | | |
| WO | WO 2014/098767 | 6/2014 | | |
| WO | WO-2016013844 A1 * | 1/2016 | ............ | C12N 15/52 |
| WO | WO 2016/164636 | 10/2016 | | |
| WO | WO 2017/203533 | 11/2017 | | |
| WO | WO 2018/213815 | 11/2018 | | |
| WO | WO-2018213815 A2 * | 11/2018 | ........... | C12M 23/16 |
| WO | WO 2019/237083 A1 | 12/2019 | | |

OTHER PUBLICATIONS

Kang et al., Production of bacterial quorum sensing antagonists, caffeoyl- and feruloyl-HSL, by an artificial biosynthetic pathway. J. Microbiol. Biotechnol., 2017, vol. 27(12): 2104-2111. (Year: 2017).*

Jiang et al., "Research progress on the molecular-level regulation mechanism of bacterial quorum sensing," Journal of Natural Sciences of Heilongjiang University, Apr. 25, 2013, 30(2):232-238 (with English Abstract).

Andersen et al., "New unstable Variants of Green Fluorescent Protein for Studies of Transient Gene Expression in Bacteria," Appl. Environ. Microbiol., Jun. 1, 1998, 64(6):2240-2246.

Anderson et al. "Environmentally controlled invasion of cancer cells by engineered bacteria," J Mol Biol, 2005, 355(4):619-627.

Ausländer et al., "Programmable single-cell mammalian biocomputers," Nature, Jul. 2012, 487(7405):123-127.

Baban et al., "Bacteria as vectors for gene therapy of cancer," Bioengineered bugs, Nov. 1, 2010, 1(6):385-394.

Balagadde et al., "Long-term monitoring of bacteria undergoing programmed population control in a microchemostat," Science, Jul. 1, 2005, 309(5731):137-140.

Balagadde, F. K. et al., "A synthetic Escherichia coli predator-prey ecosystem," Molecular systems biology, 2008, 4(187): 8 pages.

Begley et al., "Raise standards for preclinical cancer research," Nature, Mar. 2012, 483(7391):531-533.

Bernardes et al., "Engineering of bacterial strains and their products for cancer therapy," Applied microbiology and biotechnology, Jun. 2013, 97(12):5189-5199.

Bittihn et al., "Suppression of beneficial mutations in dynamic microbial populations," Physical Review Letters, 2017, 118:028102, 5 pages.

Borek et al., "Turing patterning using gene circuits with gas-induced degradation of quorum sensing molecules," PloS one, May 5, 2016, 11(5):e0153679, 13 pages.

Boyer et al., "Characterization of the cvaA and cvi promoters of the Colicin V Export System: Iron-dependent transcription of cvaA is modulated by downstream sequences," Journal of bacteriology, Apr. 1, 1998, 180(7):1662-1672.

Brenner et al., "Engineered bidirectional communication mediates a consensus in a microbial biofilm consortium," Proceedings of the National Academy of Sciences, Oct. 30, 2007, 104(44):17300-17304.

Brenner et al., "Engineering microbial consortia: a new frontier in synthetic biology," Trends in biotechnology, Sep. 1, 2008, 26(9):483-489.

Buchler et al., "Molecular titration and ultrasensitivity in regulatory networks," Journal of molecular biology, Dec. 31, 2008, 384(5):1106-1119.

Burger et al., "Abduction and asylum in the lives of transcription factors," Proceedings of the National Academy of Sciences, Mar. 2, 2010, 107(9):4016-4021.

Cann et al., "Dr William Coley and Tumour Regression: A Place in History or in the Future," Postgraduate medical journal, Dec. 1, 2003, 79(938):672-680.

Cascales et al., "Colicin biology," Microbiology and molecular biology reviews, Mar. 1, 2007, 71(1):158-229.

Chan et al., "'Deadman' and 'Passcode' microbial kill switches for bacterial containment," Nature chemical biology, Feb. 2016, 12(2): 19 Pages.

Chen et al., "Application of a Proapoptotic Peptide to Intratumorally Spreading Cancer Therapy," Cancer research, Feb. 15, 2013, 73(4):1352-1361.

Chen et al., "Emergent genetic oscillations in a synthetic microbial consortium," Science, 2015, 349(6251):986-989.

Chen, "Development and application of co-culture for ethanol production by co-fermentation of glucose and xylose: a systematic review," Journal of industrial microbiology & biotechnology, May 1, 2011, 38(5):581-597.

Cheong et al., "A bacterial protein enhances the release and efficacy of liposomal cancer drugs," Science, Nov. 24, 2006, 314(5803):1308-1311.

Chlebina et al., "Continuous protein production and release via oscillatory suicidal lysis circuits," Dissertation Thesis, Department of Biomedical Engineering, Duke University, Published 2012, 50 pages.

Cho et al., "The human microbiome: at the interface of health and disease," Nature Reviews Genetics, Apr. 2012, 13(4):260-270.

Coley, "The Treatment of Inoperable Sarcoma by Bacterial Toxins (the mixed toxins of the Streptococcus erysipelas and the Bacillus prodigiosus)," Proceedings of the Royal Society of Medicine, Jun. 1910, (Surg_Sect): 48 pages.

Cookson et al., "Queueing up for enzymatic processing: correlated signaling through coupled degradation," Molecular systems biology, 2011, 7(1): 9 pages.

Cummins et al., "Bacteria and tumours: causative agents or opportunistic inhabitants?," Infectious agents and cancer, Dec. 2013, 8(1):1-8.

Dai et al., "Construction of an inducible cell-communication system that amplifies Salmonella gene expression in tumor tissue," Biotechnology and Bioengineering, Jun. 2013, 110(6):1769-1781.

Dang et al., "Combination bacteriolytic therapy for the treatment of experimental tumors," Proceedings of the National Academy of Sciences, Dec. 18, 2001, 98(26):15155-15160.

Danino et al., "A synchronized quorum of genetic clocks," Nature, 2010, 463:326-330.

Danino et al., "Measuring Growth and Gene Expression Dynamics of Tumor-Targeted S. Typhimurium Bacteria," Jo VE (Journal of Visualized Experiments), Jul. 6, 2013, 6(77):e50540, 7 pages.

Danino et al., "Programmable probiotics for detection of cancer in urine," Science translational medicine, May 27, 2015, 7(289): 12 pages.

Danino et al., "In vivo gene expression dynamics of tumor targeted bacteria," ACS synthetic biology, Oct. 19, 2012, 1(10):465-470.

Davila et al., "Efficacy and Toxicity Management of 1 9-28z CAR T Cell Therapy in B Cell Acute Lymphoblastic Leukemia." Science Translational Medicine, Feb. 19, 2014, 6(224): 23 pages.

De Boer et al., "The Tac Promoter: A Functional Hybrid Derived from the TRP and LAC Promoters," Proceedings of the National Academy of Sciences, Jan. 1983, 80(1):21-25.

De Roy et al., "Environmental conditions and community evenness determine the outcome of biological invasion," Nature communications, Jan. 22, 2013, 4(1):1-5.

De Roy et al., "Synthetic microbial ecosystems: an exciting tool to understand and apply microbial communities," Environmental microbiology, Jun. 2014, 16(6):1472-1481.

Dejonghe et al., "Synergistic degradation of linuron by a bacterial consortium and isolation of a single linuron-degrading variovorax strain," Applied and Environmental Microbiology, 2003, 69(3):1532-1541.

Del Vecchio et al., "Modular Cell Biology • Retroactivity and Insulation," Molecular systems biology, 2008, 4(1): 16 pages.

Derman et al., "Phylogenetic analysis identifies many uncharacterized actin-like proteins (Alps) in bacteria: regulated polymerization, dynamic instability and treadmilling in Alp7A," Molecular microbiology, Aug. 2009, 73(4):534-552.

Din et al., "Synchronized cycles of bacterial lysis for in vivo delivery," Nature, Aug. 2016, 536(7614): 12 Pages.

Elowitz et al., "A synthetic oscillatory network of transcriptional regulators," Nature, Jan. 2000, 403(6767):335-338.

(56) References Cited

OTHER PUBLICATIONS

Endy et al., "Foundations for engineering biology," Nature, Nov. 2005, 438(7067):449-453.

Escholarship.org [online], "Communication and Coexistence: Engineering Tools for Synthetic Microbial Ecosystems," Jan. 2016, retrieved on May 4, 2021, retrieved from URL <https://escholarship.org/uc/item/5qs3q001>, 102 pages.

Extended European Search Report in European Appln. No. 16777310, dated Oct. 17, 2018, 13 pages.

Extended European Search Report in European Appln. No. 18801861.8, dated May 3, 2021, 8 pages.

Extended European Search Report in European Appln. No. 19815732.3, dated Jun. 3, 2022, 11 pages.

Faust et al., "Microbial interactions: from networks to models," Nature Reviews Microbiology, 2012, 10:538-550.

Ferry et al., "Microfluidics for Synthetic Biology from Design to Execution.", Methods Enzymol, 2011, 497: 295-372.

Fischbach et al., "Cell-based therapeutics: the next pillar of medicine," Science translational medicine, Apr. 3, 2013, 5(179):179ps7, 7 Pages.

Folcher et al., "Synthetic biology advancing clinical applications," Current opinion in chemical biology, Aug. 1, 2012, 16(3-4):345-354.

Forbes, Engineering the perfect (bacterial) cancer therapy, Nature Reviews Cancer, Nov. 2010, 10(11):785-794.

Foster et al., "Competition, not cooperation, dominates interactions among culturable microbial species," Current biology, 2012, 22(19):1845-1850.

Fredriksson et al., "Decline in ribosomal fidelity contributes to the accumulation and stabilization of the master stress response regulator oS upon carbon starvation," Genes & development, Apr. 2007, 21(7):862-874.

Fulget et al., "Melissa: global control strategy of the artificial ecosystem by using first principles models of the compartments, " Advances in Space Research, 1999, 24(3):397-405.

Gardner et al., "Construction of a genetic toggle switch in *Escherichia coli*," Nature, Jan. 2000, 403(6767):339-342.

Garrett et al., "Cancer and the Microbiota," Science, Apr. 3, 2015, 348(6230):80-86.

Gerdes et al., "The parB (hok/sok) locus of plasmid R1: a general purpose plasmid stabilization system," Bio/Technology, Dec. 1988, 6(12):1402-1405.

Goldbeter et al., An Amplified Sensitivity Arising from Covalent Modification in Biological Systems, Proceedings of the National Academy of Sciences, Nov. 1981, 78(11):6840-6844.

Gravel et al., "Experimental niche evolution alters the strength of the diversity-productivity relationship," Nature, Jan. 2011, 469(7328):89-92.

Griffith et al., "Inducible protein degradation in Bacillus subtilis using heterologous peptide tags and adaptor proteins to target substrates to the protease Clpx'P," Molecular microbiology, Nov. 2008, 70(4):1012-1025.

Großkopf et al., "Synthetic microbial communities," Current opinion in microbiology, Apr. 1, 2014, 18:72-77.

Grunberg et al., "Strategies for protein synthetic biology," Nucleic acids research, May 1, 2010, 38(8):2663-2675.

Hasty et al., "Engineered gene circuits," Nature, Nov. 2002, 420(6912):224-230.

Higashikuni et al., "Advancing therapeutic applications of synthetic gene circuits," Current opinion in biotechnology, Oct. 1, 2017, 47:133-141.

Hohmann et al., "Evaluation of a Phop/Phoq-Deleted, Aroa-Deleted Live Oral *Salmonella typhi* Vaccine Strain in Human Volunteers," Vaccine, Jan. 1, 1996, 14(1):19-24.

Hooshangi et al., "Ultrasensitivity and Noise Propagation in a Synthetic Transcriptional Cascade," Proceedings of the National Academy of Sciences, Mar. 8, 2005, 102(10):3581-3586.

International Preliminary Report on Patentability in International Application No. PCT/US2016/26518, dated Oct. 10, 2017, 7 pages.

International Preliminary Report on Patentability in International Appln. No. PCT/US2018/033555, dated Feb. 25, 2020, 7 pages.

International Preliminary Report on Patentability in International Appln. No. PCT/US2019/036179, dated Dec. 17, 2020 8 Pages.

International Search Report and Written Opinion in International Appln. No. PCT/US2018/033555, dated Aug. 13, 2018, 11 pages.

International Search Report and Written Opinion in International Application No. PCT/US2016/26518, dated Apr. 7, 2016, 9 pages.

International Search Report and Written Opinion in International Appln. PCT/US2019/036179, dated Sep. 23, 2019, 14 Pages.

International Search Report and Written Opinion in International Appln. PCT/US2020/064525, dated Mar. 10, 2021, 18 pages.

International Preliminary Report on Patentability in International Appln. No. PCT/US2020/064525, dated Jun. 23, 2022 7 pages.

Isaacs et al., "Prediction and measurement of an autoregulatory genetic module," PNAS, 2003, 100(13):7714-7719.

Jeong et al., "Anti-Tumoral Effect of the Mitochondrial Target Domain of Noxa Delivered by an Engineered *Salmonella typhimurium*," PloS one, Jan. 8, 2014, 9(1):e80050, 11 pages.

Jiang et al., "Inhibition of Tumor Growth and Metastasis by a Combination of *Escherichia coli*-mediated Cytolytic Therapy and Radiotherapy," Molecular therapy, Mar. 1, 2010, 18(3):635-642.

June, CH et al., "Engineered t Cells for Cancer Therapy," Cancer Immunology, Immunotherapy, Sep. 2014, 63(9):969-975.

Kaur et al., "Bacteriocins as Potential Anticancer Agents," Frontiers in pharmacology, Nov. 10, 2015, 6:272.

Keiler et al., "Role of a Peptide Tagging System in Degradation of Proteins Synthesized from Damaged Messenger RNA," Science, Feb. 16, 1996, 271(5251):990-993.

Kerr et al., "Local dispersal promotes biodiversity in a real-life game of rock-paper-scissors," Nature, Jul. 2002, 418(6894):171-174.

Kirkup et al., "Antibiotic-mediated antagonism leads to a bacterial game of rock-paper-scissors in vivo," Nature, Mar. 1, 2004, 428(6981):412-414.

Klitgord et al., "Environments that induce synthetic microbial ecosystems," PLoS Comput Biol., Nov. 18, 2010, 6(11):e1001002, 17 Pages.

Kolnik et al., "Vacuum-Assisted Cell Loading Enables Shear-Free Mammalian Microfluidic Culture," Lab on a chip, 2012, 12(22):4732-4737.

Landry et al., "Engineering diagnostic and therapeutic gut bacteria. Bugs as Drugs: Therapeutic Microbes for the Prevention and Treatment of Disease," Oct. 20, 2017, 1: 22 pages.

Lee et al., "Next-generation biocontainment systems for engineered organisms," Nature chemical biology, Jun. 2018, 14(6):530-537.

Leone V. et al., "Effects of diurnal variation of gut microbes and high-fat feeding on host circadian clock function and metabolism," Cell host & microbe, May 13, 2015, 17(5):681-689.

Lien et al., "Low-Dose Metronomic Chemotherapy: A Systematic Literature Analysis," European Journal of Cancer, Nov. 1, 2013, 49(16):3387-3395.

Little et al., "Rules of engagement: interspecies interactions that regulate microbial communities," Annu. Rev. Microbiol., 2008, 62: 29 Pages.

Loeffler et al., "*Salmonella typhimurium* engineered to produce CCL21 inhibit tumor growth," Cancer immunology, immunotherapy, May 2009, 58(5):769-775.

Loessner et al., "Remote Control of Tumour-Targeted *Salmonella enterica Serovar typhimuriurn* by the Use of 1-Arabinose as Inducer of Bacterial Gene Expression in vivo," Cellular microbiology, Jun. 2007, 9(6):1529-1537.

Lutz et al., "Independent and tight regulation of transcriptional units in *Escherichia coli* via the lacr/o, the tetr/o and arac/il-i2 regulatory elements," Nucleic acids research, 1997, 25(6):1203-1210.

Lynd et al., "How biotech can transform biofuels," Nature biotechnology, Feb. 2008, 26(2): 169-172.

Mandell et al., "Biocontainment of genetically modified organisms by synthetic protein design," Nature, Feb. 2015, 518(7537): 20 Pages.

Mangwani et al., "Bacterial quorum sensing: functional features and potential applications in biotechnology," Journal of molecular microbiology and biotechnology, 2012, 22(4):215-227.

(56)         References Cited

OTHER PUBLICATIONS

Marguet et al., "Oscillations by minimal bacterial suicide circuits reveal hidden facets of host-circuit physiology," PloS one, Jul. 30, 2010, 5(7): e11909, 11 pages.

Mather et al., "Delay-induced degrade-and-fire oscillations in small genetic circuits," Physical review letters, Feb. 13, 2009, 102(6):068105, 4 pages.

Mather et al., "Streaming instability in growing cell populations," Physical review letters, 2010, 104(20):208101, 4 pages.

McGinness et al., "Engineering controllable protein degradation," Molecular cell, Jun. 9, 2006, 22(5):701-707.

Meighen, E. A., "Genetics of bacterial bioluminescence", Annual review of genetics, 1994, 28(1):117-139.

Merrikh et al., "A DNA Damage Response in *Escherichia coli* Involving the Alternative Sigma Factor, RpoS," Proceedings of the National Academy of Sciences, Jan. 13, 2009, 106(2):611-616.

Miest et al., "New Viruses for Cancer Therapy: Meeting Clinical Needs," Nature reviews microbiology, Jan. 1, 2014, 12(1):23-34.

Mika, et al., "A Two-Component Phosphotransfer Network Involving ArcB, Arc.A, and RssB Coordinates Synthesis and Proteolysis of crS (RpoS) in *E coli*," Genes & development, Nov. 15, 2005, 19(22):2770-2781.

Mondragno-Palomino et al. "Entrainment of a population of synthetic genetic oscillators," Science, 2011, 333(6047):1315-1319.

Moon et al., "Genetic Programs Constructed From Layered Logic Gates in Single Cells," Nature, Nov. 2012, 491(7423):249-253.

Mukherji et al., "MicroRNAs can generate thresholds in target gene expression," Nature genetics, Sep. 2011, 43(9):854-859.

Muller et al., "Cell-cell communication by quorum sensing and dimension-reduction," Journal of mathematical biology, Oct. 2006, 53(4):672-702.

Nandagopal et al., "Synthetic Biology: Integrated Gene Circuits," Science, Sep. 2, 2011, 333(6047): 6 pages.

Newcombe, "Origin of bacterial variant," Nature, Jul. 1949, 164(4160):150-151.

Nguyen et al., Genetically Engineered *Salmonella typhirnurium* as an Imageable Therapeutic Probe for Cancer, Cancer research, Jan. 1, 2010, 70(1):18-23.

O'Shea, CC., "Viruses Seeking and Destroying the Tumor Program," Oncogene, Nov. 2005, 24(52):7640-7655.

Ostrov et al., "Design, synthesis, and testing toward a 57-codon genome," Science, Aug. 19, 2016, 353(6301): 5 Pages.

Parsek et al., "Acyl-homoserine lactone quorum sensing in gram-negative bacteria: a signaling mechanism involved in associations with higher organisms," Proceedings of the National Academy of Sciences, Aug. 1, 2000, 97(16):8789-8793.

Paton et al., "Bioengineered microbes in disease therapy", Trends in molecular medicine, 18, 7, pp. 417-425, 2012.

Pawelek et al., "Tumor-Targeted *Salmonella* as a Novel Anticancer Vector," Cancer research, Oct. 15, 1997, 57(20):4537-4544.

Pedelacq et al., "Engineering and characterization of a superfolder green fluorescent protein," Nature biotechnology, 2006, 2(1)4:79-88.

Peredelchuk et al., "A method for construction of *E. coli* strains with multiple DNA insertions in the chromosome," Gene, Mar. 18, 1997, 187(2):231-238.

Petrof et al., "Stool substitute transplant therapy for the eradication of clostridium difficile infection: repoopulating, the gut," Microbiome, Dec. 2013, 1(1):1-22.

Press, WH In Numerical Recipes: The Art of Scientific Computing 3rd ed. Cambridge Univ. Press), 2007, 1262 pages.

Prindle et al., "A sensing array of radically coupled genetic 'biopixels'," Nature, Jan. 2012, 481(7379):39-44.

Prindle et al., "Genetic Circuits in *Salmonella typhimurium*," ACS synthetic biology, Oct. 19, 2012, 1(10):458-464.

Prindle et al., "Rapid and Tunable Post-Translational Coupling of Genetic Circuits," Nature, Apr. 2014, 508(7496):387-391.

Pruteanu et al., "The cellular level of the recognition factor RssB is rate-limiting for σS proteolysis: implications for RssB regulation and signal transduction in σS turnover in *Escherichia coli*," Molecular microbiology, Sep. 2002, 45(6):1701-1713.

Purcell et al., "Temperature Dependence of ssrA-Tag Mediated Protein Degradation," Journal of biological engineering, Dec. 2012, 6(1):1-3.

Purnick et al., "The second wave of synthetic biology: from modules to systems," Nature reviews Molecular cell biology, Jun. 2009, 10(6):410-422.

Quan et al., "Circular polymerase extension cloning of complex gene libraries and pathways," PloS one, 2009, 4(7):e6441, 6 pages.

Renda et al., "Engineering reduced evolutionary potential for synthetic biology," Molecular BioSystems, 2014, 10: 38 pages.

Riedel et al., "Construction of p16slux, a novel vector for improved bioluminescent labeling of gram-negative bacteria," Applied and environmental microbiology, Nov. 1, 2007, 73(21):7092-7095.

Riglar et al., "Engineering bacteria for diagnostic and therapeutic applications," Nature Reviews Microbiology, Apr. 2018, 16(4): 12 Pages.

Roberts et al., "Intratumoral injection of Clostridium novyi-NT spores induces antitumor responses," Science translational medicine, Aug. 13, 2014, 6(249): 12 pages.

Rosenfeld et al., "Response Delays and the Structure of Transcription Networks," Journal of molecular biology, Jun. 13, 2003, 329(4):645-654.

Rovner et al., "Recoded organisms engineered to depend on synthetic amino acids," Nature, Feb. 2015, 518(7537): 17 Pages.

Ruder et al., "Synthetic Biology Moving into the Clinic," Science, Sep. 2, 2011, 333(6047):1248-1252.

Ryan et al., "Bacterial Delivery of a Novel Cytolysin to Hypoxic Areas of Solid Tumors," Gene Therapy, Mar. 2009, 16(3):329-339.

Sausville et al., "Contributions of human tumor xenografts to anticancer drug development," Cancer research, Apr. 1, 2006, 66(7):3351-3354.

Schaefer et al., "A New Class of Homoserine Lactone Quorum-Sensing Signals," Nature, Jul. 2008, 454(7204):595-599.

Scott et al. "A stabilized microbial ecosystem of self-limiting bacteria using synthetic quorum-regulated lysis," Nat Microbiol, 2017, 2(17083):1-9.

Scott et al., "Quorum sensing communication modules for microbial consortia," ACS synthetic biology, 2016, 5(9):969-977.

Scott, "Communication and Coexistence: Engineering Tools for Synthetic Microbial Ecosystems," Thesis, University of California, San Diego, Jan. 1, 2016, pp. 1-102.

Segall-Shapiro et al., "Engineered promoters enable constant gene expression at any copy number in bacteria," Nature biotechnology, Apr. 2018, 36(4): 11 Pages.

Shaked et al., "Low-Dose Metronomic Combined With Intermittent Bolus-Dose Cydophosphamide is an Effective Long-Term Chemotherapy Treatment Strategy," Cancer research, Aug. 15, 2005, 65(16):7045-7051.

Shong et al., "Towards synthetic microbial consortia for bioprocessing," Current Opinion in Biotechnology, Oct. 1, 2012, 23(5):798-802.

Shou et al., "Synthetic cooperation in engineered yeast populations," Proceedings of the National Academy of Sciences, 2007, 104:1877-1882.

Siuti et al., "Synthetic Circuits Integrating Logic and Memory in Living Cells," Nature biotechnology, May 2013, 31(5):448-452.

Stecher et al., "Flagella and Chemotaxis are Required for Efficient Induction of *Salmonella enterica* Serovar *typhimurium* Colitis in Streptomycin-Pretreated Mice," Infection and immunity, Jul. 2004, 72(7):4138-4150.

Stricker et al., "A Fast, Robust and Tunable Synthetic Gene oscillator," Nature, Nov. 2008, 456(7221):516-519.

Strogatz S., "Nonlinear Dynamics and Chaos: with Applications to Physics, Biology, Chemistry and Engineering" (Perseus Books), 2001, 505 pages.

Swofford et al., "Quorum-sensing *Salmonella* Selectively Trigger Protein Expression within Tumors," Proceedings of the National Academy of Sciences, Mar. 17, 2015, 112(11):3457-3462.

Tanouchi et al., "Engineering microbial systems to explore ecological and evolutionary dynamics," Current opinion in biotechnology, Oct. 1, 2012, 23(5):791-797.

(56)　　　　References Cited

OTHER PUBLICATIONS

Teixeira et al., "Synthetic biology-inspired therapies for metabolic diseases," Current Opinion in Biotechnology, Oct. 1, 2017, 47:59-66.

Thaiss et al., "Chronobiomics: The biological clock as a new principle in host-microbial interactions," PLoS pathogens, Oct. 8, 2015, 11(10):e1005113, 5 pages.

Thakur et al., "Modelling Vemurafenib Resistance in Melanoma Reveals a Strategy to Forestall Drug Resistance", Nature, 494, pp. 251-255, 2013.

Tigges et al., "A Tunable Synthetic Mammalian Oscillator," Nature, Jan. 2009, 457(7227):309-312.

Unger et al., "Monolithic Microfabricated Valves and Pumps by Multilayer Soft Lithography," Science, Apr. 7, 2000, 288(5463):113-116.

Volfson et al., "Biomechanical ordering of dense cell populations," Proceedings of the National Academy of Sciences, 2008, 105(40):15346-15351.

Wang et al., "Programming cells by multiplex genome engineering and accelerated evolution," Nature, Aug. 2009, 460(7257):894-898.

Waters et al., "Quorum Sensing: Cell-to-Cell Communication in Bacteria," Annual review of cell and developmental biology, Nov. 10, 2005, 21(1): 32 pages.

Weber et al., "Emerging Biomedical Applications of Synthetic Biology," Nature Reviews Genetics, Jan. 2012, 13(1):21-35.

Wintermute et al., "Emergent cooperation in microbial metabolism," Molecular systems biology, 2010, 6(1): 7 Pages.

Wood et al., "Enhanced Plasmid Stability Through Post-Segregational Killing of Plasmid-Free cells," Biotechnology techniques, Jan. 1990, 4(1):39-44.

Xie et al., "Multi-input RNAi-based Logic Circuit for Identification of Specific Cancer Cells," Science, Sep. 2, 2011, 333(6047): 7 pages.

Xuan et al., "Microbial Dysbiosis is Associated with Human Breast Cancer," PloS one, Jan. 8, 2014, 9(1):e83744, 7 pages.

You et al., "Programmed population control by cell-cell communication and regulated killing," Nature, Apr. 2004, 428(6985): 4 Pages.

Young et al., "Lytic Action of Cloned Phi x174 Gene e," Journal of virology, Dec. 1982, 44(3):993-1002.

Zambrano et al., "Microbial competition: *Escherichia coli* mutants that take over stationary phase cultures," Science, Mar. 19, 1993, 259(5102):1757-1760.

Zemke et al., "Microbiology: Social suicide for a good cause," Current Biology, 2016, 26(2):R80-R82.

Zhou et al., "Distributing a metabolic pathway among a microbial consortium enhances production of natural products," Nature biotechnology, Apr. 2015, 33(4): 9 Pages.

Zhang et al., "Advances on Quorum Sensing AI22 Signal Molecular," China Biotechnology, Sep. 25, 2005, 25(9):14-18 (with English Abstract).

Zhang et al., "Research progress and application of synthetic biology," All Journals, Apr. 25, 2013, 2 pages (English Abstract only).

Forbes et al., "Sparse initial entrapment of systemically injected *Salmonella typhimurium* leads to heterogeneous accumulation within tumors," Cancer Research, Sep. 1, 2003, 63(17):5188-5193.

Freilich et al., "Competitive and cooperative metabolic interactions in bacterial communities," Nature Communications, Sep. 2011, 2(1):589.

Kang et al., "Production of bacterial quorum sensing antagonists, caffeoyl- and feruloyl-HSL, by an artificial biosynthetic pathway," Journal of Microbiology and Biotechnology, Dec. 28, 2017, 27(12):2104-2111.

Miano et al., "Inducible cell-to-cell signaling for tunable dynamics in microbial communities," Nature Communications, Mar. 4, 2020, 11(1):1193.

Miller et al., "Quorum sensing in bacteria," Annual Reviews in Microbiology, Oct. 2001, 55(1):165-199.

Ryoji et al., "Construction of the artificial gene circuit in a cell," Bionics, 2013, 91(6):327-332 (with English translation).

Scott, "Communication and Coexistence: Engineering Tools for Synthetic Microbial Ecosystems," University of California, San Diego, 2016, pp. 1-102.

Zhou, "Bacteria synchronized for drug delivery," Nature, Aug. 2016, 536(7614):33-34.

European Search Report and Written Opinion in European Appln. No. 21189319.3, dated Sep. 13, 2022, 10 pages.

* cited by examiner

Growth          Induction          QS activation          Termination

COMPOSITIONS AND METHODS OF USING INDUCIBLE SIGNALING FOR TUNABLE DYNAMICS IN MICROBIAL COMMUNITIES

CROSS-REFERENCE TO RELATED APPLICATIONS

This application is a National Stage Application under 35 U.S.C. § 371 and claims the benefit of International Application No. PCT/US2020/064525, filed Dec. 11, 2020, which claims priority to U.S. Provisional Patent Application No. 62/947,932, filed Dec. 13, 2019. The contents of which are incorporated herein by reference in its entirety.

FEDERALLY SPONSORED RESEARCH

This invention was made with government support under MCB1616997 awarded by National Science Foundation. The government has certain rights in the invention.

SEQUENCE LISTING

This application contains a Sequence Listing that has been submitted electronically as an ASCII text file named SequenceListing.txt. The ASCII text file, created on Jun. 7, 2022, is 25.7 kilobytes in size. The material in the ASCII text file is hereby incorporated by reference in its entirety.

TECHNICAL FIELD

The present disclosure relates to compositions and methods for modulating induction of quorum sensing in bacterial cells.

BACKGROUND

Synthetic biology has the potential to revolutionize both healthcare and industry, with applications ranging from therapeutics and drug delivery, to bioproduction and bioremediation. These emerging applications have uncovered the need to engineer spatially extended complex multi-cellular populations, requiring new tools that can bridge the gap between single cell, population, and community level engineering. To achieve this, significant research efforts have been focused on engineering and characterizing a variety of cell-to-cell communication systems, with a particular focus on bacterial quorum sensing.

SUMMARY

This document provides compositions and methods for modulating induction of quorum sensing in bacterial cells. For example, provided herein are methods of inducing quorum sensing in a bacterial strain including nucleic acid sequences encoding activator polypeptides, bacterial strains including the nucleic acid sequences encoding the activator polypeptides, and methods of treating a patient using the bacterial strains described herein. The present disclosure is based on the discovery that an inducible quorum sensing system (iQS) enables a wide range of wide range of new functionality for synthetic circuits that rely on cell-to-cell communication systems for population and community level dynamics. In particular, inducibility broadly expands the functionality of quorum sensing based circuits by enabling switching between states of circuit quiescence, quorum-dependent circuit activation and population wide constitutive expression. This document describes the potential of this tool by coupling it to lysis gene, creating the inducible synchronized lysis circuit (iSLC). This circuit enables spatial and temporal modulation of inducer-dependent cargo release for single or multi-strain communities. In particular, this document demonstrates the ability to temporally and spatially control transitions between inactivated population growth, quorum enabled cyclic cargo release and global population death (kill switch). This precise control of circuit activation, the ability for timed strain elimination and the non-toxic nature of p-coumaric acid make this system particularly attractive for potential therapeutic applications in vivo. This document also describes the orthogonality of the iQS system to demonstrate precise control of multi-strain dynamics which has potential to become a key tool for engineering synthetic bacterial communities. The modularity and simplicity of the iQS genetic parts make it straightforward for coupling to any gene of choice, enabling precise spatial and temporal control over population level gene expression.

In one aspect, this disclosure features methods of inducing quorum sensing, the method including: culturing a bacterial strain, where the bacterial strain includes: a first nucleic acid sequence encoding a first activator polypeptide, where expression of the first activator polypeptide results in production of a quorum sensing molecule precursor, where the first nucleic acid sequence is operably linked to a promoter; a second nucleic acid sequence encoding a second activator polypeptide, where expression of the second activator polypeptide results in production of a quorum sensing molecule, where the second nucleic acid sequence is operably linked to a first activatable promoter; a third nucleic acid sequence encoding a third activator polypeptide, where expression of the third activator polypeptide results in activation of the quorum sensing system, where the third nucleic acid sequence is operably linked to a second activatable promoter; and a fourth nucleic acid sequence encoding a gene of interest, where the fourth nucleic acid sequence is operably linked to a third activatable promoter; and contacting the bacterial strain with an inducer molecule; and converting the inducer molecule into a quorum sensing molecule, thereby allowing induction of quorum sensing.

In some embodiments, the quorum sensing system includes a Lux-like quorum sensing system selected from the group consisting of: a rpa system from *Rhodopseudomonas palustris*; a lux system from *Vibrio fischeri*; a las system from *Pseduomonas aeruginosa*; a rhl system from *Pseduomonas aeruginosa*; a tra system from *Agrobacterium tumefaciens*; a rpa system from *Rhodopseudomonas palustris*; an ahy system from *Aeromonas hydrophilia*; a sma system from *Serratia marcescens*; cer system from *Rhodobacter sphaeroides*; and an exp system from *Sinorhizobium meliloti*. In some embodiments, the quorum sensing system includes all or part of an rpa quorum sensing system, where the rpa sensing system is from *Rhodopseudomonas palustris*.

In some embodiments, the second activator polypeptide includes a luxI homolog selected from the group consisting of: RpaI, RhlI, BjaI, AubI, CerI, LasI, BraI, SinI, LuxI, and EsaI; and where the third activator polypeptide includes a luxR homolog selected from the group consisting of: RpaR, AubR, BjaR, LasR, RhlR, LuxR and TraR.

In some embodiments, (i) the first activatable promoter operably linked to the second nucleic acid is a promoter including one or more lux box-like sequences; (ii) the second activatable promoter operably linked to the third nucleic acid is a promoter including one or more lux box-like sequences; and/or (iii) the third activatable promoter operably linked to the fourth nucleic acid is a promoter including one or more lux box-like sequences.

In some embodiments, the first activator polypeptide includes a p-coumaric acid-CoA ligase, where the p-coumaric acid-CoA ligase is encoded by the 4CL2nt gene from the plant *Nicotiana tabacum*.

In some embodiments, the quorum sensing molecule precursor is p-Coumaroyl-CoA.

In some embodiments, the second activator polypeptide is a 4-coumaroyl-homoserine lactone synthase (RpaI) synthase, where the RpaI synthase is encoded by the RpaI gene from the plant *Rhodopseudomonas palustris*.

In some embodiments, the quorum sensing molecule is p-Coumaroyl-HSL.

In some embodiments, the third activator polypeptide includes a signaling molecule, where the signaling molecule interacts with the quorum sensing molecule.

In some embodiments, the signaling molecule is a HTH-type quorum sensing-dependent transcriptional regulator (RpaR), where the RpaR signaling molecule is encoded by the RpaR gene from the plant *Rhodopseudomonas palustris*.

In some embodiments, the interaction of RpaR and the quorum sensing molecule p-Coumaroyl-HSL results in transcriptional regulation of the fourth nucleic acid sequence.

In some embodiments, the inducer molecule is p-coumaric acid.

In some embodiments, the gene of interest encodes a bacteriophage lytic protein capable of forming a lesion in a host cell's membrane.

In some embodiments, the method further includes one or more additional bacterial strains.

In another aspect, this disclosure features bacterial strains produced by any of the methods described herein.

In another aspect, this disclosure features sets of nucleic acids including any of the nucleic acid sequences described herein.

In another aspect, this disclosure features compositions including any of the bacterial strains that include any of the nucleic acids described herein, any two or more of the bacterial strains described herein, or any of the sets of nucleic acid sequences that include any of the nucleic acid sequences described herein.

In another aspect, this disclosure features a method of treating a disease in a subject, the method including: administering to a subject in need therapeutically effective amounts of any of the bacterial strains described herein or any of the compositions described herein, to thereby treat the disease in the subject. In some embodiments, the disease is cancer.

Unless otherwise defined, all technical and scientific terms used herein have the same meaning as commonly understood by one of ordinary skill in the art to which this disclosure pertains. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the disclosure will be apparent from the following detailed description, and from the claims.

DETAILED DESCRIPTION

Figure 1A:
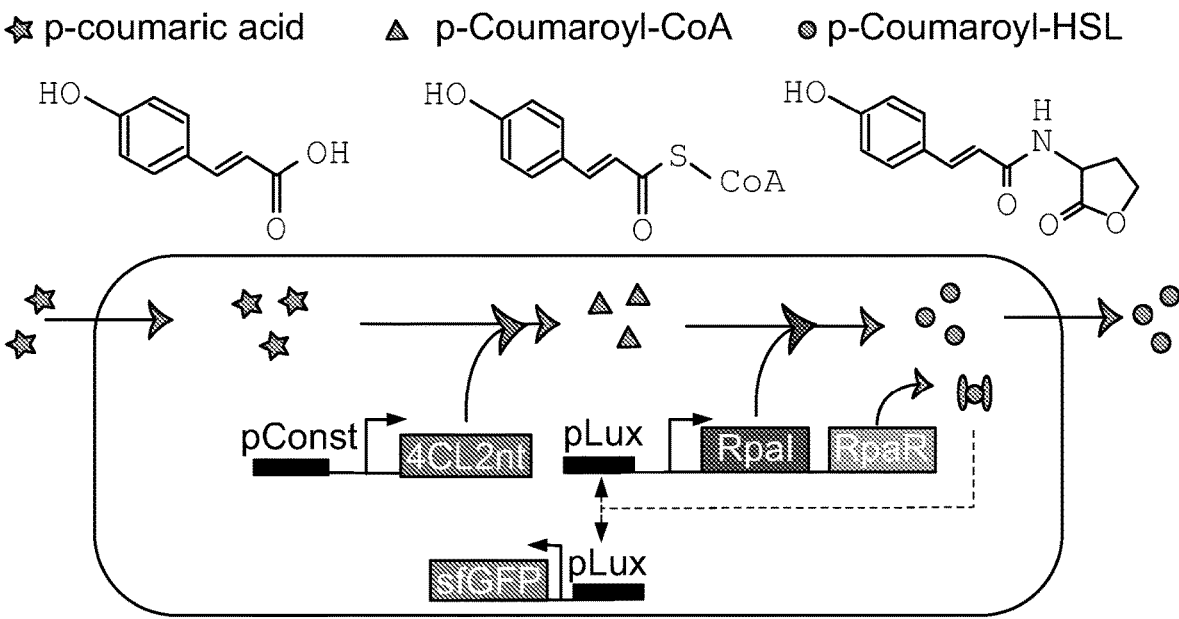
FIG. 1A shows the design and characterization of the p-coumaric acid mediated iQS strain. The chemical structures of the molecules involved in the synthesis of the QS molecule are shown at the top.

This document provides compositions and method for inducing quorum sensing in a bacterial stain including culturing a bacterial strain, wherein the bacterial strain comprises: a first nucleic acid sequence encoding a first activator polypeptide, wherein expression of the first activator polypeptide results in production of a quorum sensing molecule precursor, wherein the first nucleic acid sequence is operably linked to a promoter; a second nucleic acid sequence encoding a second activator polypeptide, wherein expression of the second activator polypeptide results in production of a quorum sensing molecule, wherein the second nucleic acid sequence is operably linked to a first activatable promoter; a third nucleic acid sequence encoding a third activator polypeptide that is capable of activating the quorum sensing system, wherein the third nucleic acid sequence is operably linked to a second activatable promoter; and a fourth nucleic acid sequence encoding a gene of interest, wherein the fourth nucleic acid sequence is operably linked to a third activatable promoter; and contacting the bacterial strain with an inducer molecule; and converting the inducer molecule into a quorum sensing molecule, thereby allowing induction of quorum sensing. As used herein, "quorum sensing" can refer to the ability to detect and respond to cell population density by gene regulation.

Also provided herein are any of the isolated nucleic acids encoding any of the activator polypeptides, reporter polypeptides and genes of interest. Also provided herein are the bacterial strains including any of the nucleic acid sequences described herein.

Also provided herein are methods for treating a subject having a disease by administering to the subject a therapeutically effective amount of any of the bacterial strains described herein or any of the pharmaceutical compositions described herein. Additional non-limiting aspects of the bacterial strains, pharmaceutical compositions, kits, and methods are described herein and can be used in any combination without limitation.

This document provides the combination of two pillars of population control: inducibility and cell-to-cell communication. To design this inducible quorum sensing system (iQS), native components of the photosynthetic bacterium *Rhodopseudomonas palustris* were used, which relies on a plant derived organic compound for the production of its signaling molecule. This inducer, p-coumaric acid, is a ubiquitous molecule present in most fruits and vegetables and has proven to be safe for both bacteria and human cells at relevant concentrations.

The iQS can be coupled with any gene of interest to enable tunable population density-dependent gene expression. This principle was demonstrated by coupling the iQS system to the production of a fluorescent reporter protein in order to characterize the inducible circuit dynamics. Next, as a proof of concept, the iQS was coupled to a lysis gene, creating a tunable platform for cargo release. In direct comparison to non-inducible quorum sensing system, the iQS significantly expands the range of population dynamics, allowing for temporal and spatial control of cargo release and population death. Finally, the orthogonality properties of the iQS system demonstrate the ability to scale up inducibility from the population to the community level. In fact, it has been shown that the quorum sensing molecule produced by the bacterium *R. palustris* is orthogonal to the majority of well-characterized quorum sensing systems (Lux, Las, Tra, Rhl, Cin), providing a communication channel that can propagate information with minimal signal interference. By co-culturing a two strain community, the ability to control population composition and dynamics was demonstrated by varying inducer concentrations. Overall, the iQS system combines many desirable characteristics into a single genetic circuit: inducibility, tunability, population-level coordination, inducer safety, and orthogonality.

The broad potential of the iQS platform enables a wide range of new functionality for synthetic circuits that rely on cell-to-cell communication systems for population-level coordination. In particular, inducibility broadly expanded the functionality of quorum sensing based circuits by enabling switching between states of circuit quiescence, quorum-dependent circuit activation and population wide constitutive expression. In some embodiments, inducible synchronized lysis circuit (iSLC) enables spatial and temporal modulation of inducer-dependent cargo release for single or multi-strain communities. In particular, iSLC demonstrates the ability to temporally and spatially control transitions between inactivated population growth, quorum enabled cyclic cargo release and global population death (kill switch). This precise control of circuit activation, the ability for timed strain elimination and the non-toxic nature of p-coumaric acid make this system particularly at-tractive for potential therapeutic applications in vivo. Additionally, the iQS system demonstrates precise control of multi-strain dynamics which has potential to become a key tool for engineering synthetic bacterial communities. The main challenge will be the functional expression of the p-coumaric acid-CoA ligase enzyme (4CL2nt) due to its heterologous plant origins.

The modularity and simplicity of the iQS described herein make it straightforward for coupling to any gene of choice, enabling precise spatial and temporal control over population level gene expression. Overall, this work includes multiple technologies from circuit design into microbiological organization, from molecular regulatory mechanisms (synthetic promoters), to single cell protein expression (enzyme catalysis), multi-cellular population coordination (cell-to-cell communication) and multi-species interaction (orthogonal quorum sensing).

The term "a" and "an" refers to one or more (i.e., at least one) of the grammatical object of the article. By way of example, "a cell" encompasses one or more cells.

As used herein, the terms "about" and "approximately," when used to modify an amount specified in a numeric value or range, indicate that the numeric value as well as reasonable deviations from the value known to the skilled person in the art, for example ∓20%, +10%, or +5%, are within the intended meaning of the recited value.

Unless otherwise specified, a "nucleotide sequence encoding a protein" can include all nucleotide sequences that are degenerate versions of each other and thus encode the same amino acid sequence.

The term "exogenous" can refer to any material introduced from or originating from outside a cell, a tissue or an organism that is not produced by or does not originate from the same cell, tissue, or organism in which it is being introduced.

The term "transduced", "transfected", or "transformed" can refer to a process by which exogenous nucleic acid is introduced or transferred into a cell (e.g., a bacterial cell).

The term "subject" can include any mammal. In some embodiments, the subject is cat, a dog, a goat, a human, a non-human primate, a rodent (e.g., a mouse or a rat), a pig, or a sheep. In some embodiments, the subject has or is at risk of developing a CNS disorder or disease. In some embodiments, the subject has previously been identified or diagnosed as having a CNS disorder or disease.

The term "nucleic acid" can refer to a deoxyribonucleic acid (DNA) or ribonucleic acid (RNA), or a combination thereof, in either a single- or double-stranded form. Unless specifically limited, the term encompasses nucleic acids containing known analogues of natural nucleotides that have similar binding properties as the reference nucleotides. Unless otherwise indicated, a particular nucleic acid sequence also implicitly encompasses complementary sequences as well as the sequence explicitly indicated. In some embodiments of any of the isolated nucleic acids described herein, the isolated nucleic acid is DNA. In some embodiments of any of the isolated nucleic acids described herein, the isolated nucleic acid is RNA.

Modifications can be introduced into a nucleotide sequence by standard techniques known in the art, such as site-directed mutagenesis and polymerase chain reaction (PCR)-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., arginine, lysine and histidine), acidic side chains (e.g., aspartic acid and glutamic acid), uncharged polar side chains (e.g., asparagine, cysteine, glutamine, glycine, serine, threonine, tyrosine, and tryptophan), nonpolar side chains (e.g., alanine, isoleucine, leucine, methionine, phenylalanine, proline, and valine), beta-branched side chains (e.g., isoleucine, threonine, and valine), and aromatic side chains (e.g., histidine, phenylalanine, tryptophan, and tyrosine), and aromatic side chains (e.g., histidine, phenylalanine, tryptophan, and tyrosine).

The term "treating" can refer to a reduction in the number, frequency, severity, or duration of one or more (e.g., two, three, four, five, or six) symptoms of a disease or disorder in a subject (e.g., any of the subjects described herein), and/or results in a decrease in the development and/or worsening of one or more symptoms of a disease or disorder in a subject.

The term "administer" can refer to a method of delivering agents, compounds, or compositions to the desired site of biological action. These methods include, but are not limited to, topical delivery, parenteral delivery, intravenous delivery, intradermal delivery, intramuscular delivery, colonic delivery, rectal delivery, or intraperitoneal delivery. In one embodiment, the compositions described herein are administered intravenously.

The term "promoter" can refer to a DNA sequence recognized by enzymes/proteins in a cell required to initiate the transcription of an operably linked coding sequence (e.g., a nucleic acid encoding an activator polypeptide. A promoter typically refers, to e.g. a nucleotide sequence to which an RNA polymerase and/or any associated factor binds and at which transcription is initiated. The promoter can be constitutive, inducible, or tissue-specific.

The terms "identical" or percent "identity," in the context of two or more polypeptide sequences, can refer to two or more sequences or subsequences that are the same or have a specified percentage of amino acid residues, e.g., at least 60%, at least 65%, at least 70%, at least 75%, at least 80%, at least 85%, at least 90%, or at least 95% or greater, that are identical over a specified region when compared and aligned for maximum correspondence over a comparison window or designated region, as measured using a sequence compari-son algorithm or by manual alignment and visual inspection.

For sequence comparison of polypeptides, typically one amino acid sequence acts as a reference sequence, to which a candidate sequence is compared. Alignment can be per-formed using various methods available to one of skill in the art, e.g., visual alignment or using publicly available soft-ware using known algorithms to achieve maximal align-ment. Such programs include the BLAST programs, ALIGN, ALIGN-2 (Genentech, South San Francisco, Calif.) or Megalign (DNASTAR). The parameters employed for an alignment to achieve maximal alignment can be determined by one of skill in the art. For sequence comparison of polypeptide sequences for purposes of this application, the BLASTP algorithm standard protein BLAST for aligning two proteins sequence with the default parameters is used.

Quorum Sensing System

In one aspect, this disclosure features an inducible quo-rum sensing system (iQS) that enables population control of one or more bacterial strains via inducibility and cell-to-cell communication. In some embodiments, the methods include an inducible quorum sensing system that includes: culturing a bacterial strain, wherein the bacterial strain includes: a first nucleic acid sequence encoding a first activator polypeptide that is capable of activating a quorum sensing system, wherein the first nucleic acid sequence is operably linked to a promoter; a second nucleic acid sequence encoding a second activator polypeptide that is capable of activating the quorum sensing system, wherein the second nucleic acid sequence is operably linked to an activatable promoter; a third nucleic acid sequence encoding a third activator poly-peptide, wherein expression of the third activator polypep-tide results in activation of the quorum sensing system, wherein the third nucleic acid sequence is operably linked to the activatable promoter; and a fourth nucleic acid sequence encoding a gene of interest, wherein the fourth nucleic acid sequence is operably linked to a second activatable pro-moter; contacting the bacterial strain with an inducer mol-ecule; and converting the inducer molecule into a quorum sensing molecule, thereby allowing induction of quorum sensing.

In some embodiments, the methods include an inducible quorum sensing system that includes: culturing a bacterial strain, wherein the bacterial strain includes: a first nucleic acid sequence encoding a first activator polypeptide that is capable of activating a quorum sensing system, wherein the first nucleic acid sequence is operably linked to a promoter; a second nucleic acid sequence encoding a second activator polypeptide that is capable of activating the quorum sensing system, wherein the second nucleic acid sequence is oper-ably linked to an activatable promoter; and a third nucleic acid sequence encoding a third activator polypeptide that is capable of activating the quorum sensing system, wherein the third nucleic acid sequence is operably linked to an activatable promoter; contacting the bacterial strain with an inducer molecule; and converting the inducer molecule into a quorum sensing molecule, thereby allowing induction of quorum sensing.

In some embodiments, the quorum sensing system is a Lux-like quorum sensing system selected from the group consisting of: a lux system from *Vibrio fischeri*; a las system from *Pseduomonas aeruginosa*; a rhl system from *Pseduomonas aeruginosa*; a tra system from *Agrobacterium*

*tumefaciens*; a rpa system from *Rhodopseudomonas palus-tris*; an ahy system from *Aeromonas hydrophilia*; a sma system from *Serratia marcescens*; cer system from *Rhodo-bacter sphaeroides*; and an exp system from *Sinorhizobium meliloti*. In such cases, the method includes a second acti-vator polypeptide and a third activator polypeptide from a Lux-like quorum sensing system.

In some embodiments, the quorum sensing system is based, at least in part, on an acyl-HSL-type quorum sensing system. In some embodiments, an acyl-HSL-type quorum sensing includes luxI- and luxR-type genes.

In some embodiments, a first activator polypeptide includes a p-coumaric acid-CoA ligase, where the p-cou-maric acid-CoA ligase is encoded by the 4CL2nt gene from the plant *Nicotiana tabacum*. In such cases, an inducer molecule can be a p-coumaric acid molecule. In some embodiments, the inducible quorum sensing system includes a LuxI homolog. In some embodiments, a second activator polypeptide includes a LuxI homolog. LuxI proteins are QS signal synthases that can catalyze amide bond formation between an acyl group on an appropriate side chain donor (most often acyl-acyl carrier protein) and S-adenosylmethio-nine (SAM) resulting in the final acyl-HSL product. Non-limiting examples of LuxI homologs include: RpaI, RhlI, BjaI, AubI, CerI, LasI, BraI, SinI, LuxI, and EsaI. In some embodiments, the inducible quorum sensing system includes a RpaI synthase polypeptide. In some embodiments, the second activator polypeptide is a 4-coumaroyl-homoserine lactone synthase (RpaI) synthase, wherein the RpaI synthase is encoded by the RpaI gene from the plant *Rho-dopseudomonas palustris*.

In some embodiments, the inducible quorum sensing system includes LuxR homologs. In some embodiments, a third activator polypeptide includes a LuxR homolog. LuxR homologs are homodimeric transcription factors, with each monomer consisting of two domains: an N-terminal acyl-HSL binding domain and a C-terminal DNA-binding domain that contains a helix-turn-helix motif. Non-limiting examples of LuxR homologs include: RpaR, AubR, BjaR, LasR, RhlR, LuxR and TraR. In some embodiments, the inducible quorum sensing system includes a RpaR polypep-tide. In some embodiments, a third activator polypeptide comprises a signaling molecule, where the signaling mol-ecule is a LuxR homolog (e.g., a RpaR polypeptide).

In some embodiments, a third activator polypeptide is a signaling molecule, where the signaling molecule interacts with the quorum sensing molecule. In some embodiments, a signaling molecule is a HTH-type quorum sensing-depen-dent transcriptional regulator (RpaR), wherein the RpaR signaling molecule is encoded by the RpaR gene from the plant *Rhodopseudomonas palustris*.

In some embodiments, the inducible quorum sensing system includes a promoter operably linked to a gene of interest where the promoter can be controlled by a LuxR homolog. In some embodiments, a second activator poly-peptide and/or a third activator polypeptide are operably linked to promoters that can be controlled by a LuxR homolog. In some cases, promoters controlled by LuxR homologs can include specific inverted repeat DNA sequences. The inverted DNA repeat elements are known as lux box-like sequences. For example, the lux box is a 20-bp palindromic sequence centered at base pair (bp)-42.5 from the transcription start of the *Vibrio fischeri* lux operon, which encodes the luminescence functions. With its cognate acyl-HSL, LuxR binds to the lux box and facilitates RNA polymerase binding. In some embodiments, a lux box-lie sequence can be present in promoter operably linked to a gene of interest. In some embodiments, a lux-like box sequence can be present in a promoter operably linked to a second activator polypeptide and/or a third activator polypeptide.

In some embodiments, the quorum sensing system is an rpa (RpaR) quorum sensing system. In some embodiments, the quorum sensing systems is based, at least in part, on a quorum sensing system selected from: *Rhodopseudomonas palustris, Bradyrhizobium* sp., and *Silicibacter pomeroyi*. For example, a first activator polypeptide, a second activator polypeptide, and a third activator polypeptide are selected from a quorum sensing system selected from: *Rhodopseudomonas palustris, Bradyrhizobium* sp., and *Silicibacter pomeroyi*. In another example, a second activator polypeptide and a third activator polypeptide are selected from a quorum sensing system selected from: *Rhodopseudomonas palustris, Bradyrhizobium* sp., and *Silicibacter pomeroyi*.

In some embodiments, a first activator polypeptide is a p-coumaric acid-CoA ligase, the second activator polypeptide is a RpaI synthase, and the third activator polypeptide is a RpaR signaling molecule. In some embodiments, induction of the inducible quorum sensing system is considered to have occurred when the quorum sensing molecule (e.g., the p-coumaroyl-HSL (pC-HSL) molecule) binds to the RpaR signaling molecule. In some cases, the activatable promoter operably linked to a fourth nucleic acid sequence is an activatable promoter that can be activated by a third activator polypeptide (e.g., the RpaR polypeptide) when it is bound to a quorum sensing molecule (e.g., p-coumaroyl-HSL).

In some embodiments, an inducer molecule (e.g., a p-coumaric acid) molecule is used to induce a quorum sensing system. In a non-limiting example, a non-zero p-coumaric acid concentration is converted into an intermediate molecule (e.g., a p-coumaroyl-CoA (pA)) using the enzyme 4CL2nt. The intermediate pA molecule can be referred to as a "quorum sensing molecule precursor." The intermediate product (pA) is transformed into a quorum sensing molecule (e.g., a p-coumaroyl-HSL (pC-HSL)) using a RpaI synthase enzyme. Once a threshold value of extracellular pC-HSL is reached, intracellular production of luxI driven genes (RpaI and RpaR) are brought to the ON state, due to the positive feedback provided by the QS promoter (e.g., pLux promoter). In some embodiments, as the p-coumaric acid concentration is increased, the iQS shows a first transition from a stable spiral to a limit cycle which indicates sustained oscillations. A further increase in the inducer molecule concentration causes the limit cycle to disappear in favor of a stable fixed point. In some embodiments, converting p-coumaric acid to p-coumaroyl-CoA is performed by a first activator polypeptide (e.g., the p-coumaric acid-CoA ligase), where conversion of p-coumaric acid to p-coumaroyl-CoA results in activation of the inducible quorum sensing system. In some embodiments, converting p-coumaroyl-CoA to p-coumaroyl-HSL is performed by a second activator polypeptide (e.g., RpaI synthase), where conversation of p-coumaroyl-CoA to p-courmaroyl-HSL results in activation of the inducible quorum sensing system.

In some embodiments, activation of the inducible quorum sensing system includes binding of a third activator polypeptide (e.g., a RpaR) to a quorum sensing molecule (e.g., a p-coumaroyl-HSL), where binding results in activation of the inducible quorum sensing system. In such cases, binding of a RpaR polypeptide to a p-coumaryol-HSL results in in transcriptional regulation of RpaR-regulatable promoter (e.g., a pLux promoter), where transcriptional regulation of a RpaR-regulatable promoter results in activation of the inducible quorum sensing system. In some cases, binding of a RpaR polypeptide to a p-coumaryol-HSL results in in transcriptional regulation of RpaR-regulatable promoter (e.g., a pLux promoter), where transcriptional regulation a RpaR-regulatable promoter results in activation of the gene of interest.

In some embodiments, the inducible quorum sensing system does not crosstalk with other quorum sensing systems. In such cases, there is no crosstalk between quorum sensing systems when an inducer molecule (e.g., p-coumaric acid) is used to activate the quorum sensing system. This enables the inducible quorum sensing system as described herein to be used with one or more additional quorum sensing systems. For example, the absence of cross-talk between a p-coumaric acid derived signaling molecule and the majority of well-characterized quorum sensing systems, enables the simultaneous use of multiple quorum sensing in co-culture. Non-limiting examples of quorum sensing systems that can be used in conjunction with the inducible quorum sensing system include: *Vibrio fischeri*; a las system from *Pseduomonas aeruginosa*; a rhl system from *Pseduomonas aeruginosa*; a tra system from *Agrobacterium tumefaciens*; an ahy system from *Aeromonas hydrophilia*; a sma system from *Serratia marcescens*; cer system from *Rhodobacter sphaeroides*; and an exp system from *Sinorhizobium meliloti*.

In another aspect, this disclosure features a model that accurately predicts three main dynamics of the cell population as the concentration of an inducer molecule (e.g., the p-coumaric acid) is varied. In a non-limiting example, at an inducer concentration of zero, the population grows reaching a steady state value. At small inducer molecule (e.g., p-coumaric acid) concentrations (e.g., <10 nM), the population undergoes small amplitude lysis events followed by steady state. As the p-coumaric acid concentration is increased, the simulations show a first transition from a stable spiral to a limit cycle which indicates sustained oscillations. A further increase in the inducer parameter causes the limit cycle to disappear in favor of a stable fixed point.

In some embodiments, modulating the inducer molecule concentration during the culture enables switching between states of constant growth (circuit quiescence), synchronized oscillations in population density (cyclic cargo release) and inducible population death (kill switch).

In some embodiments, the circuit functionalities of the iQS were demonstrated in the *E. Coli* strain MG1655, the circuit could potentially be extended to other bacterial species.

Isolated Nucleic Acids

Provided herein are nucleic acids sequences that encode any of the activator polypeptides described herein. Also provided herein are nucleic acids encoding any of the reporter polypeptides described herein. Also provided herein are nucleic acids encoding any of the genes of interests described herein. Also provided herein are expression vectors including any of the nucleic acid sequences described herein. In some embodiments, the expression vectors are multi-cistronic vectors and/or include bidirectional promoters.

In some embodiments of any of the nucleic acid sequences described herein, nucleic acid sequences can include any of the components described in SEQ ID NO: 2-9. In some embodiments, a nucleic acid sequences can include a sequence of any one of SEQ ID NOs: 10-12.

In some embodiments, a second nucleic acid sequence encoding a second activator polypeptide and a third nucleic acid sequence encoding a third activator polypeptide are operably linked to the same promoter (e.g., any of the activatable promoters described herein). For example, the second and third nucleic acid sequences are operably linked to a pLux promoter. In some cases, the second and third nucleic acid sequences are each operably linked to a bidirectional promoter. In some cases, the second and third nucleic acid sequences are operably linked to the same promoter via an internal ribosome entry sequence (IRES) or a self-cleaving 2A peptide. In some embodiments, the second and third nucleic acid sequences are operably linked to different promoters. For example, the second nucleic acid sequence can be linked to a first activatable promoter sequence (e.g., a first pLux promoter), and the third nucleic acid sequence can be linked to a second activatable promoter (e.g., a second pLux promoter).

Also provided herein are vectors including any of the nucleic acids described herein. In some embodiments, the vectors include any of the nucleic acid sequences as described in FIGS. 1A, 2A, 4A, 6A, and 11. The vectors described herein can include any of the combinations of nucleic acid sequences and any of the orientations as described in FIGS. 1A, 2A, 4A, 6A, and 11.

Quorum Sensing Molecule

In some embodiments, a "quorum sensing molecule" can be referred to as a quorum sensing molecule precursor or a quorum sensing molecule. In some cases, a quorum sensing molecule can be any appropriate quorum sensing molecule. In some embodiments, the quorum-sensing molecule can be an N-acyl homoserine lactone (AHL). In some embodiments, the quorum-sensing molecule can be a homoserine lactone (HSL) or a homolog thereof. For example, the quorum-sensing molecule can be p-Coumaroyl-HSL. In some embodiments, a quorum-sensing molecule can be an auto-inducing peptide (AIP) from a Gram-positive bacteria. Other quorum-sensing molecules are known in the art.

4CL2nt Gene

In some embodiments, the method includes a nucleic acid sequence encoding a p-coumaric acid-CoA ligase polypeptide. In some cases, a first activator polypeptide is a p-coumaric acid-CoA ligase. The p-coumaric acid-CoA ligase converts p-coumaric acid to p-coumaroyl-CoA. In some embodiments, the nucleic acid sequence encoding a p-coumaric acid-CoA ligase polypeptide is a 4CL2nt gene from the plant *Nicotiana tabacum*.

In some embodiments, the 4CL2nt polypeptide is encoded by a nucleic acid sequence that is at least 70% identical (e.g., at least 72%, at least 74%, at least 76%, at least 78%, at least 80%, at least 82%, at least 84%, at least 86%, at least 88%, at least 90%, at least 92%, at least 94%, at least 96%, at least 98%, at least 99%, or 100% identical) to SEQ ID NO: 1. In some embodiments, the nucleic acid sequence that encodes the 4CL2nt polypeptide can be a codon-optimized version of SEQ ID NO: 1.

In some embodiments, the nucleic acid sequence that encodes the 4CL2nt polypeptide is operably linked to a promoter. In some embodiments, the promoter is an activatable promoter (e.g., any of the exemplary activatable promoters described herein). In some embodiments, the nucleic acid sequence encoding the 4CL2nt polypeptide is operably linked to a promoter having a nucleic acid sequence that is at least 70% identical (e.g., at least 72%, at least 74%, at least 76%, at least 78%, at least 80%, at least 82%, at least 84%, at least 86%, at least 88%, at least 90%, at least 92%, at least 94%, at least 96%, at least 98%, at least 99%, or 100% identical) to SEQ ID NO: 2. In some embodiments, the promoter operably linked to the nucleic acid sequence encoding the 4CL2nt polypeptide is referred to as J23106.

Activatable Promoter

An activatable promoter can be any appropriate activatable promoter. In some embodiments, the activatable promoter can be activated, directly or indirectly, by the quorum-sensing molecule. In this way, in some embodiments, a feedback loop can be set up such that the presence of the quorum-sensing molecule drives accumulation of the quorum-sensing molecule. For example, binding of the quorum sensing molecule to a third activator polypeptide (e.g., the RpaR polypeptide) can result in activation of an activatable promoter (e.g., any of the activatable promoters described herein) operably linked to any of the activator polypeptides or genes of interest described herein. In some cases, the feedback loop is a positive feedback loop for a third activator polypeptide. For example, binding of the quorum sensing molecule to the third activator polypeptide results in activation of the promoter operably linked to the third activator polypeptide. In some cases, the feedback loop is a positive feedback loop for a second activator polypeptide (e.g., the RpaI synthase polypeptide) that converts p-coumaroyl-CoA to p-coumaroyl-HSL. In such cases, binding of the quorum sensing molecule to the third activator polypeptide results in activation of the promoter operably linked to a second activator polypeptide (e.g., the RpaI synthase polypeptide). In some cases, the feedback loop is a positive feedback loop for a gene of interest encoded by a fourth nucleic acid. In such cases, binding of the quorum sensing molecule to the third activator polypeptide results in activation of a promoter operably linked to the gene of interest.

In some embodiments, the first activatable promoter includes the same sequence as the second activatable promoter. For example, the first activatable promoter and the second activatable promoter include a sequence including one or more lux box-like sequences. In some embodiments, the first activatable promoter and the second activatable promoter are the same promoter sequence (e.g., an activatable promoter sequence that enables bidirectional expression). In some embodiments, the first activatable promoter, the second activatable promoter, and the third activatable promoter each include the same sequence. In a non-limiting example, the first activatable promoter, the second activatable promoter, and the third activatable promoter each include a sequence including one or more lux box-like sequences.

In some embodiments of any of the bacterial strains described herein, the activatable promoter is an AHL-activatable promoter. In some embodiments of any of the bacterial strains described herein, the activatable promoter is a LuxR-AHL activatable luxI promoter. In some embodiments, the activatable promoter is a RpaR-AHL activatable RpaI promoter. In some embodiments, the activatable promoter is a TraR-HSL activatable traI promoter. Other activatable promoters are known in the art.

In some embodiments, the quorum-sensing molecule is an AHL, the activatable promoter is a LuxR-AHL activatable luxI promoter, and the activator polypeptide is a LuxI. In some embodiments, the quorum-sensing molecule is an AHL, the activatable promoter is a RpaR-AHL activatable RpaI promoter, and the activator polypeptide is a RpaI. In some embodiments, the quorum-sensing molecule is a HSL, the activatable promoter is a TraR-HSL activatable traI promoter, and the activator polypeptide is a TraI. In some embodiments, the quorum-sensing molecule is a HSL, the activatable promoter is a LuxR-AHL activatable luxI promoter, and the activator polypeptide is a RpaI.

In some embodiments, the promoter can be an activatable promoter. In some embodiments, the promoter can be a promoter that is activated, directly or indirectly, by the quorum sensing molecule. In some embodiments, the promoter can be an activatable promoter as described above. In some embodiments, the promoter can be a constitutive promoter. Many constitutive promoters are known in the art.

p-Coumaric Acid

In some embodiments of any of the methods described herein, the inducer molecule includes a p-coumaric acid molecule. In some embodiments, the concentration of an inducer molecule contacted to the one or more bacterial strains determines the level of induction of the inducible quorum sensing system in the one or more bacterial strains. In some embodiments, the concentration of an inducer molecule contacted to the one or more bacterial strains results in no induction of the inducible quorum sensing system. In some cases, where there is no induction of the inducible quorum sensing system, the quorum sensing system is considered to be "OFF." In some embodiments, the concentration of an inducer molecule contacted to the one or more bacterial strains results in "intermediate" induction of the inducible quorum sensing system. As used herein, "intermediate" can refer to induction of the inducible quorum sensing system that occurs in the presence of a non-zero concentration of inducer molecule. In some embodiments, the concentration of an inducer molecule contacted to the one or more bacterial strains results in induction of the inducible quorum sensing system. In some cases, where there is induction of the inducible quorum sensing system, the inducible quorum sensing system is considered to be "ON."

In some embodiments, the inducer molecule (e.g., p-coumaric acid) that is contacted with the one or more biological strains includes a concentration of between about 1 nM to about 1000 nM (e.g., about 1 nM to about 900 nM, about 1 nM to about 800 nM, about 1 nM to about 700 nM, about 1 nM to about 600 nM, about 1 nM to about 500 nM, about 1 nM to about 400 nM, about 1 nM to about 300 nM, about 1 nM to about 200 nM, about 1 nM to about 100 nM, about 1 nM to about 90 nM, about 1 nM to about 80 nM, about 1 nM to about 70 nM, about 1 nM to about 60 nM, about 1 nM to about 50 nM, about 1 nM to about 40 nM, about 1 nM to about 30 nM, about 1 nM to about 20 nM, about 1 nM to about 10 nM, about 1 nM to about 9 nM, about 1 nM to about 8 nM, about 1 nM to about 7 nM, about 1 nM to about 6 nM, about 1 nM to about 5 nM, about 1 nM to about 4 nM, about 1 nM to about 3 nM, about 1 nM to about 2 nM, about 2 nM to about 1000 nM, about 2 nM to about 900 nM, about 2 nM to about 800 nM, about 2 nM to about 700 nM, about 2 nM to about 600 nM, about 2 nM to about 500 nM, about 2 nM to about 400 nM, about 2 nM to about 300 nM, about 2 nM to about 200 nM, about 2 nM to about 100 nM, about 2 nM to about 90 nM, about 2 nM to about 80 nM, about 2 nM to about 70 nM, about 2 nM to about 60 nM, about 2 nM to about 50 nM, about 2 nM to about 40 nM, about 2 nM to about 30 nM, about 2 nM to about 20 nM, about 2 nM to about 10 nM, about 2 nM to about 9 nM, about 2 nM to about 8 nM, about 2 nM to about 7 nM, about 2 nM to about 6 nM, about 2 nM to about 5 nM, about 2 nM to about 4 nM, about 2 nM to about 3 nM, about 3 nM to about 1000 nM, about 3 nM to about 900 nM, about 3 nM to about 800 nM, about 3 nM to about 700 nM, about 3 nM to about 600 nM, about 3 nM to about 500 nM, about 3 nM to about 400 nM, about 3 nM to about 300 nM, about 3 nM to about 200 nM, about 3 nM to about 100 nM, about 3 nM to about 90 nM, about 3 nM to about 80 nM, about 3 nM to about 70 nM, about 3 nM to about 60 nM, about 3 nM to about 50 nM, about 3 nM to about 40 nM, about 3 nM to about 30 nM, about 3 nM to about 20 nM, about 3 nM to about 10 nM, about 3 nM to about 9 nM, about 3 nM to about 8 nM, about 3 nM to about 7 nM, about 3 nM to about 6 nM, about 3 nM to about 5 nM, about 3 nM to about 4 nM, about 4 nm to about 1000 nM, about 4 nM to about 900 nM, about 4 nM to about 800 nM, about 4 nM to about 700 nM, about 4 nM to about 600 nM, about 4 nM to about 500 nM, about 4 nM to about 400 nM, about 4 nM to about 300 nM, about 4 nM to about 200 nM, about 4 nM to about 100 nM, about 4 nM to about 90 nM, about 4 nM to about 80 nM, about 4 nM to about 70 nM, about 4 nM to about 60 nM, about 4 nM to about 50 nM, about 4 nM to about 40 nM, about 4 nM to about 30 nM, about 4 nM to about 20 nM, about 4 nM to about 10 nM, about 4 nM to about 9 nM, about 4 nM to about 8 nM, about 4 nM to about 7 nM, about 4 nM to about 6 nM, about 4 nM to about 5 nM, about 5 nM to about 1000 nM, about 5 nM to about 900 nM, about 5 nM to about 800 nM, about 5 nM to about 700 nM, about 5 nM to about 600 nM, about 5 nM to about 500 nM, about 5 nM to about 400 nM, about 5 nM to about 300 nM, about 5 nM to about 200 nM, about 5 nM to about 100 nM, about 5 nM to about 90 nM, about 5 nM to about 80 nM, about 5 nM to about 70 nM, about 5 nM to about 60 nM, about 5 nM to about 50 nM, about 5 nM to about 40 nM, about 5 nM to about 30 nM, about 5 nM to about 20 nM, about 5 nM to about 10 nM, about 5 nM to about 9 nM, about 5 nM to about 8 nM, about 5 nM to about 7 nM, about 5 nM to about 6 nM, about 6 nM to about 1000 nM, about 6 nM to about 900 nM, about 6 nM to about 800 nM, about 6 nM to about 700 nM, about 6 nM to about 600 nM, about 6 nM to about 500 nM, about 6 nM to about 400 nM, about 6 nM to about 300 nM, about 6 nM to about 200 nM, about 6 nM to about 100 nM, about 6 nM to about 90 nM, about 6 nM to about 80 nM, about 6 nM to about 70 nM, about 6 nM to about 60 nM, about 6 nM to about 50 nM, about 6 nM to about 40 nM, about 6 nM to about 30 nM, about 6 nM to about 20 nM, about 6 nM to about 10 nM, about 6 nM to about 9 nM, about 6 nM to about 8 nM, about 6 nM to about 7 nM, about 7 nM to about 1000 nM, about 7 nM to about 900 nM, about 7 nM to about 800 nM, about 7 nM to about 700 nM, about 7 nM to about 600 nM, about 7 nM to about 500 nM, about 7 nM to about 400 nM, about 7 nM to about 300 nM, about 7 nM to about 200 nM, about 7 nM to about 100 nM, about 7 nM to about 90 nM, about 7 nM to about 80 nM, about 7 nM to about 70 nM, about 7 nM to about 60 nM, about 7 nM to about 50 nM, about 7 nM to about 40 nM, about 7 nM to about 30 nM, about 7 nM to about 20 nM, about 7 nM to about 10 nM, about 7 nM to about 9 nM, about 7 nM to about 8 nM, about 8 nM to about 1000 nM, about 8 nM to about 900 nM, about 8 nM to about 800 nM, about 8 nM to about 700 nM, about 8 nM to about 600 nM, about 8 nM to about 500 nM, about 8 nM to about 400 nM, about 8 nM to about 300 nM, about 8 nM to about 200 nM, about 8 nM to about 100 nM, about 8 nM to about 90 nM, about 8 nM to about 80 nM, about 8 nM to about 70 nM, about 8 nM to about 60 nM, about 8 nM to about 50 nM, about 8 nM to about 40 nM, about 8 nM to about 30 nM, about 8 nM to about 20 nM, about 8 nM to about 10 nM, about 8 nM to about 9 nM, about 9 nM to about 1000 nM, about 9 nM to about 900 nM, about 9 nM to about 800 nM, about 9 nM to about 700 nM, about 9 nM to about 600 nM, about 9 nM to about 500 nM, about 9 nM to about 400 nM, about 9 nM to about 300 nM, about 9 nM to about 200 nM, about 9 nM to about 100 nM, about 9 nM to about 90 nM, about 9 nM to about 80 nM, about 9 nM to about 70 nM, about 9 nM to about 60 nM, about 9 nM to about 50 nM, about 9 nM to about 40 nM, about 9 nM to about 30 nM, about 9 nM to about 20 nM, about 9 nM to about 10 nM, about 10 nM to about 1000 nM, about 10 nM to about 900 nM, about 10 nM to about 800 nM, about 10 nM to about 700 nM, about 10 nM to about 600 nM, about 10 nM to about 500 nM, about 10 nM to about 400 nM, about 10 nM to about 300 nM, about 10 nM to about 200 nM, about 10 nM to about 100 nM, about 10 nM to about 90 nM, about 10 nM to about 80 nM, about 10 nM to about 70 nM, about 10 nM to about 60 nM, about 10 nM to about 50 nM, about 10 nM to about 40 nM, about 10 nM to about 30 nM, about 10 nM to about 20 nM, about 20 nM to about 1000 nM, about 20 nM to about 900 nM, about 20 nM to about 800 nM, about 20 nM to about 700 nM, about 20 nM to about 600 nM, about 20 nM to about 500 nM, about 20 nM to about 400 nM, about 20 nM to about 300 nM, about 20 nM to about 200 nM, about 20 nM to about 100 nM, about 20 nM to about 90 nM, about 20 nM to about 80 nM, about 20 nM to about 70 nM, about 20 nM to about 60 nM, about 20 nM to about 50 nM, about 20 nM to about 40 nM, about 20 nM to about 30 nM, about 30 nM to about 1000 nM, about 30 nM to about 900 nM, about 30 nM to about 800 nM, about 30 nM to about 700 nM, about 30 nM to about 600 nM, about 30 nM to about 500 nM, about 30 nM to about 400 nM, about 30 nM to about 300 nM, about 30 nM to about 200 nM, about 30 nM to about 100 nM, about 30 nM to about 90 nM, about 30 nM to about 80 nM, about 30 nM to about 70 nM, about 30 nM to about 60 nM, about 30 nM to about 50 nM, about 30 nM to about 40 nM, about 40 nM to about 1000 nM, about 40 nM to about 900 nM, about 40 nM to about 800 nM, about 40 nM to about 700 nM, about 40 nM to about 600 nM, about 40 nM to about 500 nM, about 40 nM to about 400 nM, about 40 nM to about 300 nM, about 40 nM to about 200 nM, about 40 nM to about 100 nM, about 40 nM to about 90 nM, about 40 nM to about 80 nM, about 40 nM to about 70 nM, about 40 nM to about 60 nM, about 40 nM to about 50 nM, about 50 nM to about 1000 nM, about 50 nM to about 900 nM, about 50 nM to about 800 nM, about 50 nM to about 700 nM, about 50 nM to about 600 nM, about 50 nM to about 500 nM, about 50 nM to about 400 nM, about 50 nM to about 300 nM, about 50 nM to about 200 nM, about 50 nM to about 100 nM, about 50 nM to about 90 nM, about 50 nM to about 80 nM, about 50 nM to about 70 nM, about 50 nM to about 60 nM, about 60 nM to about 1000 nM, about 60 nM to about 900 nM, about 60 nM to about 800 nM, about 60 nM to about 700 nM, about 60 nM to about 600 nM, about 60 nM to about 500 nM, about 60 nM to about 400 nM, about 60 nM to about 300 nM, about 60 nM to about 200 nM, about 60 nM to about 100 nM, about 60 nM to about 90 nM, about 60 nM to about 80 nM, about 60 nM to about 70 nM, about 70 nM to about 1000 nM, about 70 nM to about 900 nM, about 70 nM to about 800 nM, about 70 nM to about 700 nM, about 70 nM to about 600 nM, about 70 nM to about 500 nM, about 70 nM to about 400 nM, about 70 nM to about 300 nM, about 70 nM to about 200 nM, about 70 nM to about 100 nM, about 70 nM to about 90 nM, about 70 nM to about 80 nM, about 80 nM to about 1000 nM, about 80 nM to about 900 nM, about 80 nM to about 800 nM, about 80 nM to about 700 nM, about 80 nM to about 600 nM, about 80 nM to about 500 nM, about 80 nM to about 400 nM, about 80 nM to about 300 nM, about 80 nM to about 200 nM, about 80 nM to about 100 nM, about 80 nM to about 90 nM, about 90 nM to about 1000 nM, about 90 nM to about 900 nM, about 90 nM to about 800 nM, about 90 nM to about 700 nM, about 90 nM to about 600 nM, about 90 nM to about 500 nM, about 90 nM to about 400 nM, about 90 nM to about 300 nM, about 90 nM to about 200 nM, about 90 nM to about 100 nM, about 100 nM to about 1000 nM, about 100 nM to about 900 nM, about 100 nM to about 800 nM, about 100 nM to about 700 nM, about 100 nM to about 600 nM, about 100 nM to about 500 nM, about 100 nM to about 400 nM, about 100 nM to about 300 nM, about 100 nM to about 200 nM, about 200 nM to about 1000 nM, about 200 nM to about 900 nM, about 200 nM to about 800 nM, about 200 nM to about 700 nM, about 200 nM to about 600 nM, about 200 nM to about 500 nM, about 200 nM to about 400 nM, about 200 nM to about 300 nM, about 300 nM to about 1000 nM, about 300 nM to about 900 nM, about 300 nM to about 800 nM, about 300 nM to about 700 nM, about 300 nM to about 600 nM, about 300 nM to about 500 nM, about 300 nM to about 400 nM, about 400 nM to about 1000 nM, about 400 nM to about 900 nM, about 400 nM to about 800 nM, about 400 nM to about 700 nM, about 400 nM to about 600 nM, about 400 nM to about 500 nM, about 500 nM to about 1000 nM, about 500 nM to about 900 nM, about 500 nM to about 800 nM, about 500 nM to about 700 nM, about 500 nM to about 600 nM, about 600 nM to about 1000 nM, about 600 nM to about 900 nM, about 600 nM to about 800 nM, about 600 nM to about 700 nM, about 700 nM to about 1000 nM, about 700 nM to about 900 nM, about 700 nM to about 800 nM, about 800 nM to about 1000 nM, about 800 nM to about 900 nM, or about 900 nM to about 1000 nM). In some embodiments, the concentration of inducer molecule (e.g., p-coumaric acid) that results in induction of the inducible quorum sensing system is 1 μM, 2 μM, 3 μM, 4 μM, 5 μM, 6 μM, 7 μM, 8 μM, 9 μM, or 10 μM or more.

In some embodiments, the inducer molecule concentration can be modulated during the culture of any one of the one or more bacterial strains. For example, the culture can include a first concentration for a first period of time and a second concentration for a second period of time. In some embodiments, the cultures can include a third concentration for a third period of time. In some embodiments, the cultures can include a fourth concentration for a fourth period of time. Modulating the inducer molecule concentration during the culture enables switching between states of constant growth (circuit quiescence), synchronized oscillations in population density (cyclic cargo release) and inducible population death (kill switch).

In some embodiments, the concentration of the inducer molecule (e.g., p-coumaric acid) that induces the quorum sensing system (e.g., quorum sensing system is considered in the "ON" state) when administered is between about 15 nM to about 1000 nM (or any of the subranges described herein).

In some embodiments, the concentration of the inducer molecule (e.g., p-coumaric acid) that results in intermediate induction of the quorum sensing system is between about 0.1 nM to about 1 nM (e.g., about 0.1 nM to about 0.9 nM, about 0.1 nM to about 0.8 nM, about 0.1 nM to about 0.7 nM, about 0.1 nM to about 0.6 nM, about 0.1 nM to about 0.7 nM, about 0.1 nM to about 0.6 nM, about 0.1 nM to about 0.5 nM, about 0.1 nM to about 0.4 nM, about 0.1 nM to about 0.3 nM, about 0.1 nM to about 0.2 nM, about 0.2 nM to about 1 nM, about 0.2 nM to about 0.9 nM, about 0.2 nM to about 0.8 nM, about 0.2 nM to about 0.7 nM, about 0.2 nM to about 0.6 nM, about 0.2 nM to about 0.7 nM, about 0.2 nM to about 0.6 nM, about 0.2 nM to about 0.5 nM, about 0.2 nM to about 0.4 nM, about 0.2 nM to about 0.3 nM, about 0.3 nM to about 1 nM, about 0.3 nM to about 0.9 nM, about 0.3 nM to about 0.8 nM, about 0.3 nM to about 0.7 nM, about 0.3 nM to about 0.6 nM, about 0.3 nM to about 0.7 nM, about 0.3 nM to about 0.6 nM, about 0.3 nM to about 0.5 nM, about 0.3 nM to about 0.4 nM, about 0.4 nM to about 1 nM, about 0.4 nM to about 0.9 nM, about 0.4 nM to about 0.8 nM, about 0.4 nM to about 0.7 nM, about 0.4 nM to about 0.6 nM, about 0.4 nM to about 0.7 nM, about 0.4 nM to about 0.6 nM, about 0.4 nM to about 0.5 nM, about 0.5 nM to about 1 nM, about 0.5 nM to about 0.9 nM, about 0.5 nM to about 0.8 nM, about 0.5 nM to about 0.7 nM, about 0.5 nM to about 0.6 nM, about 0.6 nM to about 1 nM, about 0.6 nM to about 0.9 nM, about 0.6 nM to about 0.8 nM, about 0.6 nM to about 0.7 nM, about 0.7 nM to about 1 nM, about 0.7 nM to about 0.9 nM, about 0.7 nM to about 0.8 nM, about 0.8 nM to about 1 nM, about 0.8 nM to about 0.9 nM, or about 0.9 nM to about 1 nM).

In some embodiments, the one or more bacterial strains are contacted with an inducer molecule (e.g., a p-coumaric acid) for about 1 hour to about 60 hours (e.g., about 1 hour to about 58 hours, about 1 hour to about 56 hours, about 1 hour to about 54 hours, about 1 hour to about 52 hours, about 1 hour to about 50 hours, about 1 hour to about 48 hours, about 1 hour to about 46 hours, about 1 hour to about 44 hours, about 1 hour to about 42 hours, about 1 hour to about 40 hours, about 1 hour to about 38 hours, about 1 hour to about 36 hours, about 1 hour to about 34 hours, about 1 hour to about 32 hours, about 1 hour to about 30 hours, about 1 hour to about 28 hours, about 1 hour to about 26 hours, about 1 hour to about 24 hours, about 1 hour to about 22 hours, about 1 hour to about 20 hours, about 1 hour to about 18 hours, about 1 hour to about 16 hours, about 1 hour to about 14 hours, about 1 hour to about 12 hours, about 1 hour to about 10 hours, about 1 hour to about 8 hours, about 1 hour to about 6 hours, about 1 hour to about 4 hours, about 1 hour to about 2 hours, about 2 hours to about 32 hours, about 2 hours to about 30 hours, about 2 hours to about 28 hours, about 2 hours to about 26 hours, about 2 hours to about 24 hours, about 2 hours to about 22 hours, about 2 hours to about 20 hours, about 2 hours to about 18 hours, about 2 hours to about 16 hours, about 2 hours to about 14 hours, about 2 hours to about 12 hours, about 2 hours to about 10 hours, about 2 hours to about 8 hours, about 2 hours to about 6 hours, about 2 hours to about 4 hours, about 4 hours to about 32 hours, about 4 hours to about 30 hours, about 4 hours to about 28 hours, about 4 hours to about 26 hours, about 4 hours to about 24 hours, about 4 hours to about 22 hours, about 4 hours to about 20 hours, about 4 hours to about 18 hours, about 4 hours to about 16 hours, about 4 hours to about 14 hours, about 4 hours to about 12 hours, about 4 hours to about 10 hours, about 4 hours to about 8 hours, about 4 hours to about 6 hours, about 6 hours to about 32 hours, about 6 hours to about 30 hours, about 6 hours to about 28 hours, about 6 hours to about 26 hours, about 6 hours to about 24 hours, about 6 hours to about 22 hours, about 6 hours to about 20 hours, about 6 hours to about 18 hours, about 6 hours to about 16 hours, about 6 hours to about 14 hours, about 6 hours to about 12 hours, about 6 hours to about 10 hours, about 6 hours to about 8 hours, about 8 hours to about 32 hours, about 8 hours to about 30 hours, about 8 hours to about 28 hours, about 8 hours to about 26 hours, about 8 hours to about 24 hours, about 8 hours to about 22 hours, about 8 hours to about 20 hours, about 8 hours to about 18 hours, about 8 hours to about 16 hours, about 8 hours to about 14 hours, about 8 hours to about 12 hours, about 8 hours to about 10 hours, about 10 hours to about 32 hours, about 10 hours to about 30 hours, about 10 hours to about 28 hours, about 10 hours to about 26 hours, about 10 hours to about 24 hours, about 10 hours to about 22 hours, about 10 hours to about 20 hours, about 10 hours to about 18 hours, about 10 hours to about 16 hours, about 10 hours to about 14 hours, about 10 hours to about 12 hours, about 12 hours to about 32 hours, about 12 hours to about 30 hours, about 12 hours to about 28 hours, about 12 hours to about 26 hours, about 12 hours to about 24 hours, about 12 hours to about 22 hours, about 12 hours to about 20 hours, about 12 hours to about 18 hours, about 12 hours to about 16 hours, about 12 hours to about 14 hours, about 14 hours to about 32 hours, about 14 hours to about 30 hours, about 14 hours to about 28 hours, about 14 hours to about 26 hours, about 14 hours to about 24 hours, about 14 hours to about 22 hours, about 14 hours to about 20 hours, about 14 hours to about 18 hours, about 14 hours to about 16 hours, about 16 hours to about 32 hours, about 16 hours to about 30 hours, about 16 hours to about 28 hours, about 16 hours to about 26 hours, about 16 hours to about 24 hours, about 16 hours to about 22 hours, about 16 hours to about 20 hours, about 16 hours to about 18 hours, about 18 hours to about 32 hours, about 18 hours to about 30 hours, about 18 hours to about 28 hours, about 18 hours to about 26 hours, about 18 hours to about 24 hours, about 18 hours to about 22 hours, about 18 hours to about 20 hours, about 20 hours to about 32 hours, about 20 hours to about 30 hours, about 20 hours to about 28 hours, about 20 hours to about 26 hours, about 20 hours to about 24 hours, about 20 hours to about 22 hours, about 22 hours to about 32 hours, about 22 hours to about 30 hours, about 22 hours to about 28 hours, about 22 hours to about 26 hours, about 22 hours to about 24 hours, about 24 hours to about 32 hours, about 24 hours to about 30 hours, about 24 hours to about 28 hours, about 24 hours to about 26 hours, about 26 hours to about 32 hours, about 26 hours to about 30 hours, about 26 hours to about 28 hours, about 28 hours to about 32 hours, about 28 hours to about 30 hours, about 30 hours to about 32 hours, about 24 hour to about 50 hours, about 30 hour to about 50 hours, about 36 hour to about 50 hours, about 24 hour to about 48 hours, about 24 hour to about 36 hours, or about 36 hour to about 48 hours). In some embodiments, the method includes contacting the one or more bacterial strains with an inducer molecule (e.g., p-coumaric acid) for about 1 day, about 2 days, about 3 days, about 4 days, about 5 days, about 6 days, about 7 days, about 8 days, about 9 days, or about 10 or more days.

Synchronized Lysis Circuit

In some embodiments, any of the bacterial strains described herein can produce a therapeutic protein or a suite of therapeutic proteins, the expression of which can be controlled by a genetic circuit such as a Synchronized Lysis Circuit (SLC). In some embodiments, exemplary SLC's can include those described in International Application No. PCT/US18/33555, which is incorporated herein by reference in its entirety. The quorum driven synchronized lysis circuit (SLC) has been investigated for microbial therapeutics such as drug delivery to tumors in vivo. With the SLC circuit, a quorum sensing molecule (AHL), gradually accumulates in the growth environment in proportion to population density. When the population reaches a threshold density, synchronized lysis eliminates around 90% of the bacteria, leaving about 10% to reseed population growth. The resulting dynamics of the cell population are cycles of cell growth and synchronized lysis. However, when employed in in vivo environments where selective media cannot be used, plasmid loss or mutations are expected to result in loss of function over long time periods. In some embodiment, a circuit designed for monocultures, such as the SLC, can have drastically broadened use-cases when expanded into the setting of a community. In some embodiments, the methods include orthogonal co-lysis or "ortholysis" systems, methods, and compositions that can be used for in situ drug delivery systems. In some embodiments, this phenomenon of stably co-culturing two metabolically competitive strains through orthogonal self-lysing offers the possibility of many unique applications beyond drug delivery where the use of synthetic microbial ecosystems is advantageous.

In some embodiments, the gene of interest encodes a bacteriophage lytic protein capable of forming a lesion in a host cell's membrane. A non-limiting example of a gene of interest that is capable of forming a lesion in a host cell's membrane includes the bacteriophage ΦX174 gene. In some embodiments, the binding of the quorum sensing molecule to the third activator polypeptide results in activation of the promoter operably linked to the gene of interest. For example, the binding of p-coumaroyl-HSL to the RpaR polypeptide results in activation of the promoter operably linked to the nucleic acid sequence encoding bacteriophage ΦX174.

Gene of Interest

In some embodiments, the method includes one or more bacterial strains having a fourth nucleic acid encoding a gene of interest. In some embodiments, the gene of interest is a therapeutic gene product. In some embodiments, a therapeutic gene product can be a therapeutic agent. In some embodiments, a therapeutic agent can be any of the therapeutic agents described herein. For example, in some embodiments, a therapeutic agent can be selected from the group consisting of: an inhibitory nucleic acid (e.g., siRNA, shRNA, miRNA, or antisense (e.g., antisense DNA, antisense RNA, or a synthetic analog)), a cytokine, an enzyme, a peptide hormone, a fusion protein, a clotting factor, and an antibody or antigen-binding fragment thereof. In some embodiments, an additional nucleic acid and/or protein (e.g., a heterologous nucleic acid and/or protein) may be secreted, exocytosed, or otherwise exported from a bacterial strain as described herein. In some embodiments, an additional nucleic acid and/or protein (e.g., a heterologous nucleic acid and/or protein) may be released upon lysis of a bacterial strain as described herein. In some embodiments, an additional nucleic acid and/or protein (e.g., a heterologous nucleic acid and/or protein) may be displayed on the surface a bacterial strain as described herein.

In some instances, the therapeutic agent is a therapeutic polypeptide. In some instances, the therapeutic polypeptide includes one or more polypeptides (e.g., 2, 3, 4, 5, or 6). In some instances, the therapeutic polypeptide is conjugated to a toxin, a radioisotope, or a drug via a linker (e.g., a cleavable linker, a non-cleavable linker).

In some instances, the therapeutic agent is cytotoxic or cytostatic to a target cell. The phrase "cytotoxic to a target cell" refers to the inducement, directly or indirectly, in the death (e.g., necrosis or apoptosis) of the target cell. For example, a target cell can be a cancer cell (e.g., a cancerous cell or a tumor-associated immune cell (e.g., macrophage) or an infected cell.

Toxin/Antitoxin System

In some embodiments, a vector includes a vector-stabilizing element. For example, a vector stabilizing element can be part of the toxin/antitoxin system. In some embodiments, the toxin/antitoxin system may be replaced by a bacteriocin/immunity protein system. As used herein, the term "toxin/antitoxin" includes both the toxin/antitoxin systems described herein above, including bacteriocin/immunity protein systems. Bacteriocins are ribosomally-synthesized peptides that are produced by bacteria. Bacteriocins are non-toxic to bacteria that produce the bacteriocins and are generally toxic to other bacteria. Typically, a bacterium that produces a bacteriocin also produces an immunity protein that can inhibit or prevent the toxic effect of the bacteriocin. Accordingly, a bacteriocin and a corresponding immunity protein can be used in an analogous fashion to a toxin/antitoxin system as described herein. Most bacteriocins are extremely potent, and exhibit antimicrobial activity at nanomolar concentrations. By way of example, eukaryotic produced microbials have 102 to 103 lower activities.

Non-limiting examples of bacteriocins that can be included in any of the bacteria strains, systems and methods described herein include: acidocin, actagardine, agrocin, alveicin, aureocin, aureocin A53, aureocin A70, bisin, carnocin, carnocyclin, caseicin, cerein, circularin A, colicin, curvaticin, divercin, duramycin, enterocin, enterolysin, epidermin/gallidermin, erwiniocin, gardimycin, gassericin A, glycinecin, halocin, klebicin, lactosin S, lactococcin, lacticin, leucoccin, lysostaphin, macedocin, mersacidin, mesentericin, microbisporicin, microcin S, mutacin, nisin, paenibacillin, planosporicin, pediocin, pentocin, plantaricin, pneumocyclicin, pyocin, reutericin 6, sakacin, salivaricin, sublancin, subtilin, sulfolobicin, tasmancin, thuricin 17, trifolitoxin, variacin, vibriocin, warnericin, cytolisin, pyocyn S2, colicin A, colicin E1, microcin MccE492, and warnerin.

In some embodiments, the bacteriocin is obtained from a Gram negative bacteria (e.g., microcins (e.g., microcin V of *E. coli*, subtilosin A from *B. subtillis*), colicins (E.g., colicin produced by and toxic to certain strains of *E. coli* (e.g., colicin A, colicin B, colicin E1, colicin E3, colicin E5, and colicin E7), tailocins (e.g., R-type pyocins, F-type pyocins)).

In some embodiments, the bacteriocin is obtained from a Gram positive bacteria (e.g., class I bacteriocins (e.g., Nisin, lantibiotics), class II bacteriocins (e.g., IIa pediocin-like bacteriocins, IIb bacteriocins (e.g., lactococcin G), IIc cyclic peptides (e.g., enterocin AS-48), IId single peptide bacteriocins (e.g., aureocin A53), class III bacteriocins (e.g., IIIa (e.g., bacteriolysins), and IIIb (which kill the target by disrupting the membrane potential), or class IV bacteriocins (e.g., complex bacteriocins containing lipid or carbohydrate moieties)).

Methods of Introducing a Nucleic Acid in a Cell

Any of the isolated nucleic acids described herein can be introduced into any cell, e.g., a bacterial cell. Methods of introducing nucleic acids and expression vectors into a bacterial cell are known in the art. For example, transformation can be used to introduce a nucleic acid into a bacterial cell.

Culturing Bacterial Strains

Methods of culturing bacterial cells are well known in the art. Cells can be maintained in vitro under conditions that favor cell proliferation, cell growth, and/or cell differentiation. For example, cells can be cultured by contacting a cell (e.g., any of the cells described herein) with a cell culture medium that includes supplemental growth factors to support cell viability and cell growth.

In some embodiments, the culturing or co-culturing occurs in a microfluidic device. In some embodiments, the culturing or co-culturing occurs in a cell culture vessel (e.g., a cell culture plate, a bioreactor) (see PCT/US2018/213815, herein incorporated by reference in its entirety).

Also provided herein are methods of co-culturing at least two (e.g., at least three, at least four, at least five, at least six, at least seven, at least eight, at least nine, at least ten, at least eleven, at least twelve, 2, 3, 4, 5, 6, 7, 8, 9, 10, 11 or 12)

bacterial strains (e.g., any of the bacterial strains described herein). In some embodiments, a ratio of inoculation of at least one bacterial strain to at least one other bacterial strain is between 100000:1 and 1:100000 (e.g., 100000:1, 95000:1, 90000:1, 85000:1, 80000:1, 75000:1, 70000:1, 65000:1, 60000:1, 55000:1, 50000:1, 45000:1, 40000:1, 35000:1, 30000:1, 25000:1, 20000:1, 15000:1, 10000:1, 9000:1, 8500:1, 8000:1, 7500:1, 7000:1, 6500:1, 6000:1, 5500:1, 5000:1, 4500:1, 4000:1, 3500:1, 3000:1, 2500:1, 2000:1, 1500:1, 1000:1, 950:1, 900:1, 850:1, 800:1, 750:1, 700:1, 650:1, 600:1, 550:1, 500:1, 450:1, 400:1, 350:1, 300:1, 250:1, 200:1, 150:1, 100:1, 90:1, 80:1, 70:1, 60:1, 50:1, 40:1, 30:1, 25:1, 20:1, 18:1, 16:1, 15:1, 14:1, 12:1, 10:1, 8:1, 6:1, 4:1, 3:1, 2:1, 1:1, 1:2, 1:3, 1:4, 1:6, 1:8, 1:10, 1:12, 1:14, 1:15, 1:16, 1:18, 1:20, 1:25, 1:30, 1:40, 1:50, 1:60, 1:70, 1:80, 1:90, 1:100, 1:150, 1:200, 1:250, 1:300, 1:350, 1:400, 1:450, 1:500, 1:550, 1:600, 1:650, 1:700, 1:750, 1:800, 1:850, 1:900, 1:950, 1:1000, 1:1500, 1:2000, 1:2500, 1:3000, 1:3500, 1:4000, 1:4500, 1:5000, 1:5500, 1:6000, 1:6500, 1:7000, 1:7500, 1:8000, 1:8500, 1:9000, 1:9500, 1:10000, 1:15000, 1:20000, 1:25000, 1:30000, 1:35000, 1:40000, 1:45000, 1:50000, 1:55000, 1:60000, 1:65000, 1:70000, 1:75000, 1:80000, 1:85 000, 1:90000, 1:950000, 1:100000).

In some embodiments, a ratio of inoculation of the first bacterial strain to the second bacterial strain is between 100000:1 and 1:100000 (e.g., 100000:1, 95000:1, 90000:1, 85000:1, 80000:1, 75000:1, 70000:1, 65000:1, 60000:1, 55000:1, 50000:1, 45000:1, 40000:1, 35000:1, 30000:1, 25000:1, 20000:1, 15000:1, 10000:1, 9000:1, 8500:1, 8000:1, 7500:1, 7000:1, 6500:1, 6000:1, 5500:1, 5000:1, 4500:1, 4000:1, 3500:1, 3000:1, 2500:1, 2000:1, 1500:1, 1000:1, 950:1, 900:1, 850:1, 800:1, 750:1, 700:1, 650:1, 600:1, 550:1, 500:1, 450:1, 400:1, 350:1, 300:1, 250:1, 200:1, 150:1, 100:1, 90:1, 80:1, 70:1, 60:1, 50:1, 40:1, 30:1, 25:1, 20:1, 18:1, 16:1, 15:1, 14:1, 12:1, 10:1, 8:1, 6:1, 4:1, 3:1, 2:1, 1:1, 1:2, 1:3, 1:4, 1:6, 1:8, 1:10, 1:12, 1:14, 1:15, 1:16, 1:18, 1:20, 1:25, 1:30, 1:40, 1:50, 1:60, 1:70, 1:80, 1:90, 1:100, 1:150, 1:200, 1:250, 1:300, 1:350, 1:400, 1:450, 1:500, 1:550, 1:600, 1:650, 1:700, 1:750, 1:800, 1:850, 1:900, 1:950, 1:1000, 1:1500, 1:2000, 1:2500, 1:3000, 1:3500, 1:4000, 1:4500, 1:5000, 1:5500, 1:6000, 1:6500, 1:7000, 1:7500, 1:8000, 1:8500, 1:9000, 1:9500, 1:10000, 1:15000, 1:20000, 1:25000, 1:30 000, 1:35000, 1:40000, 1:45000, 1:50000, 1:55000, 1:60000, 1:65000, 1:70 000, 1:75000, 1:80000, 1:85000, 1:90000, 1:950000, 1:100000).

In some embodiments, a cycle of lysis of any of the bacterial strains described herein can be between 1 hour to 35 days (e.g., 1 hour to 30 days, 1 hour to 28 days, 1 hour to 26 days, 1 hour to 25 days, 1 hour to 24 days, 1 hour to 22 days, 1 hour to 20 days, 1 hour to 18 days, 1 hour to 16 days, 1 hour to 14 days, 1 hour to 12 days, 1 hour to 10 days, 1 hour to 8 days, 1 hour to 7 days, 1 hour to 6 days, 1 hour to 5 days, 1 hour to 4 days, 1 hour to 72 hours, 1 hour to 70 hours, 1 hour to 68 hours, 1 hour to 66 hours 1 hour to 64 hours, 1 hour to 62 hours, 1 hour to 60 hours, 1 hour to 58 hours, 1 hour to 56 hours, 1 hour to 54 hours, 1 hour to 52 hours, 1 hour to 50 hours, 1 hour to 48 hours, 1 hour to 46 hours, 1 hour to 44 hours, 1 hour to 40 hours, 1 hour to 38 hours, 1 hour to 36 hours, 1 hour to 34 hours, 1 hour to 32 hours, 1 hour to 30 hours, 1 hour to 28 hours, 1 hour to 26 hours, 1 hour to 24 hours, 1 hour to 22 hours, 1 hour to 20 hours, 1 hour to 18 hours, 1 hour to 16 hours, 1 hour to 14 hours, 1 hour to 12 hours, 1 hour to 10 hours, 1 hour to 8 hours, 1 hour to 6 hours, 1 hour to 4 hours, 1 hour to 2 hours, 2 hours to 35 days, 2 hours to 30 days, 2 hours to 28 days, 2 hours to 26 days, 2 hours to 25 days, 2 hours to 24 days, 2 hours to 22 days, 2 hours to 20 days, 2 hours to 18 days, 2 hours to 16 days, 2 hours to 14 days, 2 hours to 12 days, 2 hours to 10 days, 2 hours to 8 days, 2 hours to 7 days, 2 hours to 6 days, 2 hours to 5 days, 2 hours to 4 days, 2 hours to 72 hours, 2 hours to 70 hours, 2 hours to 68 hours, 2 hours to 66 hours 2 hours to 64 hours, 2 hours to 62 hours, 2 hours to 60 hours, 2 hours to 58 hours, 2 hours to 56 hours, 2 hours to 54 hours, 2 hours to 52 hours, 2 hours to 50 hours, 2 hours to 48 hours, 2 hours to 46 hours, 2 hours to 44 hours, 2 hours to 40 hours, 2 hours to 38 hours, 2 hours to 36 hours, 2 hours to 34 hours, 2 hours to 32 hours, 2 hours to 30 hours, 2 hours to 28 hours, 2 hours to 26 hours, 2 hours to 24 hours, 2 hours to 22 hours, 2 hours to 20 hours, 2 hours to 18 hours, 2 hours to 16 hours, 2 hours to 14 hours, 2 hours to 12 hours, 2 hours to 10 hours, 2 hours to 8 hours, 2 hours to 6 hours, 2 hours to 4 hours, 4 hours to 35 days, 4 hours to 30 days, 4 hours to 28 days, 4 hours to 26 days, 4 hours to 25 days, 4 hours to 24 days, 4 hours to 22 days, 4 hours to 20 days, 4 hours to 18 days, 4 hours to 16 days, 4 hours to 14 days, 4 hours to 12 days, 4 hours to 10 days, 4 hours to 8 days, 4 hours to 7 days, 4 hours to 6 days, 4 hours to 5 days, 4 hours to 4 days, 4 hours to 74 hours, 4 hours to 70 hours, 4 hours to 68 hours, 4 hours to 66 hours 4 hours to 64 hours, 4 hours to 64 hours, 4 hours to 60 hours, 4 hours to 58 hours, 4 hours to 56 hours, 4 hours to 54 hours, 4 hours to 54 hours, 4 hours to 50 hours, 4 hours to 48 hours, 4 hours to 46 hours, 4 hours to 44 hours, 4 hours to 40 hours, 4 hours to 38 hours, 4 hours to 36 hours, 4 hours to 34 hours, 4 hours to 34 hours, 4 hours to 30 hours, 4 hours to 28 hours, 4 hours to 26 hours, 4 hours to 24 hours, 4 hours to 24 hours, 4 hours to 20 hours, 4 hours to 18 hours, 4 hours to 16 hours, 4 hours to 14 hours, 4 hours to 14 hours, 4 hours to 10 hours, 4 hours to 8 hours, 4 hours to 6 hours, 6 hours to 35 days, 6 hours to 30 days, 6 hours to 28 days, 6 hours to 26 days, 6 hours to 25 days, 6 hours to 24 days, 6 hours to 22 days, 6 hours to 20 days, 6 hours to 18 days, 6 hours to 16 days, 6 hours to 14 days, 6 hours to 12 days, 6 hours to 10 days, 6 hours to 8 days, 6 hours to 7 days, 6 hours to 6 days, 6 hours to 5 days, 6 hours to 4 days, 6 hours to 76 hours, 6 hours to 70 hours, 6 hours to 68 hours, 6 hours to 66 hours 6 hours to 64 hours, 6 hours to 66 hours, 6 hours to 60 hours, 6 hours to 58 hours, 6 hours to 56 hours, 6 hours to 54 hours, 6 hours to 56 hours, 6 hours to 50 hours, 6 hours to 48 hours, 6 hours to 46 hours, 6 hours to 44 hours, 6 hours to 40 hours, 6 hours to 38 hours, 6 hours to 36 hours, 6 hours to 34 hours, 6 hours to 36 hours, 6 hours to 30 hours, 6 hours to 28 hours, 6 hours to 26 hours, 6 hours to 24 hours, 6 hours to 26 hours, 6 hours to 20 hours, 6 hours to 18 hours, 6 hours to 16 hours, 6 hours to 14 hours, 6 hours to 16 hours, 6 hours to 10 hours, 6 hours to 8 hours, 12 hours to 35 days, 12 hours to 30 days, 12 hours to 28 days, 12 hours to 26 days, 12 hours to 25 days, 12 hours to 24 days, 12 hours to 22 days, 12 hours to 20 days, 12 hours to 18 days, 12 hours to 16 days, 12 hours to 14 days, 12 hours to 12 days, 12 hours to 10 days, 12 hours to 8 days, 12 hours to 7 days, 12 hours to 6 days, 12 hours to 5 days, 12 hours to 4 days, 12 hours to 72 hours, 12 hours to 70 hours, 12 hours to 68 hours, 12 hours to 66 hours 12 hours to 64 hours, 12 hours to 62 hours, 12 hours to 60 hours, 12 hours to 58 hours, 12 hours to 56 hours, 12 hours to 54 hours, 12 hours to 512 hours, 12 hours to 50 hours, 12 hours to 48 hours, 12 hours to 46 hours, 12 hours to 44 hours, 12 hours to 40 hours, 12 hours to 38 hours, 12 hours to 36 hours, 12 hours to 34 hours, 12 hours to 312 hours, 12 hours to 30 hours, 12 hours to 28 hours, 12 hours to 26 hours, 12 hours to 24 hours, 12 hours to 22 hours, 12 hours to 20 hours, 12 hours to 18 hours, 12 hours to 16 hours, 12 hours to 14 hours, 1 day to 35 days, 1 day to 30 days, 1 day to 28 days, 1 day to 26 days, 1 day to 25 days, 1 day to 24 days, 1 day to 22 days, 1 day to 20 days, 1 day to 18 days, 1 day to 16 days, 1 day to 14 days, 1 day to 12 days, 1 day to 10 days, 1 day to 8 days, 1 day to 6 days, 1 day to 5 days, 1 day to 4 days, 1 day to 3 days, 1 day to 2 days, 2 days to 35 days, 2 days to 30 days, 2 days to 28 days, 2 days to 26 days, 2 days to 25 days, 2 days to 24 days, 2 days to 22 days, 2 days to 20 days, 2 days to 18 days, 2 days to 16 days, 2 days to 15 days, 2 days to 14 days, 2 days to 12 days, 2 days to 10 days, 2 days to 8 days, 2 days to 6 days, 2 days to 4 days, 2 days to 3 days, 4 days to 35 days, 4 days to 30 days, 4 days to 28 days, 4 days to 26 days, 4 days to 25 days, 4 days to 24 days, 4 days to 22 days, 4 days to 20 days, 4 days to 18 days, 4 days to 16 days, 4 days to 15 days, 4 days to 14 days, 4 days to 12 days, 4 days to 10 days, 4 days to 8 days, 4 days to 6 days, 7 days to 35 days, 7 days to 30 days, 7 days to 28 days, 7 days to 26 days, 7 days to 25 days, 7 days to 24 days, 7 days to 22 days, 7 days to 20 days, 7 days to 18 days, 7 days to 16 days, 7 days to 15 days, 7 days to 14 days, 7 days to 12 days, 7 days to 10 days, 7 days to 8 days, 14 days to 35 days, 14 days to 30 days, 14 days to 28 days, 14 days to 26 days, 14 days to 25 days, 14 days to 24 days, 14 days to 22 days, 14 days to 20 days, 14 days to 18 days, 14 days to 16 days, 14 days to 15 days, 21 days to 35 days, 21 days to 30 days, 21 days to 28 days, 21 days to 26 days, 21 days to 25 days, 21 days to 24 days, 21 days to 22 days, 28 days to 35 days, or 28 days to 30 days; 1 hour, 2 hours, 4 hours, 6 hours, 8 hours, 10 hours, 12 hours, 14 hours, 16 hours, 18 hours, 20 hours, 22 hours, 24 hours, 2 days, 3 days, 4 days, 5 days, 6 days, 7 days, 8 days, 10 days, 12 days, 14 days, 16 days, 18 days, 20 days, 21 days, 22 days, 24 days, 25 days, 26 days, 28 days, 30 days, 32 days, 34 days or 35 days).

The length of a cycle can be regulated by using strains that lyse at different optical density (ODs). Cell lysis can also be regulated by tuning the internal circuitry of the quorum sensing components, e.g., tuning of AHL degradation, tuning lysis of protein degradation, tuning of promoters to increase or decrease expression of molecules involved in the quorum sensing circuitry.

Various methods known in the art can be used to determine whether the quorum threshold is reached. For example, the quorum threshold can be measured using traditional protein quantification methods to measure the level of AHL expression in the culture medium. The quorum threshold can also be measured using reporter proteins driven by the luxI promoter. In some embodiments, the reporter protein is a fluorescent protein, a bioluminescent luciferase reporter, a secreted blood/serum or urine reporter (e.g., secreted alkaline phosphatase, soluble peptides, Gaussian luciferase).

Various methods are known in the art to determine and/or measure cell lysis. For example, cell lysis can be determined phenotypically using microscopy by the change in intensity of transmitted light and/or absorbance at various wavelengths including 600 nm light. In some embodiments, bacterial cell lysis is synchronized. In other embodiments, bacterial cell lysis is not synchronized. Synchronized lysis can be measured via optical density at 600 nm absorbance (OD600) in a plate reader or other quantitative instruments.

Systems

Provided herein are systems that include a culture of a bacterial strain, wherein the bacterial strain comprises: a first nucleic acid sequence encoding a first activator polypeptide (e.g., any of the first activator polypeptides described herein), wherein expression of the first activator polypeptide results in production of a quorum sensing molecule precursor, wherein the first nucleic acid sequence is operably linked to a promoter; a second nucleic acid sequence encoding a second activator polypeptide (e.g., any of the second activator polypeptides described herein), wherein expression of the second activator polypeptide results in production of a quorum sensing molecule, wherein the second nucleic acid sequence is operably linked to a first activatable promoter; a third nucleic acid sequence encoding a third activator polypeptide (e.g., any of the third activator polypeptides described herein), wherein expression of the third activator polypeptide results in activation of the quorum sensing system, wherein the third nucleic acid sequence is operably linked to a second activatable promoter; and a fourth nucleic acid sequence encoding a gene of interest (e.g., any of the genes of interest described herein), wherein the fourth nucleic acid sequence is operably linked to a third activatable promoter; and an inducer molecule; and a quorum sensing molecule that enables induction of quorum sensing.

Provided herein are systems that can include a co-culture of at least two bacterial strains (e.g., at least three, at least four, at least five, at least six, at least seven, at least eight, at least nine, at least ten, at least eleven, at least twelve, 2, 3, 4, 5, 6, 7, 8, 9, 10, 11, 12), wherein the at least two bacterial strains can include a first bacterial strain having at least a portion of a first synchronized lysis circuit, wherein the first synchronized lysis circuit comprises a first lysis polypeptide and a first activator polypeptide and wherein the first lysis polypeptide is activated by the first activator polypeptide.

In some embodiments described herein, a system comprises a co-culture of at least a first bacterial strain and a second bacterial strain, wherein the first bacterial strain has at least a portion of a first synchronized lysis circuit, wherein the first synchronized lysis circuit comprises a first lysis polypeptide, a first activator polypeptide, and a first polypeptide stabilizing element, and wherein the first lysis polypeptide is activated by the first activator polypeptide, and wherein the second bacterial strain has at least a portion of a second synchronized lysis circuit, wherein the second synchronized lysis circuit comprises a second lysis polypeptide, a second activator polypeptide, and a second polypeptide stabilizing element, and wherein the second lysis polypeptide is activated by the second activator polypeptide, and wherein the first and second synchronized lysis circuits are orthogonal in that each has no or substantially no effect upon the other. As used herein, "substantially no effect" means no measurable effect on the activatable promoter, as measured by the expression of the activatable promotor of a fluorescent protein. In some aspects, the first bacterial strain can include the first lysis polypeptide. In some aspects of any of the systems described herein, the first bacterial strain can include the first activator polypeptide.

In some aspects of any of the systems described herein, the at least two bacterial strains further can include a second bacterial strain.

In some aspects of any of the systems described herein, the second bacterial strain can include the first activator polypeptide.

In some aspects of any of the systems described herein, each of the first bacterial strain and the second bacterial strain can include the first activator polypeptide.

In some aspects of any of the systems described herein, the first lysis polypeptide of the first bacterial strain operates independent of at least one other bacterial strain in the co-culture. In some embodiments, the first lysis polypeptide of the first bacterial strain operates independent of at least the second bacterial strain. In some embodiments, the first lysis polypeptide of the first bacterial strain operates independent of at least one bacterial strain in the system that is not the second bacterial strain.

In some aspects of any of the systems described herein, the first lysis polypeptide of the first bacterial strain responds to a signal generated by at least one other bacterial strain in the co-culture. In some embodiments, the first lysis polypeptide of the first bacterial strain responds to a signal generated by at least the second bacterial strain. In some embodiments, the first lysis polypeptide of the first bacterial strain responds to a signal generated by at least one bacterial strain in the system that is not the second bacterial strain.

In some aspects of any of the systems described herein, the signal is a quorum sensing signal. In some aspects of any of the systems described herein, the first activator polypeptide encodes a quorum sensing signal. In some aspects of any of the systems described herein, the second activator polypeptide encodes a quorum sensing signal. In some embodiments, the quorum sensing signal can be a quorum sensing signaling molecule. In some embodiments, one or more of the bacterial strains respond to a quorum sensing signal. In some embodiments, the quorum sensing signals for two or more of the bacterial strains are different quorum sensing signals. In some embodiments, the quorum sensing signals for two or more of the bacterial strains are the same quorum sensing signals.

In some embodiments, the quorum sensing signaling molecule for the first and second synchronized lysis circuits are orthogonal in that each has no measurable effect upon the other.

In some aspects of any of the systems described herein, the second bacterial strain has at least a portion of a second synchronized lysis circuit, wherein the second synchronized lysis circuit comprises a second lysis polypeptide and a second activator polypeptide. In some aspects of any of the systems described herein, the second bacterial strain comprises the second lysis polypeptide.

In some aspects of any of the systems described herein, second bacterial strain comprises the second activator polypeptide.

In some aspects of any of the systems described herein, the first bacterial strain comprises the second activator polypeptide.

In some aspects of any of the systems described herein, the second lysis polypeptide of the second bacterial strain operates independent of at least the first bacterial strain.

In some aspects of any of the systems described herein, the second lysis polypeptide of the second bacterial strain responds to a signal generated by the first bacterial strain.

In some aspects of any of the systems described herein, at least one of the at least two bacterial strains (e.g., at least one of a first bacterial strain and a second bacterial strain) has a growth advantage compared to at least one other bacterial strain. In some embodiments, at least the first bacterial strain has a growth advantage compared to at least the second bacterial strain. In some embodiments, at least the second bacterial strain has a growth advantage compared to at least the first bacterial strain. In some embodiments, at least the first bacterial strain has a growth advantage compared to a bacterial strain present in the system that is not the second bacterial strain. In some embodiments, at least the second bacterial strain has a growth advantage compared to a bacterial strain present in the system that is not the first bacterial strain. In some embodiments, the system can contain multiple orthogonal co-lysis circuits. For example, a system described herein could include a first co-lysis circuit comprising a first bacterial strain and a second bacterial strain as described herein, as well as a second co-lysis circuit comprising a third bacterial strain and a fourth bacterial strain. In some embodiments, the third and fourth bacterial strains each comprise a lysis polypeptide having a lysis gene under the control of an activatable promoter; and an activator polypeptide having an activator gene, the expression of which promotes the accumulation of a quorum sensing molecule, wherein both the activatable promoter of the lysis gene and the expression of the activator gene is activated by the quorum sensing molecule, wherein the quorum-sensing molecule of the third strain is different from the quorum-sensing molecule of the fourth strain, and wherein each quorum-sensing molecule of the third and fourth strains has no or substantially no effect on the activatable promoter of the lysis gene of the other strain. In some embodiments, the third and fourth bacterial strains can be described in the same manner that the first and second bacterial strains have been described herein. In some embodiments, a system described herein can contain 3, 4, 5, 6, 7, 8, 9, 10, or more co-lysis circuits.

In some aspects of any of the systems described herein, the first bacterial strain is competitive with at least one other bacterial strain in the co-culture. In some embodiments, the first bacterial strain is competitive with at least the second bacterial strain in the co-culture. In some embodiments, the first bacterial strain is competitive with at least one other bacterial strain in the co-culture that is not the second bacterial strain.

In some aspects of any of the systems described herein, the co-culture is stable for at least 48 hours.

In some aspects of any of the systems described herein, the at least two bacterial strains (e.g., at least a first bacterial strain and a second bacterial strain) do not comprise engineered positive or negative interactions between each other.

In some aspects of any of the systems described herein, at least one of the at least two bacterial strains (e.g., at least one of a first bacterial strain and a second bacterial strain) dynamically controls its population without exogenous input.

In some aspects of any of the systems described herein, each of at least two of the at least two bacterial strains (e.g., each of at least a first bacterial strain and a second bacterial strain) dynamically controls its own population without exogenous input.

In some aspects of any of the systems described herein, the system can further include one or more polypeptide stabilizing elements. In some aspects of any of the systems described herein, the polypeptide stabilizing element is selected from a toxin/antitoxin system and an actin-like protein partitioning system.

In some aspects of any of the systems described herein, the first activator polypeptide encodes a degradation tagging sequence.

In some aspects of any of the systems described herein, the second activator polypeptide encodes a degradation tagging sequence.

In some aspects of any of the systems described herein, the first activator polypeptide encodes an N-acyl homoserine lactone.

Compositions and Kits

Also provided herein are compositions (e.g., pharmaceutical compositions) that include any of the bacterial strains described herein (e.g., any of the bacterial strains including any on the nucleic acid sequences described herein). Any of the pharmaceutical compositions can include any of the bacterial strains described herein and one or more (e.g., 1, 2, 3, 4, or 5) pharmaceutically or physiologically acceptable carriers, diluents, or excipients. In some embodiments, any of the pharmaceutical compositions described herein can include one or more buffers (e.g., a neutral-buffered saline, a phosphate-buffered saline (PBS)), one or more carbohydrates (e.g., glucose, mannose, sucrose, dextran, or mannitol), one or more proteins, polypeptides, or amino acids (e.g., glycine), one or more antioxidants, one or more chelating agents (e.g., glutathione or EDTA), one or more preservatives, and/or a pharmaceutically acceptable carrier (e.g., PBS, saline, or bacteriostatic water).

Also provided are kits that include any of the compositions (e.g., pharmaceutical compositions) described herein. In some embodiments, a kit can include a solid composition (e.g., a lyophilized composition including any of the bacterial strains described herein) and a liquid for solubilizing the lyophilized composition.

In some embodiments, the kit includes a vial including any of the pharmaceutical compositions described herein (e.g., formulated as an aqueous pharmaceutical composition). In some embodiments, the kit can include instructions for performing any of the methods described herein.

Methods of Controlling Population Levels

Also provided herein are methods for controlling population density using any of the inducible quorum sensing systems described herein. In some embodiments, the concentration of p-coumaric acid (pCA) added to induce quorum sensing results in sustained population density. In some embodiments, the concentrations of pCA added to induce quorum sensing results in oscillation of population density. In some embodiments, the inducible quorum sensing system includes activation of a lysis gene, where activation of the lysis gene results in reduction in one or more of the bacterial strains.

In some embodiments, the method for controlling population density using any of the inducible quorum sensing systems includes contacting the one or more bacterial strains with the inducer molecule (e.g., pCA) and reducing the level of one or more of the bacterial strains by about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or 100% of the total population of bacteria in the culture as compared to a bacterial culture including one or more of the bacterial strains described herein not contacted with the inducer molecule (e.g., pCA).

Also provided herein are methods for controlling cargo release using any of the inducible quorum sensing systems described herein. In some embodiments, the inducible quorum sensing includes activation of a lysis gene, wherein activation of the lysis gene results in controlled release of cargo. In some embodiments, controlled release of cargo can control population density.

Methods of Treatment

Also provided herein are methods for treating a disease by administering to the subject a therapeutically effective amount of any of the bacterial strains described herein, or any of the pharmaceutical compositions described herein. Additional non-limiting aspects of the bacterial strains, pharmaceutical compositions, kits, and methods are described herein and can be used in any combination without limitation.

In some embodiments of any of the methods described herein, the subject has a cancer or an infection. In some embodiments wherein the subject has a cancer, the cancer can be, e.g., a primary tumor, or a metastatic tumor. In some embodiments, the cancer is a non-T-cell-infiltrating tumor. In some embodiments of any of the methods described herein, the cancer is selected from the group consisting of: glioblastoma, squamous cell carcinoma, breast cancer, colon cancer, hepatocellular cancer, melanoma, neuroblastoma, pancreatic cancer, and prostate cancer. Treatment of multiple cancer types at the same time is contemplated by and within the present disclosure.

In some instances, the subject having the cancer may have previously received cancer treatment (e.g., any of the cancer treatments described herein).

Without further description, it is believed that one of ordinary skill in the art can, using the preceding description and the following illustrative examples, make and utilize the bacterial strains of the present disclosure and practice the claimed methods. The following working examples specifically point out various aspects of the present disclosure, and are not to be construed as limiting in any way the remainder of the disclosure.

EXAMPLES

Example 1. Design and Characterization of the Inducible Quorum Sensing System (iQS)

To design an exemplary iQS system, the two-step pathway which converts pCA into p-coumaroyl-HSL (pC-HSL) was genetically reconstructed through the production of the intermediate molecule p-coumaroyl-CoA (FIG. 1A). The first conversion is catalyzed by the p-coumaric acid-CoA ligase encoded by the 4CL2nt gene from the plant *Nicotiana tabacum* while the second step is catalyzed by the RpaI synthase. Additionally, superfolder green fluorescent protein (sfGFP) was added to be able to monitor the inducible dynamics. In some cases, all genes, with the exception of 4CL2nt, are driven by the luxI quorum sensing promoter, which has been shown to perform better than the native promoter of *R. palustris* when heterologously expressed. *Escherichia Coli* was chosen as the host chassis for the double plasmid circuit. The methods described in Example 1 are also applicable to Examples 2, 3, and 4.

Plasmids and Strains

The iSLC and SLC strains were both cultured in lysogeny broth (LB) media with 50 µg mL$^{-1}$ kanamycin, 34 µg mL$^{-1}$ chloramphenicol and 0.2% glucose for strains containing ColE1 origin and p15A origin plasmids in a 37° C. shaking incubator. Plasmid pTD103 RpaR-RpaI-LAA-sfGFP[21], ptD103-CFP were constructed by as described in previous studies (see, e.g., FIG. 11). Both plasmids pAM014 and pAM021 were obtained by inserting the 4CL2nt gene under the constitutive promoter J23106 from the Anderson promoter library. The 4CL2nt gene and the promoter were synthesized with overlapping PCR of long oligonucleotides (IDT). All plasmids were constructed by Gibson assembly followed by transformation into DH5α (Thermofisher) chemically competent E. coli. All plasmids were verified by Sanger sequencing before transformation into E. coli strain MG1655.

Microfluidics and Microscopy

The microscopy and microfluidics techniques used are similar to those previously reported. The microfluidic devices were constructed from PDMS (polydimethylsiloxane), which was molded and baked on a silicon wafer with micronscale features formed by crosslinked photoresist. Once the PDMS hardened, it was peeled off, and individual devices were cut out. In order to connect fluid lines to the device, holes where punched in correspondence of the inlets and outlets of the device. Afterwards, the devices were bonded onto glass slides using plasma activation. Before each experiment, the devices were left for 30 minutes in a vacuum chamber. Meanwhile, 1 mL of overnight cell culture was spun down by centrifugation and re-suspended in 10 μL of fresh media with appropriate antibiotics. After taking the device out of the vacuum chamber, a single droplet of resuspended cells was positioned in correspondence of the outlet opening. Similarly, droplets of sterile fresh media were placed in correspondence of the inlets openings. In all cases, 0.075% Tween20 was added to the medium to prevent cells from sticking to the PDMS walls. After all chip features were wetted, the fluids lines were plugged in and the height of the inlet was raised 10 to 40 cm above the device. The outlet syringe was instead placed at the same height of the device. For co-culturing experiments in FIG. 4, cells were cultured individually overnight and eventually spun down and re-suspended together (1:1 ratio) allowing for a single droplet to be loaded on the device. All experiments shown in FIG. 2 and FIG. 4 were performed in a sidetrap array device with bacteria growth chambers approximately 100×80 μm in area and approximately 1.2 μm in height. The upstream channels consists of a series of dividing serpentine which allow for sequential dilutions of the two input media, generating a gradient of eight different inducer concentrations. For the kill switch experiments, reported in FIG. 3, a simpler device was used with a single input and an ordered array of traps. The dimensions of the traps are the same as the ones described for the gradient device. Experiments in FIG. 2 and FIG. 4 where carried out by connecting a syringe with LB+antibiotics+0.075% Tween20 as inlet 1 and a syringe with LB+antibiotics+0.075% Tween20+1 μM of p-coumaric acid as inlet 2. P-coumaric acid inductions for microfluidic experiments in FIG. 3B were performed by unplugging the syringe with pure media and substituting it with a second syringe containing media plus the appropriate p-coumaric acid concentration. For microscopy, the same system was used as described in previous studies. In brief, images were acquired with a Nikon TI2 using a Photometrics CoolSnap cooled CCD camera. The scope and accessories were programmed using the Nikon Elements software. The microscope was housed in a plexiglass incubation chamber maintained at 37° C. by a heating unit. Phase-contrast images were taken at 4× and 10× magnification at 50-100 us exposure times. At 4× magnification fluorescence exposure times were 2 seconds at 30% intensity for both gfp and cfp while at 10× magnification they were 200 us at 30% intensity for both GFP and CFP. Images were taken every 6 minutes for each experiment. For induction experiments, imaging was paused while syringes were swapped.

Data Analysis

Fluorescence intensity profiles were obtained by analyzing frames from the fluorescent channels. The mean fluorescence values were calculated by drawing a rectangle surrounding each trap individually and extracting the z-axis profile on ImageJ. Fluorescence values shown in FIG. 2 were normalized by dividing all data by a constant factor. In addition, the subset of traps for each column was normalized by subtracting the minimum value among the traps in the subset. Transmitted light data from FIG. 3B was normalized by subtracting the minimum value for each time trace. Fluorescence data shown in FIG. 4 was normalized by first dividing the subsets of traps by their overall maximum values and subsequently subtracting the respective minimum values. In addition, the data in FIG. 4 was smoothed with the command smoothdata( ) in Matlab. Heatmaps were generated in Matlab using the function heatmap( ). For the co-culture experiments, when overlap between the gfp and cfp channels was observed, values were corrected taking into consideration the image frames in order to subtract overlapping signal.

Plate Reader Experiments

For plate reader experiments, the appropriate strains were seeded from a −80° C. glycerol stock into 3 ml LB with 0.2% glucose and appropriate antibiotics and incubated in a 37° C. shaking incubator. The following day, 2 μL of overnight culture were added to 200 μL fresh media containing appropriate antibiotics in a standard Falcon tissue culture 96-well flat bottom plate. Cells were incubated at 37° C. shaking in a Tecan Infinite M200 Pro. Cells were grown for about 12 hours. The optical density at 600 nm absorbance was measured every 10 minutes.

Cells Survival Assay

Cell viability assays to test the efficacy of iQS as a kill switch were done by measuring colony forming units (CFUs), following a protocol found in the literature. Cells were grown under survival conditions in LB with 0.2% glucose which inhibits the LuxI promoter thanks to the presence of a binding site for the CAP-CAMP activating complex. Following overnight growth, they were transferred into four cultures of fresh LB medium with 0.2% glucose, 300 nM p-coumaric acid, 500 nM p-coumaric acid and 1 μM p-coumaric acid, respectively. Samples were collected every 2 hours and serially diluted in PBS over a 7-log range and spotted (2 μL) onto LB agar plates with 0.2% glucose. The equations used arc: CFU/ml=(number of colonies)×(dilution factor)/0.002 mL, survival ratio (log 10)=log (CFU/ml with glucose)/(CFU/ml with p-coumaric acid).

Results

Figure 1B:
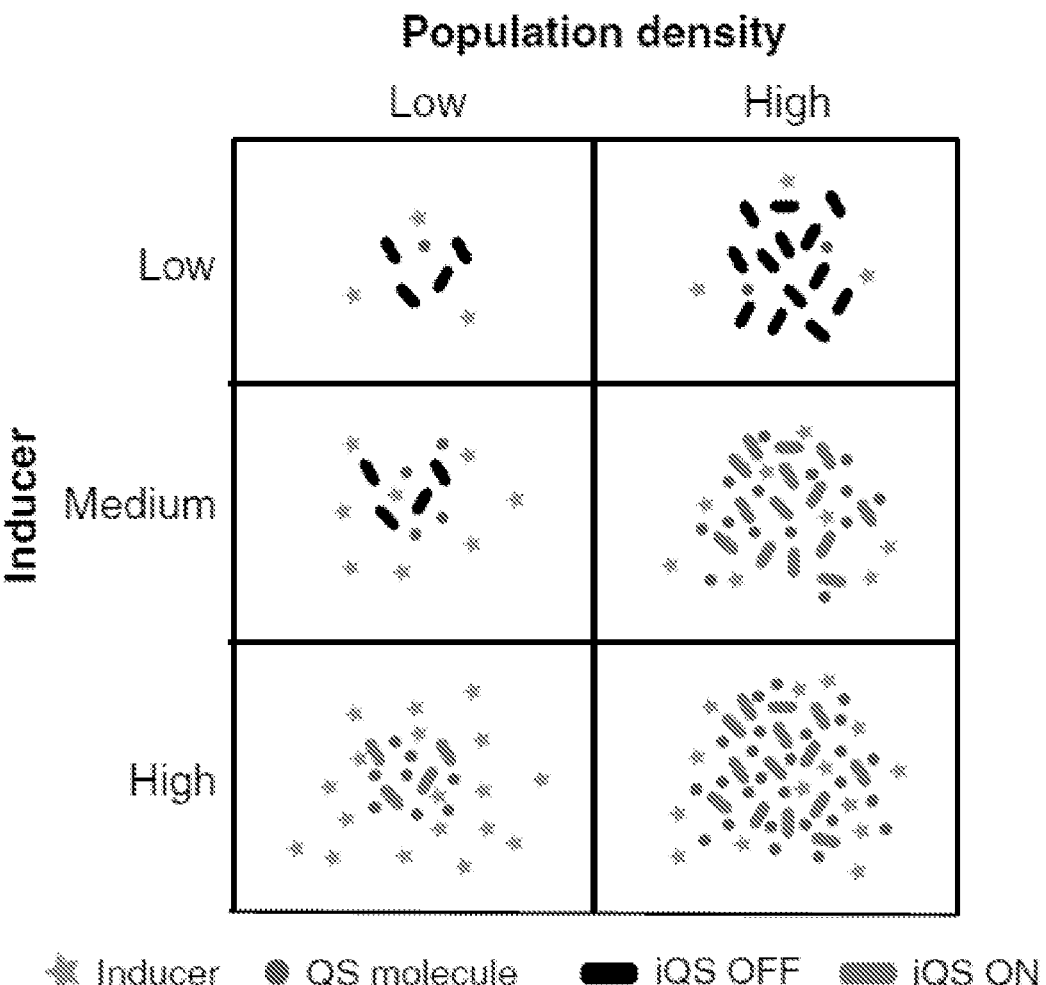
FIG. 1B shows a schematic diagram to illustrate predicted dynamics associated to the inducible quorum sensing system as a function of population density and external inducer concentration.
Figure 1C:
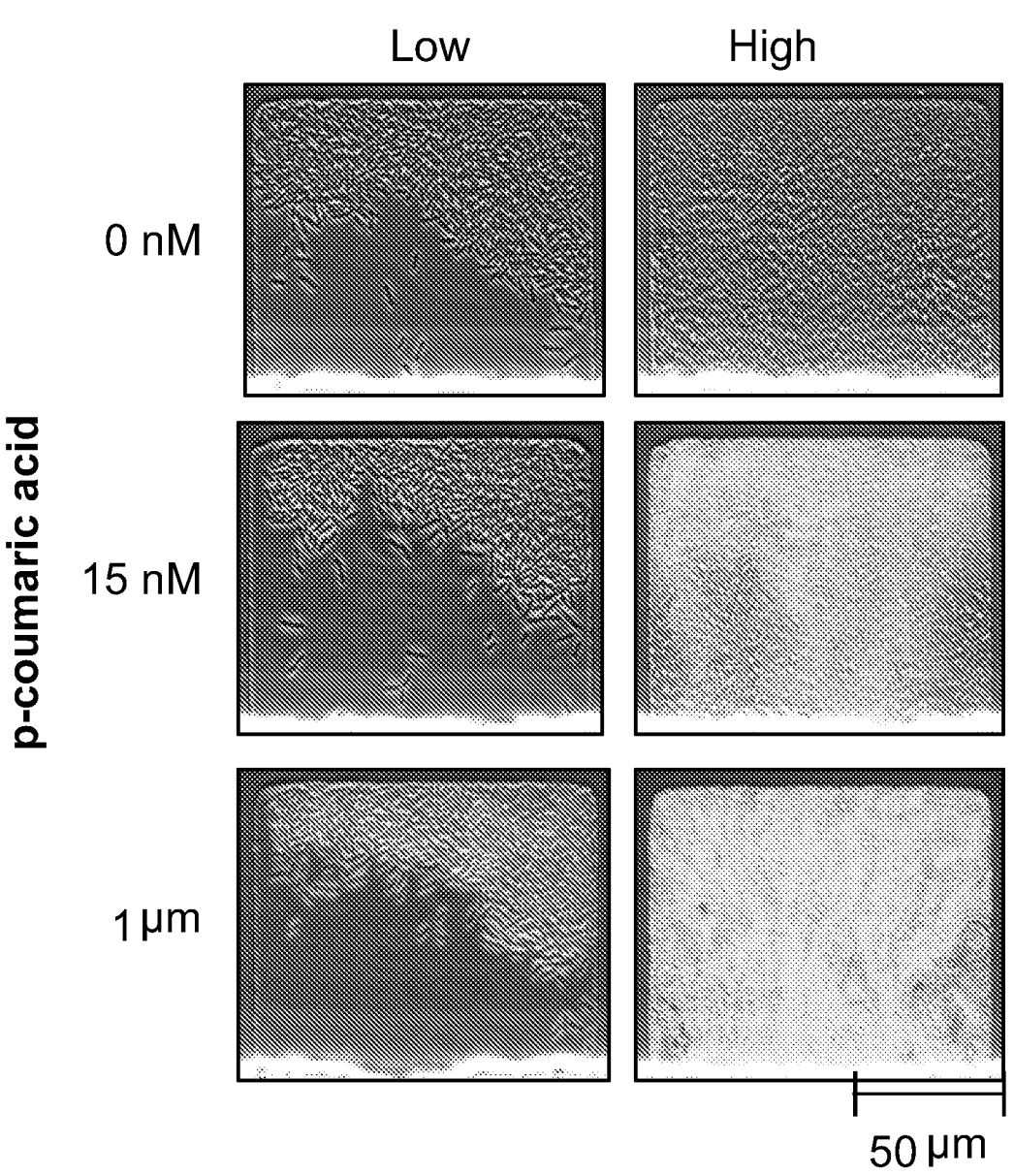
FIG. 1C shows fluorescence microscopy images showing a composite of phase-contrast and GFP fluorescence in microfluidic traps. The data from the raw fluorescence values reflect the iQS dynamics predicted in FIG. 1B.
Figure 1D:
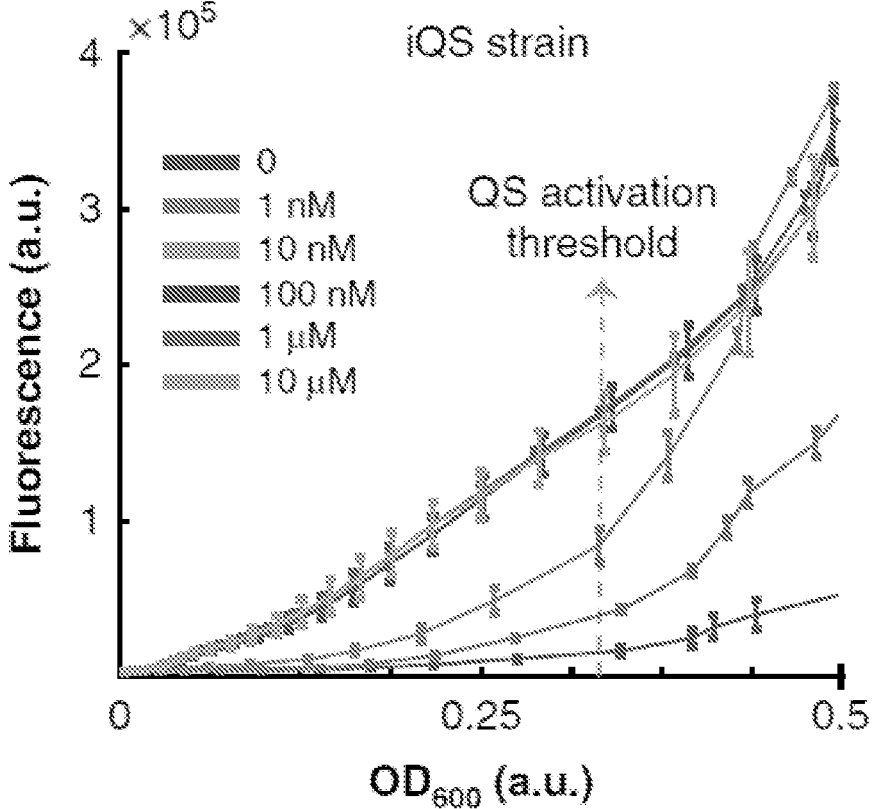
FIG. 1D shows data from microplate reader experiment obtained by culturing the iQS strain in different p-coumaric acid concentrations. All data points represent mean standard deviation of three independent replicates.
Figure 1E:
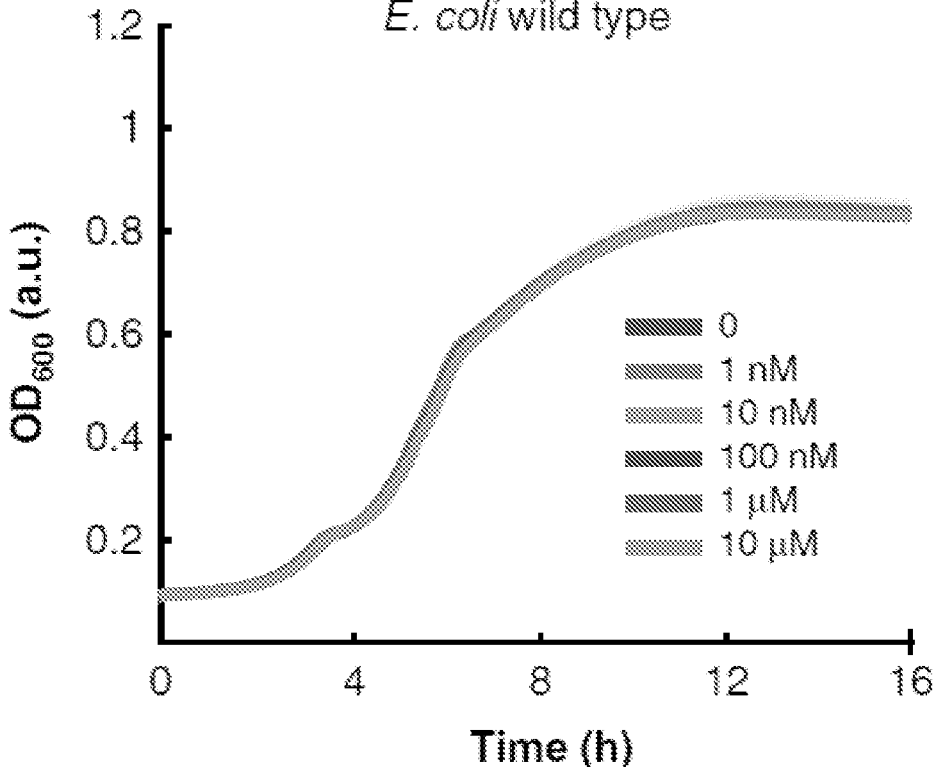
FIG. 1E shows microplate reader experiment data obtained by culturing the wild type *E. coli* strain in a range p-coumaric acid concentrations. All data points represent mean (solid line) standard deviation of three independent replicates (shaded areas).

Predictions were formulated that inducibility would expand the range of population dynamics by including an 'OFF' state at low inducer concentration and an 'ON' state at high inducer concentrations which are both independent of population density. On the other hand, for a range of intermediate concentrations the iQS would behave like a standard QS system by exhibiting the typical population density dependent activation (FIG. 1B). To investigate how the engineered iQS strain would relate to these expected dynamics, microfluidic devices were used, which enabled the simultaneous exposure of varying pCA concentrations to different subgroups of cells. Time-lapse fluorescence microscopy was used to observe fluorescence expression as a function of population size and inducer concentration. The data matched the expected dynamics of an inducible quorum sensing system when exposed to zero, medium (15 nM) or high (1 μM) inducer concentrations (FIG. 1C). Additionally, further characterization of the iQS response over a broader range of pCA concentrations was performed using a microwell plate reader. A concentration of zero of the inducer molecule resulted in the circuit being OFF except for a baseline of leaky expression. Intermediate levels (1 nM and 10 nM) induced the typical population-dependent switch-like behavior with a steep increase in fluorescence signal at an optical density threshold of around 0.3. Finally, high concentrations (100 nM to 10 μM) resulted in a linear relationship between fluorescence expression and population density, confirming the assumption of a population independent 'ON' state (FIG. 1D). As a control, the same experiment was repeated with a wild type E. *Coli* strain and observed that the growth curves were unaffected, confirming pCA is not toxic within the characterized range (FIG. 1E).

Example 2. Characterization of the Inducible Synchronized Lysis Circuit (iSLC)

Figure 2A:
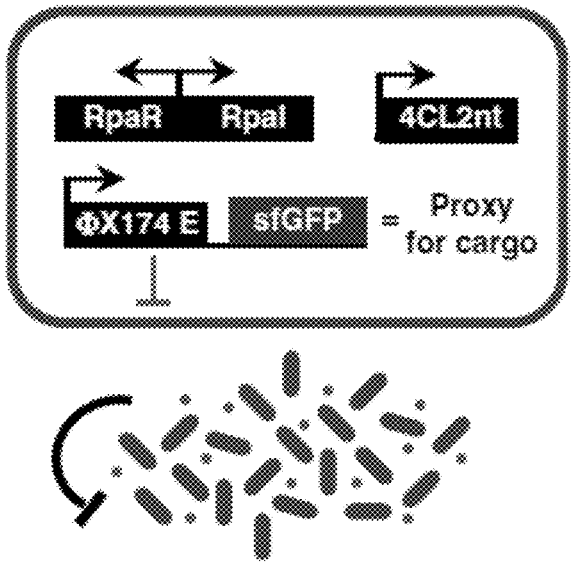
FIG. 2A shows schematic diagram illustrating the components of the iSLC strain.

To demonstrate the usefulness of the iQS over non-inducible quorum sensing based circuits, the iQS was coupled with the expression of a lysis gene to create a platform for inducible population dependent bacterial cargo delivery (FIG. 2A). To qualitatively predict the dynamics of this iSLC strain (induced synchronized lysis circuit), a deterministic model was developed as described below, which is also applicable to Examples 1, 3, and 4.

Modeling

A deterministic model was constructed to qualitatively describe the dynamic behavior of the iSLC strain. The model is based on a set of six ODEs (ordinary differential equation) which track the evolution of the following six variables: the cell number into a single microfluidic trap (N), the external concentration of p-coumaroyl-HSL (pH), the intracellular concentration of lysis protein (L), the intracellular concentration of the variable RpaI (I), the intracellular concentration of 4CL2nt enzyme (E) and the intracellular concentration of the intermediate compound p-coumaroyl-CoA (pA). The inducer concentration is kept fixed for each simulation and it is defined together with the initial conditions.

Figure 12:
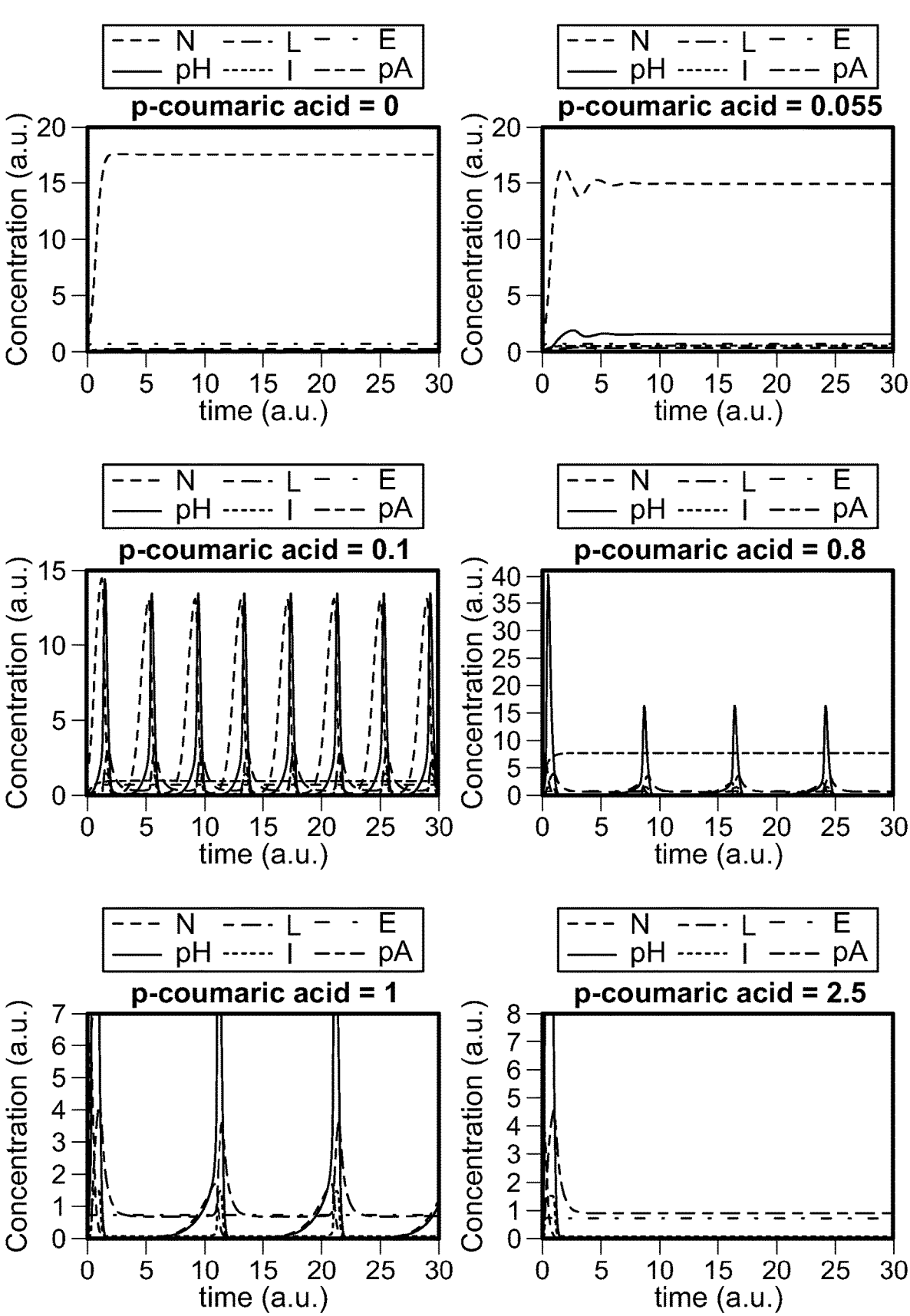
FIG. 12 shows simulation of the evolution of all six variables over time. Six pcoumaric acid concentrations are considered to span the emerging population dynamics. Initially, all the variables are set to zero except cell number (N) which is set to 1.
Figure 13:
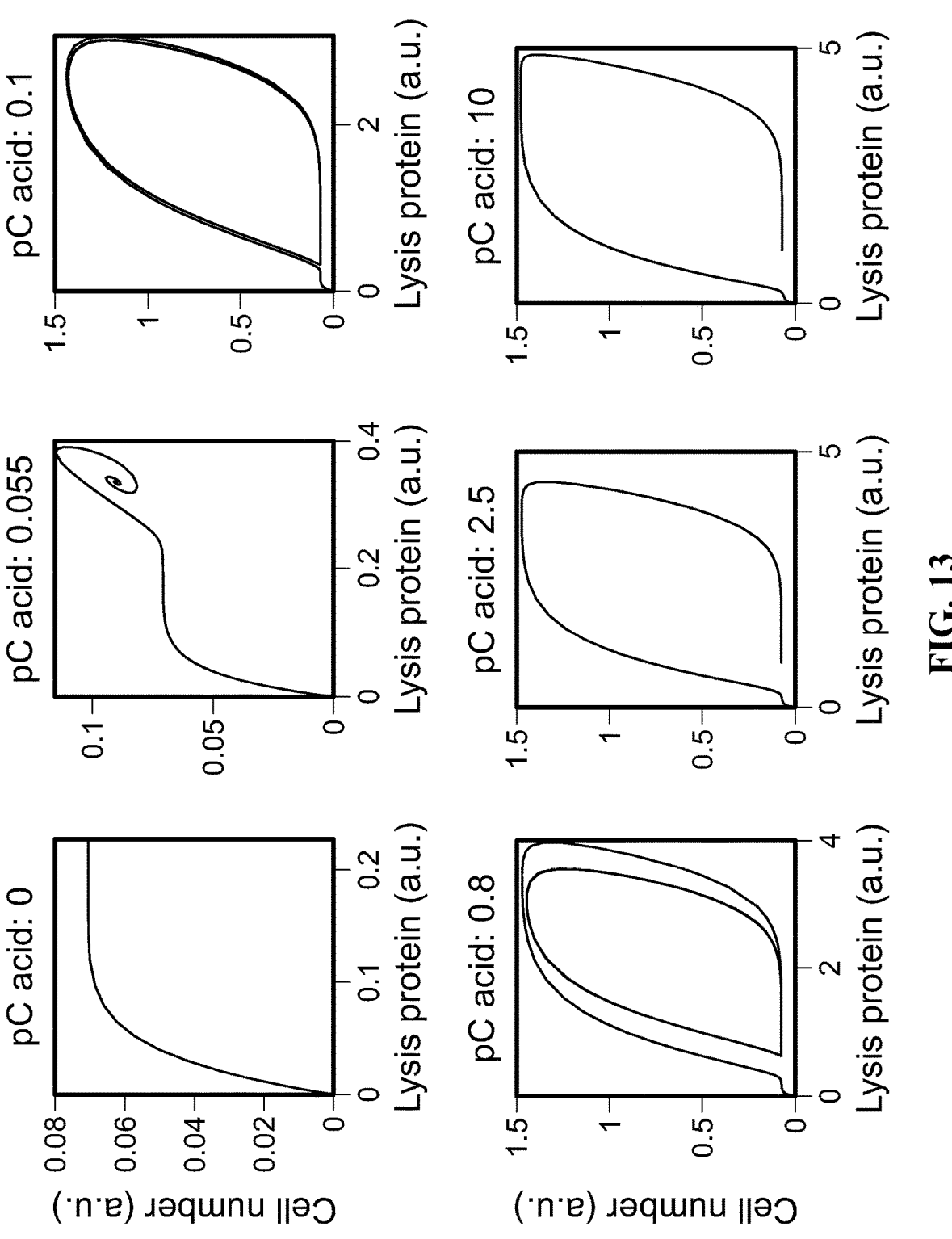
FIG. 13 shows phase portraits of variables N (cell number) and L (lysis protein) showing a Hopf bifurcation caused by the appearance and disappearance of a limit cycle.

A non-zero p-coumaric acid concentration induces the production of the intermediate molecule p-coumaroyl-CoA (pA) through the enzyme 4CL2nt (E). The production term of the latter is a constant variable due to the constitutive promoter which drives it. The intermediate product (pA) is transformed into the quorum sensing molecule pC-HSL through the RpaI enzyme (I). Once a threshold value of extracellular pC-HSL is reached, the intracellular production of the luxI driven genes (RpaI, RpaR and E) are brought to the ON state, thanks to the positive feedback provided by the QS promoter. Activation of the promoter also leads to cell killing as a consequence of the lysis gene expression. The assumption is that the quorum sensing molecule diffuses quickly through the membrane, therefore there is distinguishing between intracellular and extracellular HSL concentration. In addition, the assumption is made that the RpaR-pC-HSL binding is instantaneous, so that the model can be simplified by ignoring the dynamics of the binding complex. Degradation of all proteins (L, I, E) is associated to dilution due to cell growth (μG) as well as basal intracellular degradation (γL and γI). In addition to those terms, RpaI (I) is also actively degraded by ClpXP proteases (γC). Overall, the model can accurately predict the three main dynamics of the cell population as the inducer concentration is varied. With zero inducer concentration, the population grows reaching a steady state value. At very small inducer concentrations, the population undergoes small amplitude lysis events followed by steady state. A finite range of intermediate inducer values was observed which resulted in sustained oscillations of population density. Finally, total population death was observed with no survivors for high concentrations (FIG. 12). Furthermore, visualization of the non-linear dynamics of the system was performed using phase portraits obtained by plotting N (cell number) against L (lysis protein) (FIG. 13). As the p-coumaric acid concentration is increased, the simulations show a first transition from a stable spiral to a limit cycle which indicates sustained oscillations. A further increase in the inducer parameter causes the limit cycle to disappear in favor of a stable fixed point. All plots are generated in MATLAB.

$$\frac{dN}{dt} = \mu G * N * (N_0 - N) - N * \frac{k * L^n}{(L_0)^n + L^n} \tag{1}$$

$$\frac{dpA}{dt} = \mu_4 * inducer * E - \gamma CoA * pA - \mu G * pA \tag{2}$$

$$\frac{dpH}{dt} = \mu_H * N * I * pA - \frac{u * pH}{1 + \frac{N}{N_0}} \tag{3}$$

$$\frac{dL}{dt} = C_i * \left( \alpha_0 + \frac{\alpha_H * \left( \frac{pH}{H_0} \right)^4}{1 + \left( \frac{pH}{H_0} \right)^4} \right) - \gamma_L * L - \mu G * L \tag{4}$$

$$\frac{dI}{dt} = C_i * \left( \alpha_0 + \frac{\alpha_H * \left( \frac{pH}{H_0} \right)^4}{1 + \left( \frac{pH}{H_0} \right)^4} \right) - \gamma_I * I - \mu_G * I \tag{5}$$

$$\frac{dE}{dt} = C_l * P_{const} - \gamma_4 * E - \mu G * E - \gamma_C * E \tag{6}$$

Model parameters were based on a similar model previously published. Compared to the previously used lux quorum sensing system, the iSLC showed higher promoter leakiness which was taken into account by increasing the basal production term (α0). The parameter values used in the model are μG=0.2 (dilution due to cell growth), N0=20 (cell capacity of a single trap), k=10 (maximum rate of cell lysis), L0=1 (concentration of lysis protein resulting in half maximum lysis), n=2 (Hill's coefficient), Cl=0.5 (copy number of the lysis gene), Ci=1 (RpaI gene copy number), Pconst=20 (strength constitutive promoter driving gene 4CL2nt), γ4=2 (degradation of enzyme 4CL2nt), α0=1 (pLux basal leakiness), αH=20 (Lux promoter RpaR-pC-HSL induced production), H0=4.5 (pC-HSL-RpaR binding affinity to pLux), γL=2 (lysis protein basal degradation), γI=2 (RpaI protein basal degradation), γC=12 (pal protein degradation due to ClpXP), γCoA=2 (p-coumaroyl-CoA basal degradation), μ4=30 (con-version rate of p-coumaric acid into p-coumaroyl-CoA), pH=15 (pC-HSL production rate) and μ=12 (maximum AHL clearance rate due to flow).

Results

Figure 2B:
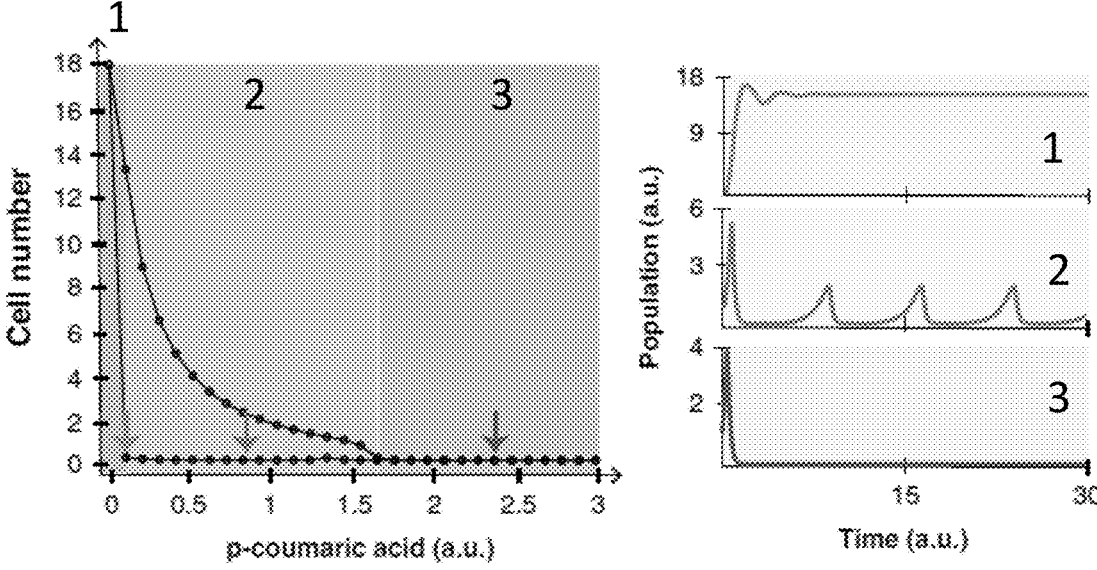
FIG. 2B shows simulations of the mathematical model showing three different dynamics at low (shading associated with numeral 1), medium (shading associated with numeral 2) and high (shading associated with numeral 3) inducer values. Medium values are predicted to result in sustained oscillations. Left panel: steady state maximum and minimum cell population values are plotted for a range of inducer concentrations. Right panel: simulated time traces for three representative p-coumaric acid values predict three emergent population dynamics.
Figure 2C:
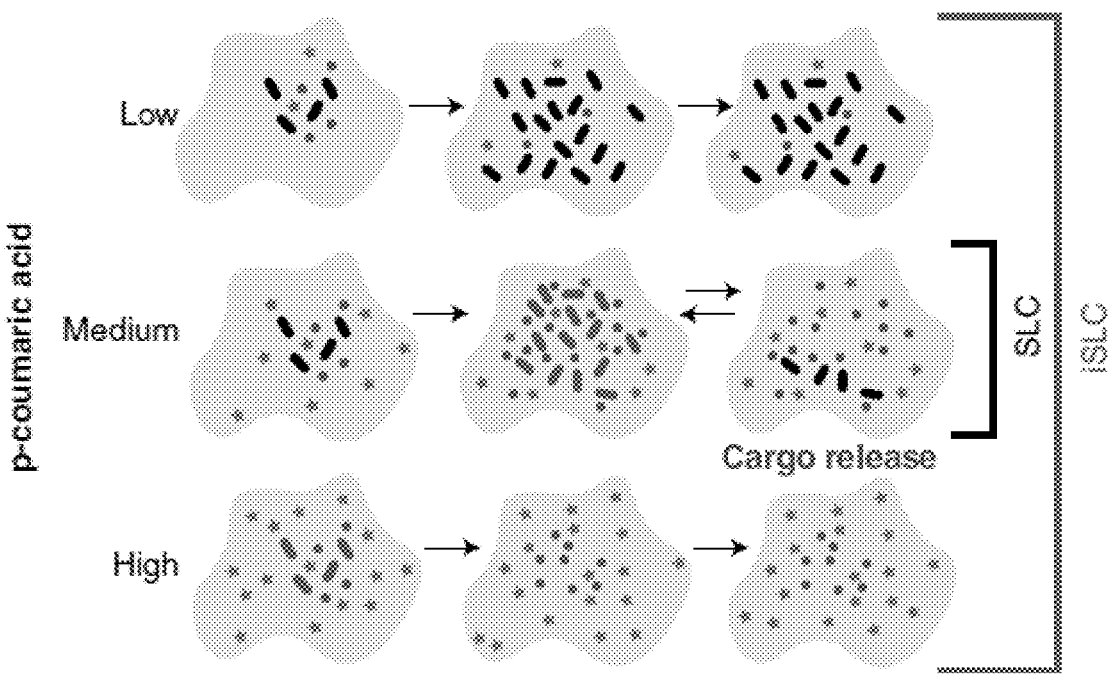
FIG. 2C shows comparison between the iSLC and SLC dynamics based upon the model simulations.

A bifurcation plot was obtained by simulating the steady state values of cell population as a function of pCA concentration, predicting the emergence of three main population regimes (FIG. 2B). Small amplitude lysis events followed by steady growth are predicted at low inducer concentrations. Intermediate pCA concentrations result in sustained oscillations in population density. Finally, high inducer concentrations lead to a single lysis event with zero survivors. Therefore, the iSLC was expected to considerably expand the range of possible population dynamics by adding a quiescent state of circuit inactivation and a termination state in which all cells undergo lysis, regardless of population density (FIG. 2C).

Figure 2D:
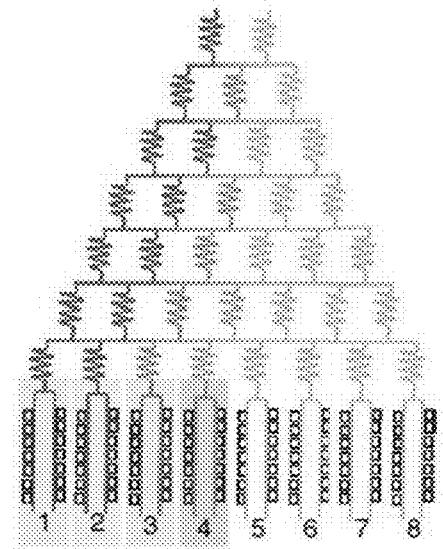
FIG. 2D shows a diagram of the microfluidic device used to generate the inducer gradient.
Figure 2E:
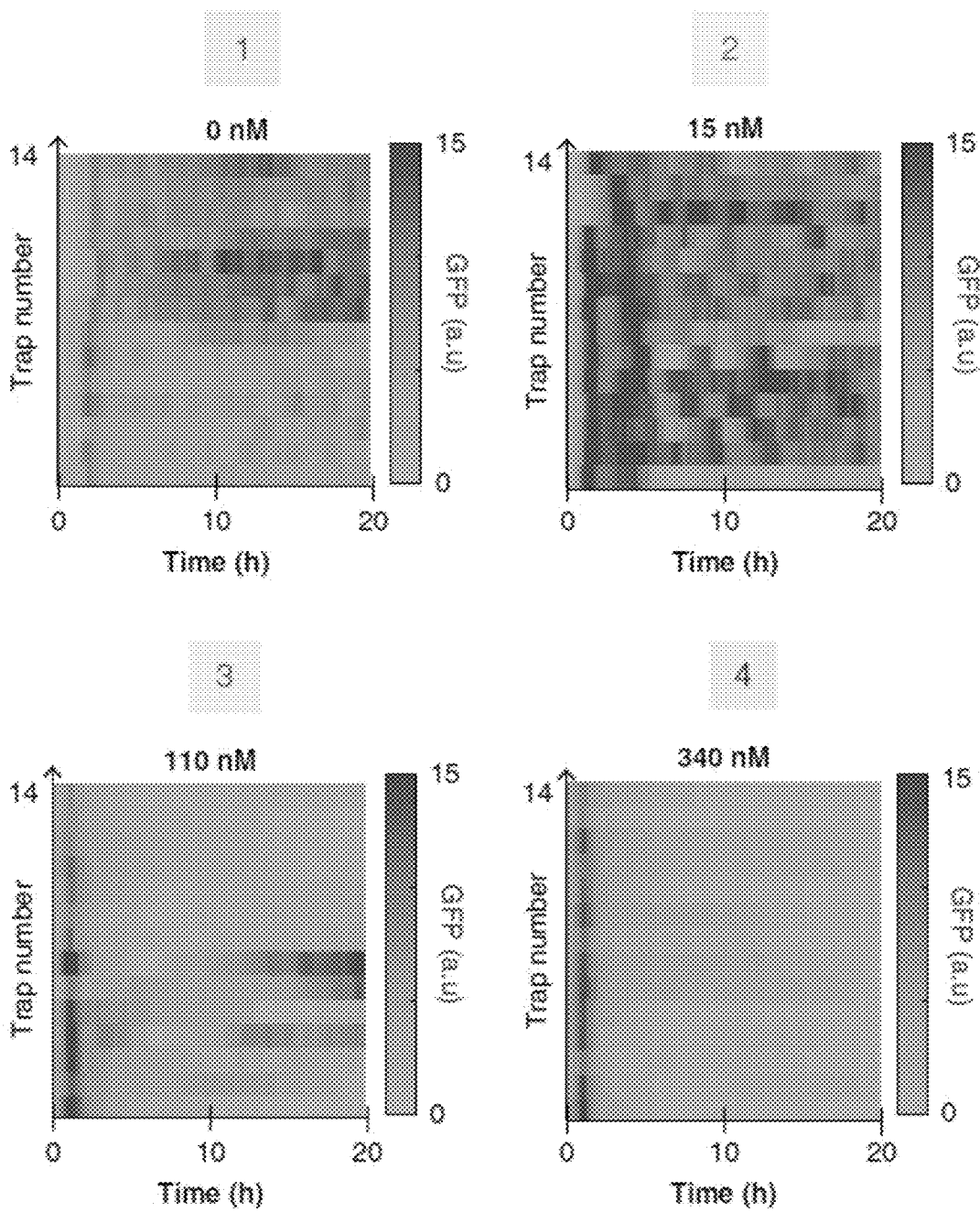
FIG. 2E shows heatmaps representing the fluorescence time traces of all fourteen traps present per column of the device. GFP signal is used as a proxy for population density. Four different inducer conditions are shown: low (1), medium (2), high (3), extra high (4), respectively.
Figure 2F:
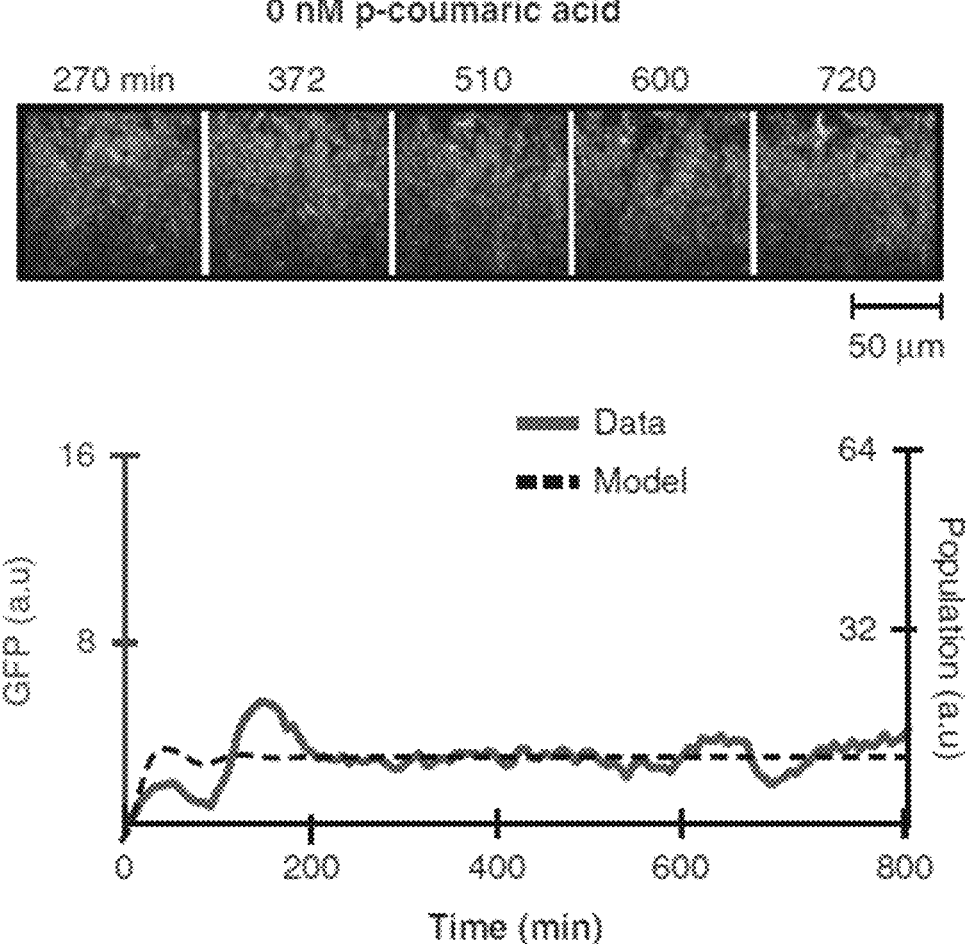
FIG. 2F shows a representative time series images from the fluorescence channel (top panel) and fluorescence time traces plotted together with computer simulations of the mathematical model (bottom panel) a low inducer concentration of 0 nM. For the simulation (dashed) time units are arbitrary, therefore the correspondence is strictly qualitative.
Figure 2G:
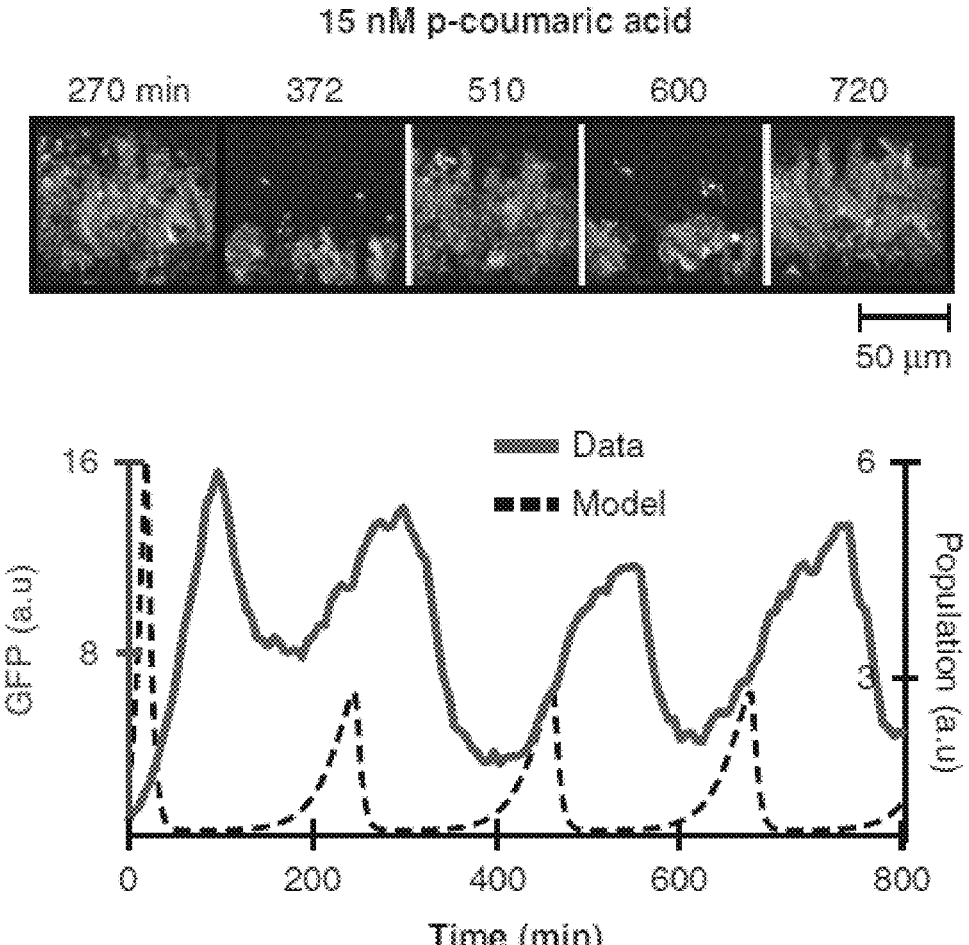
FIG. 2G shows a representative time series images from the fluorescence channel (top panel) and fluorescence time traces plotted together with computer simulations of the mathematical model (bottom panel) with a medium inducer population of 15 nM. For the simulation (dashed) time units are arbitrary, therefore the correspondence is strictly qualitative.
Figure 2H:
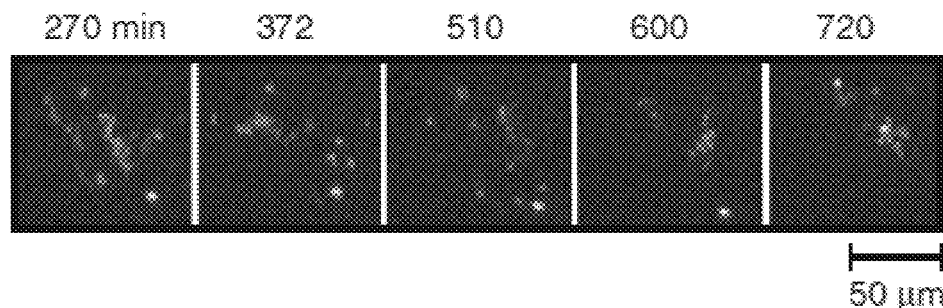
FIG. 2H shows a representative time series images from the fluorescence channel (top panel) and fluorescence time traces plotted together with computer simulations of the mathematical model (bottom panel) with a high inducer population of 110 nM. For the simulation (dashed) time units are arbitrary, therefore the correspondence is strictly qualitative.
Figure 2H:
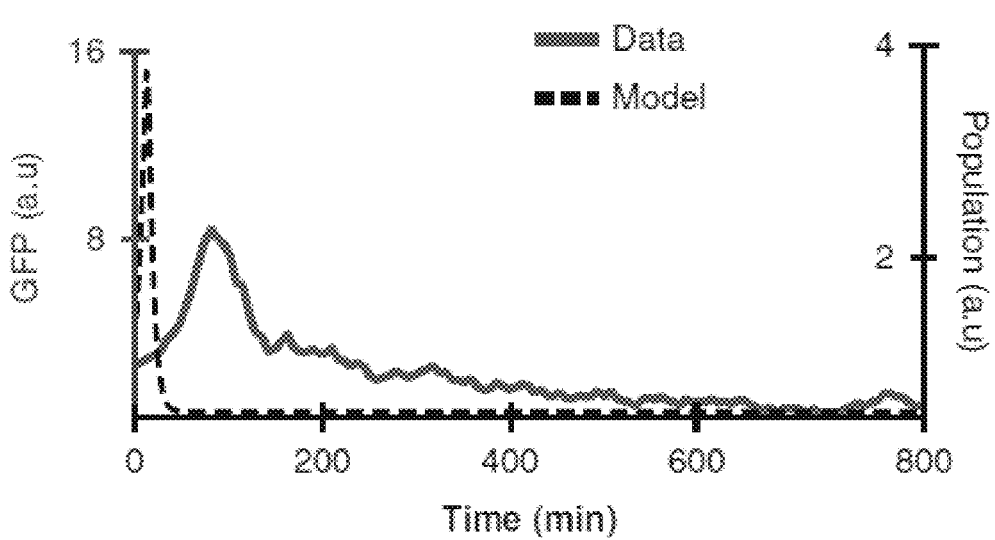
Figure 5:
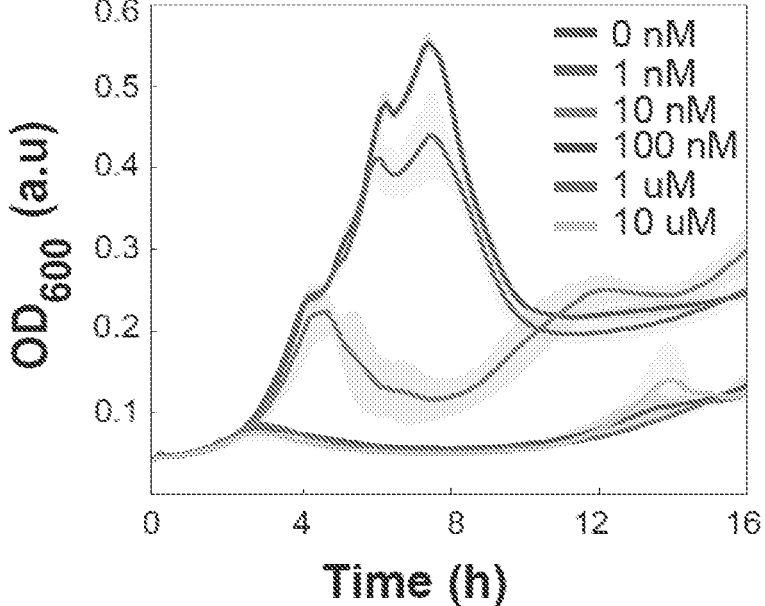
FIG. 5 shows iSLC growth curves from plate reader experiments obtained with varying concentrations of p-coumaric acid. Lines and shaded areas represent the mean and standard deviation (n=3) respectively.
Figure 6A:
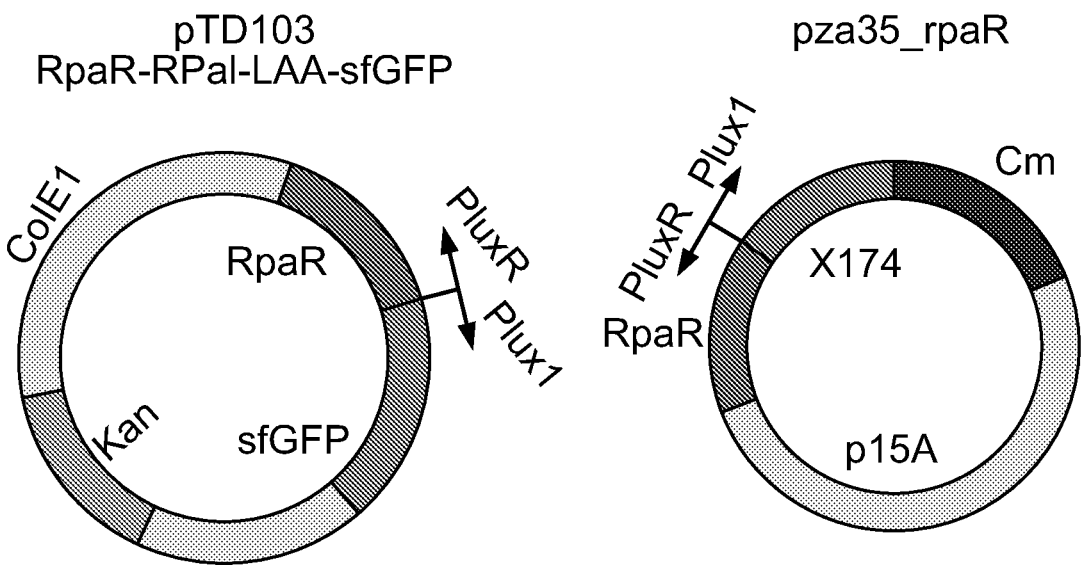
FIG. 6A shows a schematic diagram of plasmid maps from strain LEAKY which lacks the Rpa cassette (RpaI-Plux-RpaR).
Figure 6B:
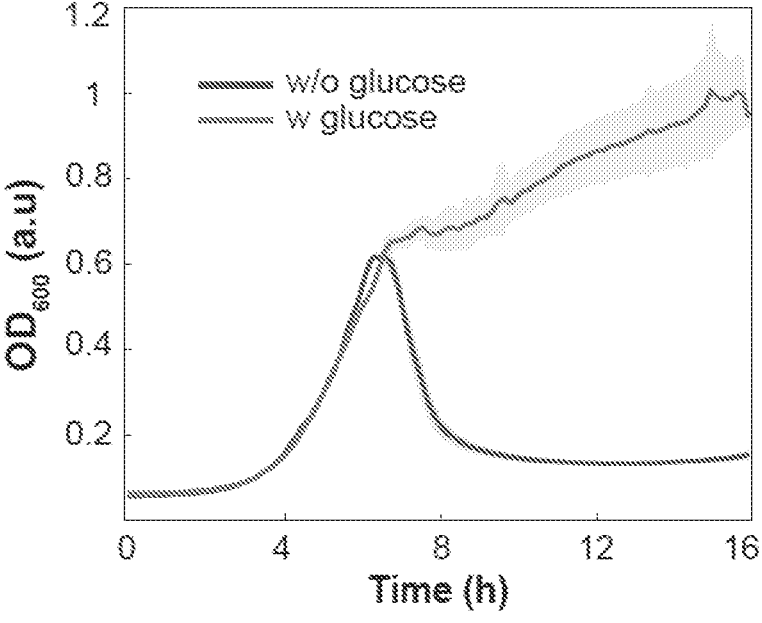
FIG. 6B shows plate reader data obtained by growing strain LEAKY in presence and absence of glucose respectively. High glucose levels in the cell correspond to low CAMP levels which is involved in the luxI promoter activation due to the presence of a binding site for the CAP-CAMP activating complex.
Figure 7:
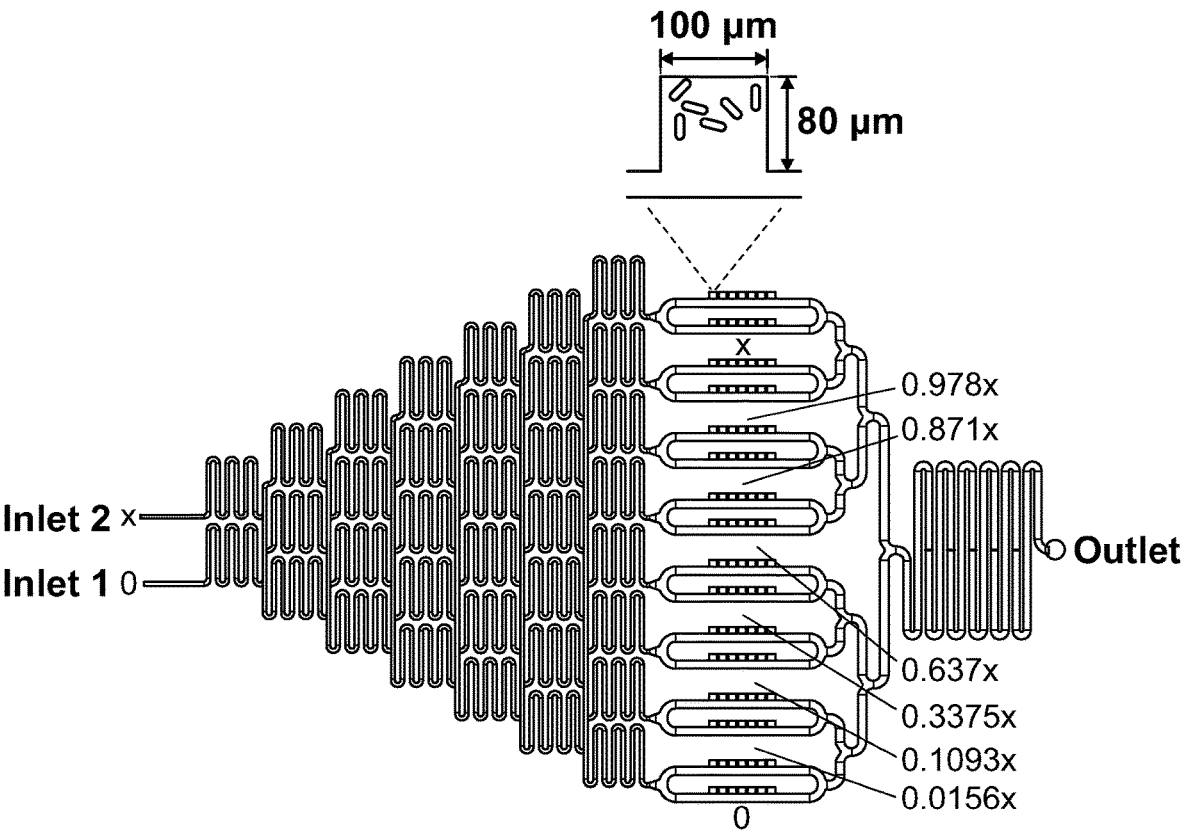
FIG. 7. shows a schematic diagram of a microfluidic gradient device used for experiments in FIG. 2 and FIG. 4. Inlet 1 is set to zero inducer concentration, while Inlet 2 is set to concentration X to generalize dilution factors.

A preliminary test using a microwell plate reader showed an inverse correlation between the population OD (optical density) at lysis and the inducer concentration (FIG. 5). Interestingly, the presence of a lysis event at zero pCA concentration proved to be caused by leaky expression of the LuxI promoter in the sole presence of RpaR (FIGS. 6A-6B). To fully visualize the dynamics of the iSLC strain over time, microfluidic devices were used with an upstream serpentine of branching channels to generate a gradient of eight different inducer concentrations (FIG. 2D and FIG. 7).

Figure 8:
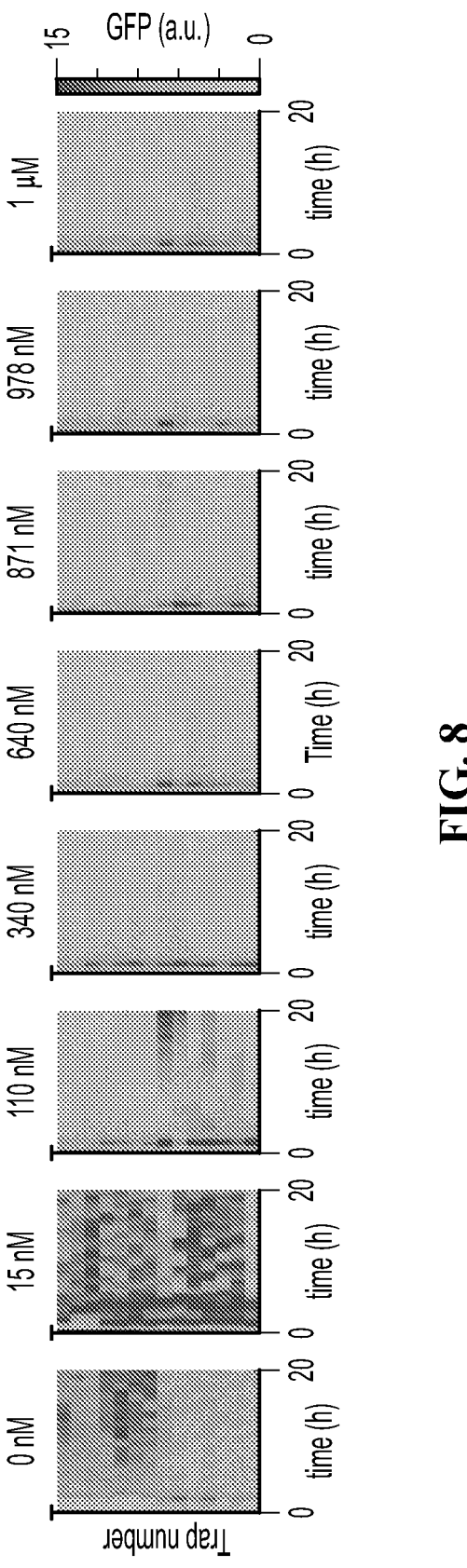
FIG. 8 shows heat maps of fluorescence data for experiments described in FIG. 2. The approximate p-coumaric acid concentration present in each column is reported at the top. For each column, all fourteen traps are reported.

Using fluorescence microscopy to monitor population dynamics, the same three emerging population behaviors predicted by the mathematical model were observed (FIG. 2E and FIGS. 2F, 2G, and 2H). With zero inducer, constant cell growth was observed with sporadic asynchronous lysis due to promoter leakiness. Intermediate inducer concentrations (15 nM) resulted in sustained synchronized oscillations with an average period of approximately 200 minutes. Finally, high pCA concentrations (110 nM to 1 µM) caused universal cell lysis regardless of population density, with only a small fraction (<3% of all. microfluidics traps) able to survive (FIG. 8).

Figure 3A:
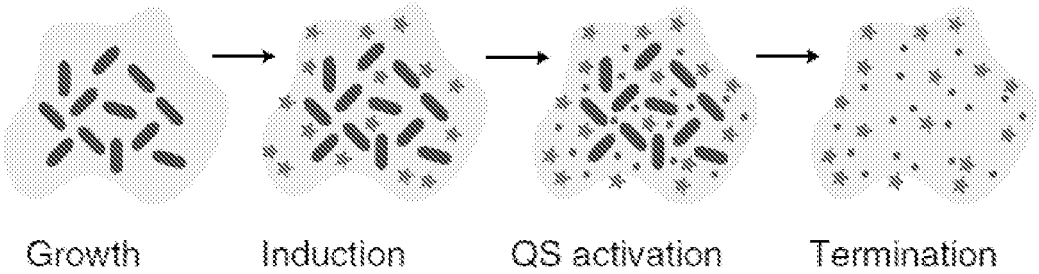
FIG. 3A shows a schematic diagram illustrating the iSLC strain kill switch mechanism.
Figure 3B:
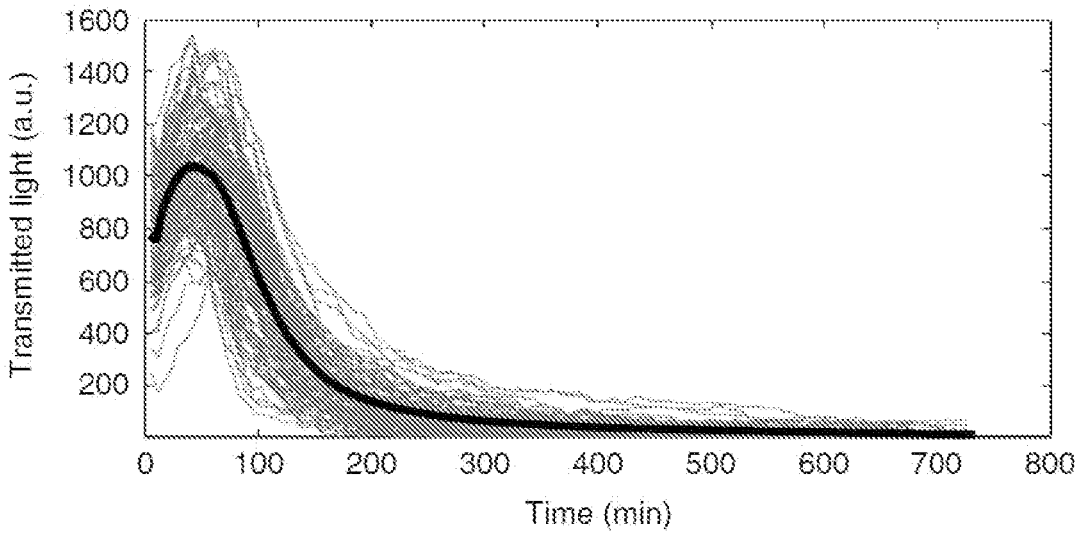
FIG. 3B shows example time traces (n=104) extracted from the transmitted light channel (grey). Solid black line represent the mean. At time zero the cells were induced with 500 nM p-coumaric acid.
Figure 3C:
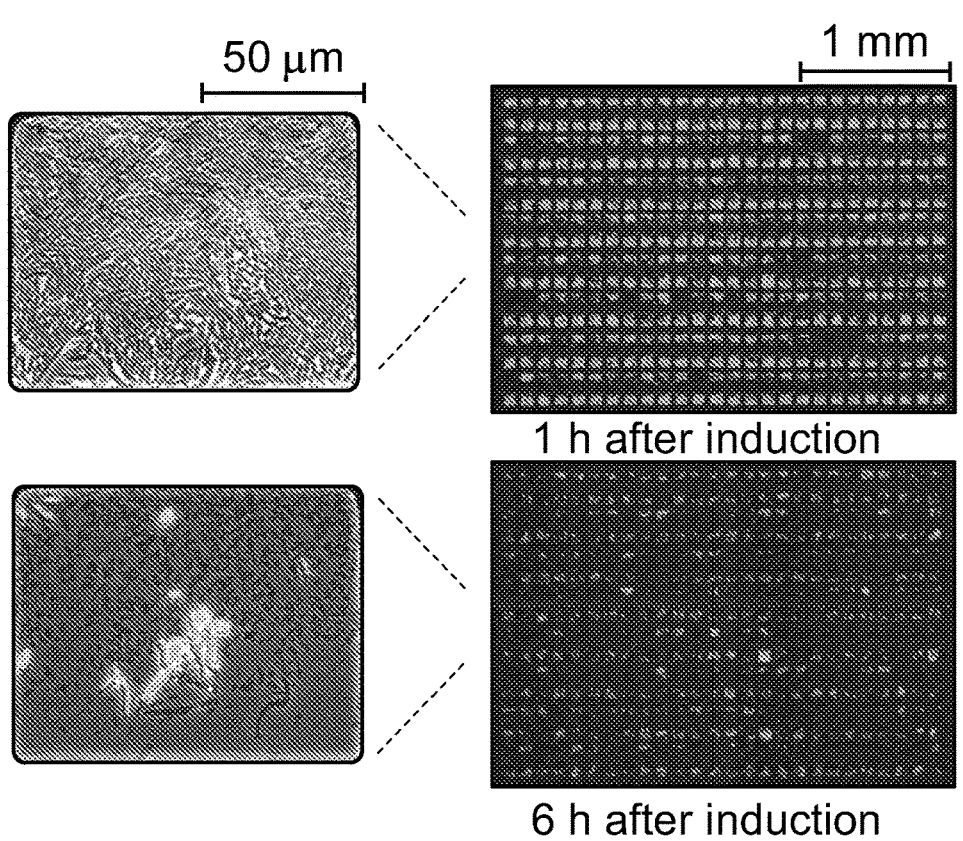
FIG. 3C shows video stills (4×) of the microfluidic chip before (top) and 6 hours after (bottom) induction with 500 nM p-coumaric acid. Left side shows magnified images (30×) of a single representative trap.
Figure 3D:
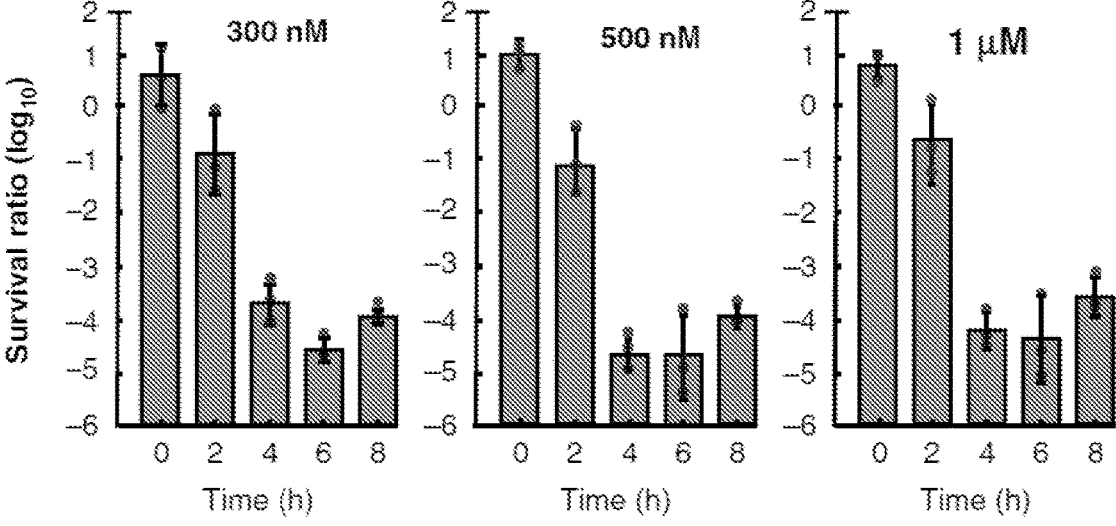
FIG. 3D shows cell viability measured by CFU count following addition of the killing signal (p-coumaric acid) in liquid culture. All data points represent mean±standard deviation of three independent replicates.

Example 3. Characterization of the iSLC Kill Switch Properties in Microfluidics and Liquid Culture Experiments were performed to investigate whether inducer concentrations could be modulated during culture to show the culture can switch between states of constant growth (circuit quiescence), synchronized oscillations in population density (cyclic cargo release) and inducible population death (kill switch). To confirm this principle, experiments were performed to test the ability to drive the population dynamics from state one (population growth) to state three (population death) through pCA induction (FIG. 3A). Experiments were performed in microfluidic devices by initially growing the cells with zero inducer concentration (circuit quiescence). Following complete saturation of all traps, induction was performed with 500 nM pCA. A synchronized lysis event was observed throughout the entire device which resulted in cell death in more than 97% of the 406 microfluidic traps present (FIG. 3B and FIG. 3C). To test the reproducibility of this property in larger volumes, the iSLC strain was grown in 3 mL culture tubes with and without inducer for a period of eight hours. In the presence of p-coumaric acid, a several order of magnitude decrease in cell survival was observed which was independent of inducer concentration (FIG. 3D). This ability to bypass population dependency and intentionally decimate the population, regardless of its density, may serve as an integrated kill switch to regulate strain removal in space and time.

Example 4. IQS Enabled Modulation of Orthogonal Multi-Strain Dynamics

Figure 4A:
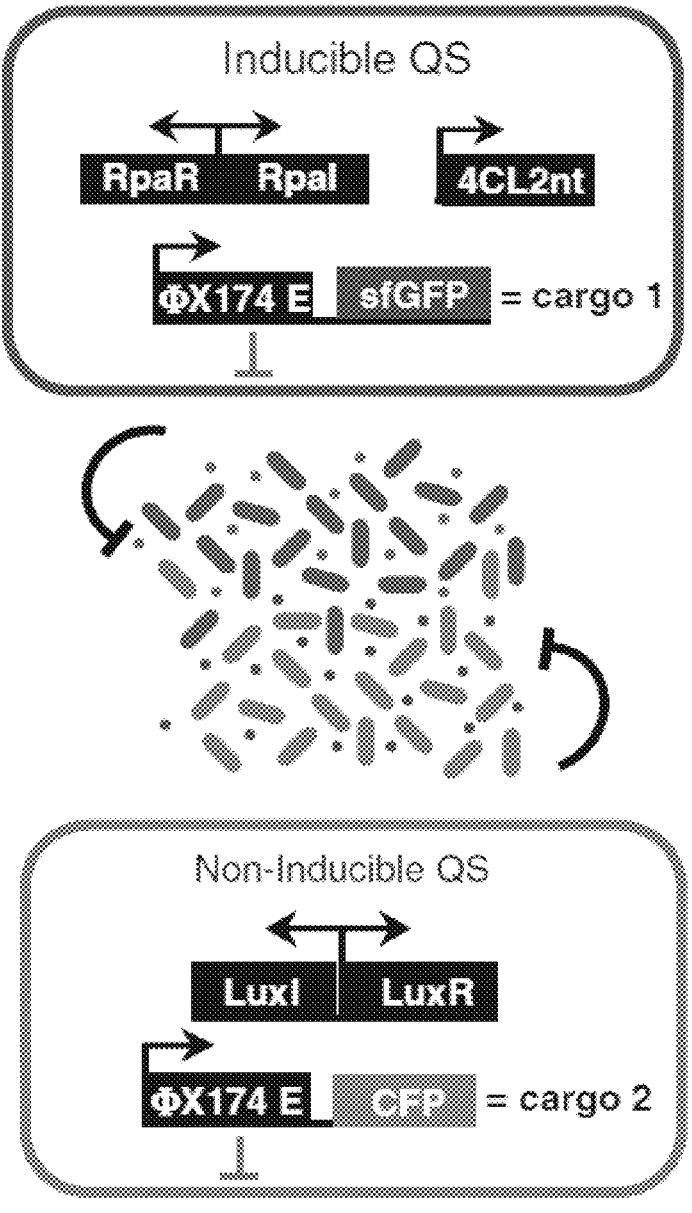
FIG. 4A shows a schematic diagram illustrating co-culture of the two strains used with orthogonal inducible (iSLC) and non-inducible (SLC) quorum sensing respectively.
Figure 4B:
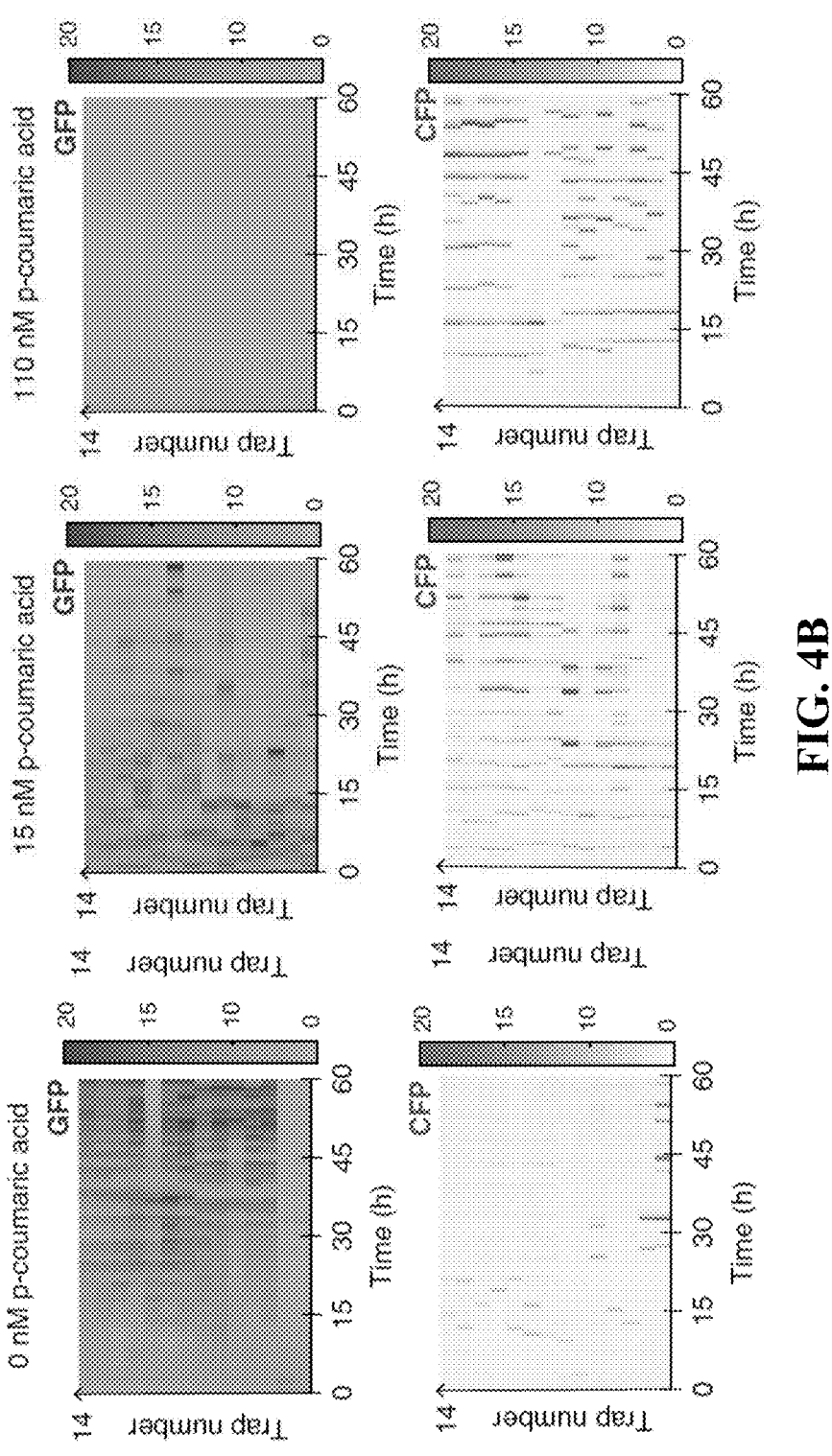
FIG. 4B shows heat maps representing the fluorescence time traces of all fourteen traps present per column of the device. Top rows show the GFP values and bottom rows the CFP values. Fluorescence signals are used as a proxy for population density.
Figure 4C:
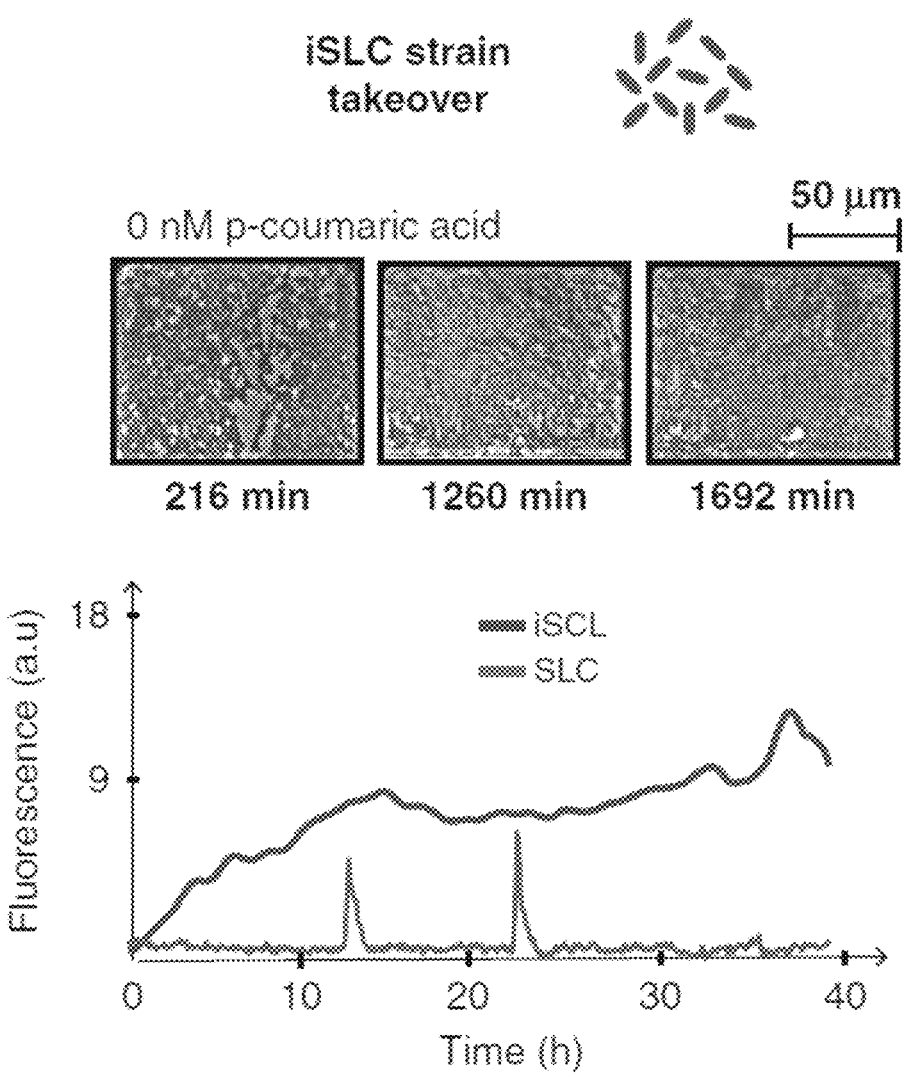
FIG. 4C shows video stills of the co-culture for a 0 nM inducer concentrations at multiple time points (top Panel) and the corresponding fluorescence time traces for GFP and CFP (bottom panel).
Figure 4D:
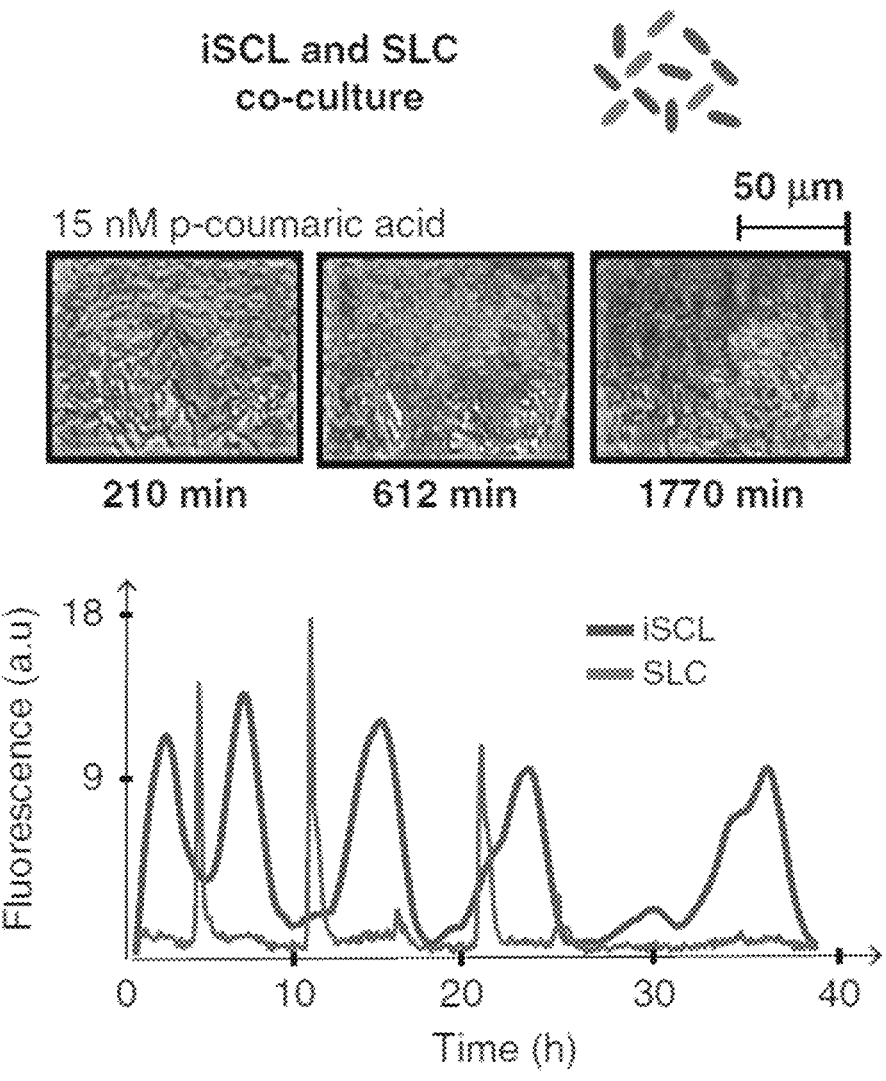
FIG. 4D shows video stills of the co-culture for a 15 nM inducer concentrations at multiple time points (top Panel) and the corresponding fluorescence time traces for GFP and CFP (bottom panel).
Figure 4E:
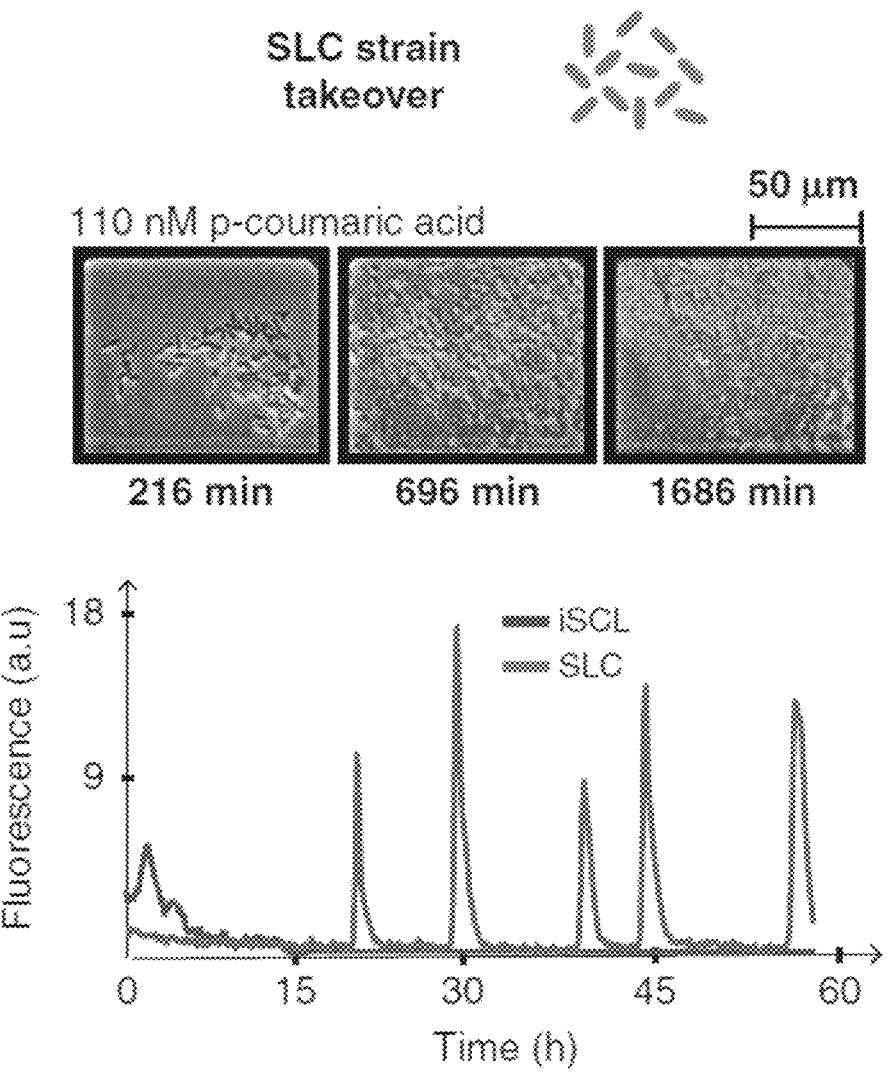
FIG. 4E shows video stills of the co-culture for a 110 nM inducer concentrations at multiple time points (top Panel) and the corresponding fluorescence time traces for GFP and CFP (bottom panel).
Figure 9:
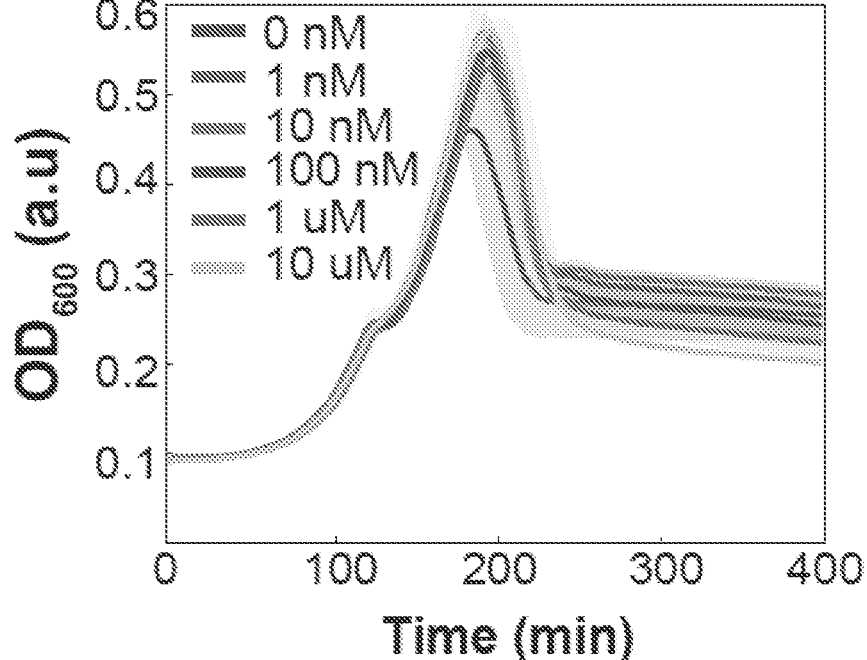
FIG. 9 shows growth curves from plate reader experiments for the iSLC strain. For all p-coumaric acid concentrations tested the growth curves are unaffected, confirming complete orthogonality to the compound. Lines and shaded areas represent the mean and s.d. (n=3) respectively.
Figure 10:
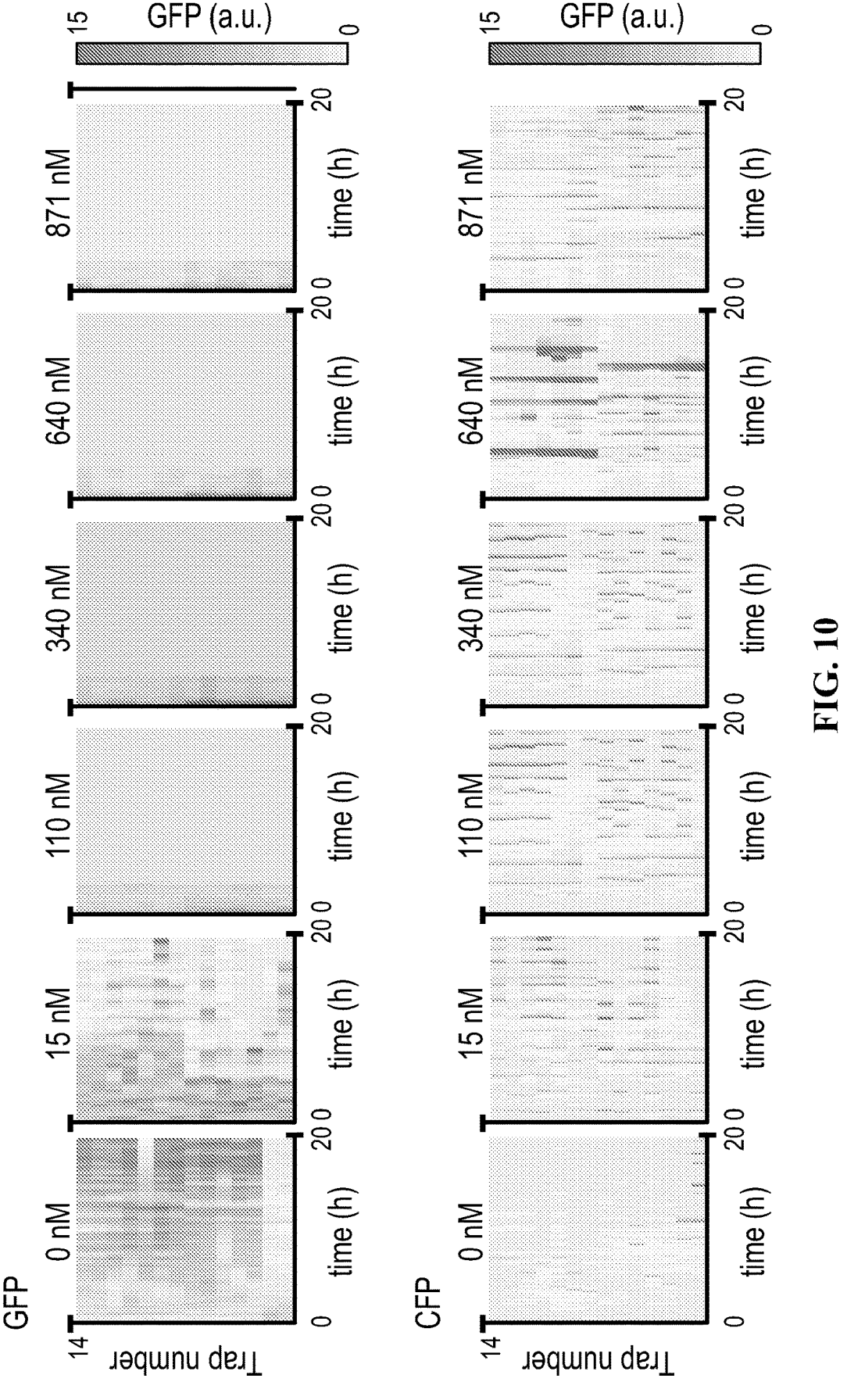
FIG. 10 shows heat maps of fluorescence data for the experiments described in FIG. 4. The approximate p-coumaric acid concentration present in each column is reported at the top. For each column, all fourteen traps are reported. GFP is reported in the top row. CFP is reported in the bottom row.
Figure 11:
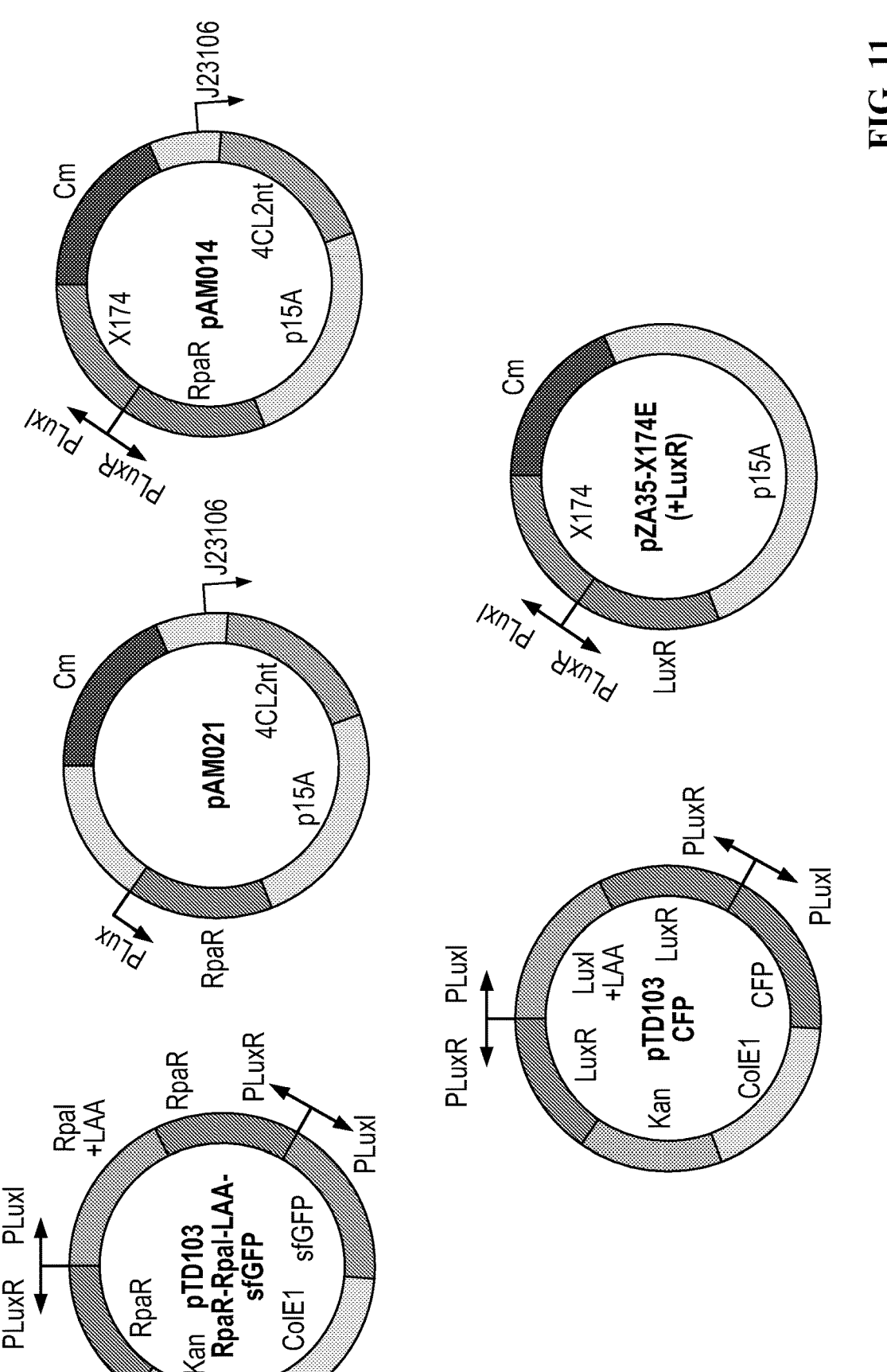
FIG. 11 shows plasmid maps for plasmids used in this study. LAA stands for LAA ClpXP mediated degradation tag.

Experiments were performed to investigate the orthogonal properties of the iQS circuit by co-culturing the iSLC with a non-inducible SLC strain based on the lux QS system, one of the most commonly used and well understood QS systems in synthetic biology (FIG. 4A). First, the absence of crosstalk between p-coumaric acid and the lux QS system was demonstrated by growing the iSLC strain in a range of different pCA concentrations (FIG. 9). Next, a previously described microfluidic chip was used (FIG. 2D and FIG. 7) to co-culture the iSLC and SLC strains (starting at 1:1 ratio) under a gradient of inducer concentrations. Interestingly, it was observed that by varying pCA concentration, precise control over community composition of the microfluidic traps could be achieved. Without inducer, the quiescent iSLC strain was able to displace the SLC strain due to an advantage in population growth rate. At intermediate concentrations (15 nM), stable co-culture of both strains were maintained with independently sustained oscillations for more than 40 hours. High pCA concentrations (110 nM) resulted in the death of all iSLC cells, allowing the SLC strain to fully take over (FIG. 4B and FIGS. 4C, 4D, and 4E). For inducer values higher than 340 nM, the dynamics were unanimously characterized by iSLC death and SLC takeover (FIG. 10). As demonstrated, the absence of cross-talk between the pCA derived signaling molecule and the majority of well-characterized quorum sensing systems, enables the simultaneous use of multiple quorum sensing in co-culture, providing exciting new possibilities for microbial community engineering.

EMBODIMENTS

Embodiment A1. A method of inducing quorum sensing, the method comprising:

(a) culturing a bacterial strain, wherein the bacterial strain comprises (i) a first nucleic acid sequence encoding a first activator polypeptide that is capable of activating a quorum sensing system, wherein the first nucleic acid sequence is operably linked to an activatable promoter;

(ii) a second nucleic acid sequence encoding a second activator polypeptide that is capable of activating a quorum sensing system, wherein the second nucleic acid sequence is operably linked to an activatable promoter; and (iii) a third nucleic acid sequence encoding a third activator polypeptide that is capable of activating a quorum sensing system, wherein the third nucleic acid sequence is operably linked to a promoter;

(b) contacting the bacterial strain with an inducer molecule; and (c) converting the inducer molecule into a quorum sensing molecule, thereby allowing induction of quorum sensing in the bacterial strain.

Embodiment 2. The method of embodiment 1, wherein the quorum sensing system is a Lux-like quorum sensing system selected from the group consisting of: a lux system from *Vibrio fischeri*; a las system from *Pseduomonas aeruginosa*; a rhl system from *Pseduomonas aeruginosa*; a tra system from *Agrobacterium tumefaciens*; a rpa system from *Rhodopseudomonas palustris*; an ahy system from *Aeromonas hydrophilia*; a sma system from *Serratia marcescens*; cer system from *Rhodobacter sphaeroides*; and an exp system from *Sinorhizobium meliloti*.

Embodiment 3. The method of any one of embodiments 1-2, wherein the quorum sensing system is an rpa quorum sensing system.

Embodiment 4. The method of any one of embodiments 1-2, wherein the quorum sensing system is a lux quorum sensing system.

Embodiment 5. The method of any one of embodiments 1-4, wherein the quorum sensing system combines elements of the rpa quorum sensing system and the lux quorum sensing system.

Embodiment 6. The method of any one of embodiments 1-5, wherein the activatable promoter comprises a LuxR-AHL activatable luxI promoter.

Embodiment 7. The method of any one of embodiments 1-5, wherein the activatable promoter comprises an RpaR-AHL activatable RpaI promoter.

Embodiment 8. The method of any one of embodiments 1-7, wherein the first polypeptide comprises a first enzyme, wherein expression of the enzyme produces a quorum sensing molecule precursor.

Embodiment 9. The method of embodiment 8, wherein the second enzyme is a p-coumaric acid-CoA ligase.

Embodiment 10. The method of embodiment 9, wherein the p-coumaric acid-CoA ligase is encoded by the 4CL2nt gene from the plant *Nicotiana tabacum.*

Embodiment 11. The method of any one of embodiments 1-10, wherein the quorum sensing molecule precursor is p-Coumaroyl-CoA.

Embodiment 12. The method of any one of embodiments 1-11, wherein the second activator polypeptide comprises a second enzyme, wherein expression of the enzyme produces a quorum sensing molecule.

Embodiment 13. The method of embodiment 12, wherein the enzyme is a 4-coumaroyl-homoserine lactone synthase (RpaI) synthase.

Embodiment 14. The method of embodiment 13, wherein the RpaI synthase is encoded by the RpaI gene from the plant *Rhodopseudomonas palustris.*

Embodiment 15. The method of any one of embodiments 1-14, wherein the quorum sensing molecule is p-Coumaroyl-HSL.

Embodiment 16. The method of any one of embodiments 1-15, wherein the third activator polypeptide comprises a signaling molecule, wherein the signaling molecule interacts with the quorum sensing molecule.

Embodiment 17. The method of embodiment 16, wherein the signaling molecule is a HTH-type quorum sensing-dependent transcriptional regulator (RpaR).

Embodiment 18. The method of embodiment 17, wherein the RpaR signaling molecule is encoded by the RpaR gene from the plant *Rhodopseudomonas palustris.*

Embodiment 19. The method of any one of embodiments 1-18, wherein the interaction of RpaR and the quorum sensing molecule p-Coumaroyl-HSL results in transcriptional regulation of downstream target genes.

Embodiment 20. The method of any one of embodiments 1-19, wherein the first activator polypeptide is a p-coumaric acid-CoA ligase, the second activator polypeptide is a RpaI synthase, and the third activator polypeptide is a RpaR signaling molecule.

Embodiment 21. The method of any one of embodiments 1-20, wherein the inducer molecule is p-coumaric acid.

Embodiment 22. The method of any one of embodiments 1-21, wherein the first activator polypeptide is p-coumaric acid-CoA ligase that produces p-Coumaroyl-CoA from the substrate p-coumaric acid.

Embodiment 23. The method of any one of embodiments 1-22, wherein the second activator polypeptide is RpaI synthase that produces p-Coumaroyl-HSL from the substrates p-Coumaroyl-CoA.

Embodiment 24. The method of any one of embodiments 1-23, wherein the third activator polypeptide is a RpaR signaling molecule that interacts with the p-Coumaroyl-HSL.

Embodiment 25. The method of any one of embodiments 1-24, wherein the method further comprises a fourth nucleic acid sequence encoding a gene of interest, wherein the fourth nucleic acid sequence is operably linked to a promoter.

Embodiment 26. The method of embodiment 25, wherein the gene of interest encodes a bacteriophage lytic protein capable of forming a lesion in a host cell's membrane.

Embodiment 27. The method of embodiment 26, wherein the lysis gene is from a bacteriophage ΦX174.

Embodiment 28. The method of any one of embodiments 1-27, wherein the method further comprises a fifth nucleic acid sequence encoding a reporter polypeptide selected from a nucleic acid encoding a green fluorescent protein (GFP), cyan fluorescent protein (CFP), red fluorescent protein (RFP), or a variant thereof.

Embodiment 29. The method of embodiment 28, wherein the fifth nucleic acid sequence is operably linked to a promoter or is operably linked to the first, second, third, and/or fourth nucleic acid sequences.

Embodiment 30. The method of any one of embodiments 1-24, wherein the method comprises a vector comprising the first nucleic acid sequence, the second nucleic acid sequence, and the third nucleic acid sequence.

Embodiment 31. The method of any one of embodiments 1-27, wherein the method comprises a vector comprising the first nucleic acid sequence, the second nucleic acid sequence, the third nucleic acid sequence, and the fourth nucleic acid sequence.

Embodiment 32. The method of any one of embodiments 1-24 or 28-29, wherein the method comprises a vector comprising the first nucleic acid sequence, the second nucleic acid sequence, the third nucleic acid sequence, and the fifth nucleic acid sequence.

Embodiment 33. The method of any one of embodiments 1-29, wherein the method comprises a vector comprising the first nucleic acid sequence, the second nucleic acid sequence, the third nucleic acid sequence, the fourth nucleic acid sequence, and the fifth nucleic acid sequence.

Embodiment 34. The method of any one of embodiments 1-24, wherein the method comprises a first vector and a second vector, wherein the first vector comprises a first nucleic acid sequence and the second vector comprises the second nucleic acid sequence and the third nucleic acid sequence.

Embodiment 35. The method of any one of embodiments 1-24, wherein the method comprises a first vector, a second vector, and a third vector, wherein (i) the first vector comprises the first nucleic acid sequence, (ii) the second vector comprises the second nucleic acid sequence and (iii) the third vector comprises the fourth nucleic acid sequence.

Embodiment 36. The method of any one of embodiments 1-35, wherein the one or more vectors are integrated into the genome of the bacterial strain.

Embodiment 37. The method of any one of embodiments 30-36, wherein the one or more vectors each comprise a vector-stabilizing element.

Embodiment 38. The method of embodiment 37, wherein the vector-stabilizing element is a toxin/antitoxin system or an actin-like protein partitioning system.

Embodiment 39. The method of any one of embodiments 1-38, wherein the culturing occurs in a microfluidic device.

Embodiment 40. The method of any one of embodiments 1-39, wherein the bacterial strain is *E. coli.*

Embodiment 41. The method of any one of embodiments 1-40, wherein the method further comprises a second bacterial strain.

Embodiment 42. A bacterial strain produced by the method of any one of embodiments 1-40.

Embodiment 43. A composition comprising the bacterial strain of embodiment 42.

Embodiment 44. A bacterial strain comprising (i) a first nucleic acid sequence encoding a first activator polypeptide that is capable of activating a quorum sensing system, wherein the first nucleic acid sequence is operably linked to an activatable promoter;

(ii) a second nucleic acid sequence encoding a second activator polypeptide that is capable of activating a quorum sensing system, wherein the second nucleic acid sequence is operably linked to an activatable promoter; and (iii) a third nucleic acid sequence encoding a third activator polypeptide that is capable of activating a quorum sensing system, wherein the third nucleic acid sequence is operably linked to a promoter.

Embodiment 45. The bacterial strain of embodiment 44, wherein the quorum sensing system is a Lux-like quorum sensing system selected from the group consisting of: a lux system from *Vibrio fischeri*; a las system from *Pseduomonas aeruginosa*; a rhl system from *Pseduomonas aeruginosa*; a tra system from *Agrobacterium tumefaciens*; a rpa system from *Rhodopseudomonas palustris*; an ahy system from *Aeromonas hydrophilia*; a sma system from *Serratia marcescens*; cer system from *Rhodobacter sphaeroides*; and an exp system from *Sinorhizobium meliloti*.

Embodiment 46. The bacterial strain of embodiment 45, wherein the quorum sensing system is an rpa quorum sensing system.

Embodiment 47. The bacterial strain of embodiment 45, wherein the quorum sensing system is a lux quorum sensing system.

Embodiment 48. The bacterial strain of any one of embodiments 44-47, wherein the quorum sensing system combines elements of the rpa quorum sensing system and the lux quorum sensing system.

Embodiment 49. The bacterial strain of any one of embodiments 44-48, wherein the activatable promoter comprises a LuxR-AHL activatable luxI promoter.

Embodiment 50. The bacterial strain of any one of embodiments 44-48, wherein the activatable promoter comprises a RpaR-AHL activatable RpaI promoter.

Embodiment 51 The bacterial strain of any one of embodiments 44-50, wherein the first polypeptide comprises a first enzyme, wherein expression of the enzyme produces a quorum sensing molecule precursor.

Embodiment 52. The bacterial strain of embodiment 51, wherein the second enzyme comprises a p-coumaric acid-CoA ligase.

Embodiment 53. The bacterial strain of embodiment 52, wherein the p-coumaric acid-CoA ligase is encoded by the 4CL2nt gene from the plant *Nicotiana tabacum*.

Embodiment 54. The bacterial strain of any one of embodiment 44-53, wherein the quorum sensing molecule precursor is p-Coumaroyl-CoA.

Embodiment 55. The bacterial strain of any one of embodiments 44-54, wherein the second activator polypeptide comprises a second enzyme, wherein expression of the enzyme produces a quorum sensing molecule.

Embodiment 56. The bacterial strain of embodiment 55, wherein the enzyme is a 4-coumaroyl-homoserine lactone synthase (RpaI) synthase.

Embodiment 57. The bacterial strain of embodiment 56, wherein the RpaI synthase is encoded by the RpaI gene from the plant *Rhodopseudomonas palustris*.

Embodiment 58. The bacterial strain of any one of embodiment 55-57, wherein the quorum sensing molecule is p-Coumaroyl-HSL.

Embodiment 59. The bacterial strain of any one of embodiments 44-58, wherein the third activator polypeptide comprises a signaling molecule, wherein the signaling molecule is capable of interacting with the quorum sensing molecule.

Embodiment 60. The bacterial strain of embodiment 59, wherein the signaling molecule is a HTH-type quorum sensing-dependent transcriptional regulator (RpaR).

Embodiment 61. The bacterial strain of embodiment 60, wherein the RpaR signaling molecule is encoded by the RpaR gene from the plant *Rhodopseudomonas palustris*.

Embodiment 62. The bacterial strain of any one of embodiments 44-61, wherein the bacterial strain further comprises a fourth nucleic acid sequence encoding a gene of interest, wherein the fourth nucleic acid sequence is operably linked to a promoter.

Embodiment 63. The bacterial strain of embodiment 62, wherein the gene of interest encodes a bacteriophage lytic protein capable of forming a lesion in a host cell's membrane.

Embodiment 64. The bacterial strain of embodiment 63, wherein the lysis gene is E from a bacteriophage ΦX174.

Embodiment 65. The bacterial strain of any one of embodiments 62-64, wherein the gene of interest encodes a therapeutic agent.

Embodiment 66. The bacterial strain of embodiment 65, wherein the therapeutic agent is selected from the group consisting of: an inhibitory nucleic acid, a cytokine, a fusion protein, and an antibody or antigen-binding fragment thereof.

Embodiment 67. The bacterial strain of any one of embodiments 27-28, wherein the therapeutic agent is a therapeutic polypeptide.

Embodiment 68. The bacterial strain of any one of embodiments 44-67, wherein the method further comprises a fifth nucleic acid sequence encoding a reporter polypeptide selected from a gene encoding a green fluorescent protein (GFP), cyan fluorescent protein (CFP), red fluorescent protein (RFP), or a variant thereof.

Embodiment 69. The bacterial strain of embodiment 68, wherein the fifth nucleic acid sequence is operably linked to a promoter or is operably linked to the first, second, third, and/or fourth nucleic acid sequences.

Embodiment 70. A pharmaceutical composition comprising any of the bacterial strains of embodiments 44-69.

Embodiment 71. The pharmaceutical composition of embodiment 70, wherein the pharmaceutical composition is formulated for in situ drug delivery.

Embodiment 72. A method of treating a disease in a subject, the method comprising: administering to a subject in need therapeutically effective amounts of any of the bacterial strains of embodiments 44-69 or a pharmaceutical composition of any one of embodiments 70-71, to thereby treat the disease in the subject.

Embodiment 73. The method of embodiment 72, wherein the disease is cancer.

It is to be understood that while the disclosure has been described in conjunction with the detailed description thereof, the foregoing description is intended to illustrate and not limit the scope of the disclosure, which is defined by the scope of the appended claims. Other aspects, advantages, and modifications are within the scope of the following claims.

Sequence Appendix

| SEQ ID NO: | Identifier | SEQUENCES |
|---|---|---|
| 1 | 4c12nt gene | ATGGAGAAAGACACGAAGCAAGTTGACATCATTTTTCGCTCGAAACTG<br>CCGGACATTTACATTCCGAATCATCTGCCGCTGCATAGCTACTGCTTCG<br>AGAACATTTCTGAATTTTCTAGCCGTCCGTGTCTGATTAACGGTGCCAA<br>TAAACAGATCTATACGTACGCGGACGTCGAGTTGAACAGCCGTAAGGT<br>CGCAGCGGGTCTGCACAAGCAAGGCATCCAGCCTAAAGATACCATCAT<br>GATTCTGTTGCCAAATTCTCCGGAGTTTGTGTTTGCGTTTATCGGCGCAA<br>GCTACCTGGGTGCGATTAGCACGATGGCAAATCCGCTGTTTACCCCGGC<br>TGAGGTTGTTAAACAAGCAAAAGCCAGCAGCGCGAAGATCATCGTGAC<br>CCAAGCATGCCACGTCAACAAAGTTAAGGACTATGCCTTCGAAAATGA<br>CGTCAAGATCATTTGCATCGATAGCGCGCCTGAAGGTTGTCTGCATTTC<br>AGCGTTCTGACGCAGGCTAACGAACACGATATTCCGGAAGTTGAGATTC<br>AGCCGGACGATGTGGTGGCCCTGCCGTACTCCAGCGGTACCACCGGCCT<br>GCCGAAAGGCGTTATGCTGACCCACAAGGGCCTGGTGACGAGCGTCGC<br>CCAGCAGGTCGATGGTGAAAACCCGAACCTGTACATCCACAGCGAAGA<br>TGTTATGCTGTGTGTTCTGCCACTGTTCCACATCTATTCCCTGAACAGCG<br>TCCTGCTGTGCGGCCTGCGTGTGGGCGCTGCCATTTTGATTATGCAGAA<br>GTTTGACATTGTCAGCTTCTTGGAACTGATCCAACGCTACAAGGTGACG<br>ATCGGTCCGTTCGTCCCGCCGATTGTTTTGGCCATTGCAAAAAGCCCAA<br>TGGTGGATGACTATGACCTGTCGAGCGTGCGTACCGTGATGTCCGGTGC<br>AGCGCCGCTGGGCAAAGAGCTGGAGGATACCGTTCGTGCGAAGTTTCC<br>GAATGCGAAACTGGGTCAAGGCTACGGTATGACTGAAGCAGGTCCGGT<br>GCTGGCGATGTGCTTGGCGTTCGCGAAAGAGCCGTTCGAAATCAAAAG<br>CGGTGCGTGCGGTACCGTGGTGCGTAATGCTGAAATGAAAATTGTGGAT<br>CCGAAAACCGGCAACAGCCTGCCGCGCAACCAGAGCGGTGAGATTTGT<br>ATTCGCGGTGACCAGATTATGAAGGGCTACCTGAATGACCCGGAGGCC<br>ACTGCGCGTACGATCGACAAAGAGGGTTGGCTGTATACCGGCGACATC<br>GGTTATATCGATGACGACGACGAGCTGTTCATCGTTGATCGCCTGAAAG<br>AGTTGATTAAGTACAAGGGTTTCCAAGTTGCGCCTGCGGAACTGGAGGC<br>TCTGCTGTTGAATCATCCGAACATTAGCGATGCAGCAGTCGTTCCGATG<br>AAGGATGAGCAGGCGGGTGAAGTTCCGGTCGCGTTTGTTGTGCGTAGC<br>AACGGCAGCACGATCACCGAGGATGAGGTAAAGGATTTCATTTCCAAA<br>CAAGTCATCTTCTATAAGCGTATCAAGCGTGTGTTTTTCGTCGATGCAAT<br>CCCGAAAAGCCCGTCCGGTAAGATCCTGCGCAAAGACTTGCGTGCGAA<br>GCTGGCGGCAGGTCTGCCGAATTAG |
| 2 | Promoter J23106 | TTCAGAACGCTCGGTTGCCGCCGGGCGTTTTTTATTGGTGAGAATCCAA<br>GCACTAGT |
| 3 | UTR region | TTTACGGCTAGCTCAGTCCTAGGTATAGTGCTAGCTGGATCCAAGAAGG<br>AGATATAACC |
| 4 | Terminator | GCAGCGAACGACGAAAATTACGCCCTTGCAGCGTAACAGATAAAAAAA<br>ATCCTTAGCTTTCGCTAAGGATGATTTCT |
| 5 | p15A origin | AACAACTTATATCGTATGGGGCTGACTTCAGGTGCTACATTTGAAGAGA<br>TAAATTGCACTGAAATCTAGAAATATTTTATCTGATTAATAAGATGATC<br>TTCTTGAGATCGTTTTGGTCTGCGCGTAATCTCTTGCTCTGAAAACGAAA<br>AAACCGCCTTGCAGGGCGGTTTTTCGAAGGTTCTCTGAGCTACCAACTC<br>TTTGAACCGAGGTAACTGGCTTGGAGGAGCGCAGTCACCAAAACTTGTC<br>CTTTCAGTTTAGCCTTAACCGGCGCATGACTTCAAGACTAACTCCTCTA<br>AATCAATTACCAGTGGCTGCTGCCAGTGGTGCTTTTGCATGTCTTTCCGG<br>GTTGGACTCAAGACGATAGTTACCGGATAAGGCGCAGCGGTCGGACTG<br>AACGGGGGGTTCGTGCATACAGTCCAGCTTGGAGCGAACTGCCTACCC<br>GGAACTGAGTGTCAGGCGTGGAATGAGACAAACGCGGCCATAACAGCG<br>GAATGACACCGGTAAACCGAAAGGCAGGAACAGGAGAGCGCACGAGG<br>GAGCCGCCAGGGGGAAACGCCTGGTATCTTTATAGTCCTGTCGGGTTTC<br>GCCACCACTGATTTGAGCGTCAGATTTCGTGATGCTTGTCAGGGGGGCG<br>GAGCCTATGGAAAAACGGCTTTGCCGCGGCCCTCTCACTTCCCTGTTAA<br>GTATCTTCCTGGCATCTTCCAGGAAATCTCCGCCCCGTTCGTAAGCCATT<br>TCCGCTCGCCGCAGTCGAACGACCGAGCGTAGCGAGTCAGTGAGCGAG<br>GAAGCGGAATATATCC |
| 6 | Plux Promoter | TTTGATTCTAATAAATTGGATTTTTGTCACACTATTGTATCGCTGGGAAT<br>ACAATTACTTAACATAAGCACCTGTAGGATCGTACAGGTTTACGCAAGA<br>AAATGGTTTGTTATAGTCGAAT |
| 7 | Lysine gene XI74E | ATGGTACGCTGGACTTTGTGGGATACCCTCGCTTTCCTGCTCCTGTTGAG<br>TTTATTGCTGCCGTCATTGCTTATTATGTTCATCCCGTCAACATTCAAAC<br>GGCCTGTCTCATCATGGAAGGCGCTGAATTTACGGAAAACATTATTAAT<br>GGCGTCGAGCGTCCGGTTAAAGCCGCTGAATTGTTCGCGTTTACCTTGC<br>GTGTACGCGCAGGAAACACTGACGTTCTTACTGACGCAGAAGAAACG<br>TGCGTCAAAAATTACGTGCGGAAGGAGTGA |
| 8 | RpaR gene | ATGATCGTCGGCGAAGATCAGCTTTGGGGACGGCGTGCGCTGGAATTC<br>GTCGATTCCGTCGAACGGCTCGAGGCGCCGGCGCTGATCAGCCGGTTCG |

Sequence Appendix

| SEQ ID NO: | Identifier | SEQUENCES |
|---|---|---|
| | | AATCGCTGATCGCGAGCTGCGGATTTACCGCCTACATCATGGCCGGCCT<br>GCCGTCGCGCAATGCCGGACTACCGGAGCTGACGCGTGGCCAATGGCTG<br>GCCGCGAGACTGGTTCGATCTGTATGTCAGCGAAAACTTCAGCGCGGTC<br>GATCCGGTGCCGCGCCACGGCGCTACCACGGTTCATCCTTTCGTATGGT<br>CCGATGCACCCTACGACCGCGACCGTGATCCGGCCGCCCACCGGGTCAT<br>GACCCGGGCGGCGGAATTCGGACTGGTCGAGGGTTACTGCATTCCGCTG<br>CACTACGACGACGGTAGCGCCGCGATCAGCATGGCCGGCAAGGATCCG<br>GACCTCAGCCCGGCCGCGCGCGGCGCGATGCAGCTGGTCAGCATCTAC<br>GCGCATAGTCGCCTGCGCGCACTCAGCCGGCCAAAGCCGATCCGGCGC<br>AACCGGCTCACGCCGCGCGAGTGCGAGATCCTGCAATGGGCAGCGCAG<br>GGCAAGACCGCCTGGGAAATCTCGGTAATCCTCTGCATCACCGAACGC<br>ACGGTGAAATTCCATCTGATCGAAGCCGCCCGCAAGCTCGACGCCGCC<br>AACCGCACCGCGGCGGTTGCCAAGGCATTGACGCTCGGATTGATCCGTT<br>TGTGA |
| 9 | Chloramphenicol resistance gene | GATATCTGGCGAAAATGAGACGTTGATCGGCACGTAAGAGGTTCCAAC<br>TTTCACCATAATGAAATAAGATCACTACCGGGCGTATTTTTTGAGTTAT<br>CGAGATTTTCAGGAGCTAAGGAAGCTAAAATGGAGAAAAAATCACTG<br>GATATACCACCGTTGATATATCCCAATGGCATCGTAAAGAACATTTTGA<br>GGCATTTCAGTCAGTTGCTCAATGTACCTATAACCAGACCGTTCAGCTG<br>GATATTACGGCCTTTTTAAAGACCGTAAAGAAAAATAAGCACAAGTTTT<br>ATCCGGCCTTTATTCACATTCTTGCCCGCCTGATGAATGCTCATCCGGAA<br>TTCCGTATGGCAATGAAAGACGGTGAGCTGGTGATATGGGATAGTGTTC<br>ACCCTTGTTACACCGTTTTCCATGAGCAAACTGAAACGTTTTCATCGCTC<br>TGGAGTGAATACCACGACGATTTCCGGCAGTTTCTACACATATATTCGC<br>AAGATGTGGCGTGTTACGGTGAAAACCTGGCCTATTTCCCTAAAGGGTT<br>TATTGAGAATATGTTTTTCGTCTCAGCCAATCCCTGGGTGAGTTTCACCA<br>gttttgatttaaacgtggccaatatggacaacttcttcgcccccgtttttc<br>ACCATGGGCAAATATTATACGCAAGGCGACAAGGTGCTGATGCCGCTG<br>GCGATTCAGGTTCATCATGCCGTCTGTGATGGCTTCCATGTCGGCAGAA<br>TGCTTAATGAATTACAACAGTACTGCGATGAGTGGCAGGGCGGGGCGT<br>AATTTGATATC |
| 10 | >pTD103LuxI_CFP | CTCGAGTTAATTTTTAAAGTATGGGCAATCAATTGCTCCTGTTAAAATT<br>GCTTTAGAAATACTTTGGCAGCGGTTTGTTGTATTGAGTTTCATTTGCGC<br>ATTGGTTAAATGGAAAGTGACAGTACGCTCACTGCAGCCTAATATTTTT<br>GAAATATCCCAAGAGCTTTTTCCTTCGCATGCCCACGCTAAACATTCTTT<br>TTCTCTTTTTGGTTAAATCGTTGTTTGATTTATTATTTGCTATATTTATTTT<br>TCGATAATTATCAACTAGAGAAGGAACAATTAATGGTATGTTCATACAC<br>GCATGTAAAAATAAACTATCTATATAGTTGTCTTTTTCTGAATGTGCAA<br>AACTAAGCATTCCGAAGCCATTGTTAGCCGTATGAATAGGGGAAACTAA<br>ACCCAGTGATAAGACCTGATGTTTTCGCTTCTTTAATTACATTTGGAGAT<br>TTTTTATTTACAGCATTGTTTTCAAATATATTCCAATTAATTGGTGAATG<br>ATTGGAGTTAGAATAATCTACTATAGGATCATATTTTATTAAATTAGCG<br>TCATCATAATATTGCCTCCATTTTTTAGGGTAATTATCTAGAATTGAAAT<br>ATCAGATTTAACCATAGAATGAGGATAAATGATCGCGAGTAAATAATA<br>TTCACAATGTACCATTTTAGTCATATCAGATAAGCATTGATTAATATCAT<br>TATTGCTTCTACAAGCTTTAATTTTATTAATTATTCTGTATGTGTCGTCG<br>GCATTTATGTTTTTCATACCCATCTCTTTATCCTTACCTATTGTTTGTCGC<br>AAGTTTTGCGTGTTATATATCATTAAAACGGTAATGGATTGACATTTGA<br>TTCTAATAAATTGGATTTTTGTCACACTATTGTATCGCTGGGAATACAAT<br>TACTTAACATAAGCACCTGTAGGATCGTACAGGTTTACGCAAGAAAATG<br>GTTTGTTATAGTCGAATGAATTCATTAAAGAGGAGAAAGGTACCATGAC<br>TATAATGATAAAAAAATCGGATTTTTTGGCAATTCCATCGGAGGAGTAT<br>AAAGGTATTCTAAGTCTTCGTTATCAAGTGTTTAAGCAAAGACTTGAGT<br>GGGACTTAGTTGTAGAAAATAACCTTGAATCAGATGAGTATGATAACTC<br>AAATGCAGAATATATTTATGCTTGTGATGATACTGAAAATGTAAGTGGA<br>TGCTGGCGTTTATTACCTACAACAGGTGATTATATGCTGAAAAGTGTTT<br>TTCCTGAATTGCTTGGTCAACAGAGTGCTCCCAAAGATCCTAATATAGT<br>CGAATTAAGTCGTTTTGCTGTAGGTAAAAATAGCTCAAAGATAAATAAC<br>TCTGCTAGTGAAATTACAATGAAACTATTTGAAGCTATATATAAACACG<br>CTGTTAGTCAAGGTATTACAGAATATGTAACAGTAACATCAACAGCAAT<br>AGAGCGATTTTTAAAGCGTATTAAAGTTCCTTGTCATCGTATTGGAGAC<br>AAAGAAATTCATGTATTAGGTGATACTAAATCGGTTGTATTGTCTATGC<br>CTATTAATGAACAGTTTAAAAAAGCAGTCTTAAATGCAGCGAACGACG<br>AAAATTACGCCCTTGCAGCGTAAACGCGTGCTAGAGGCATCAAATAAA<br>ACGAAAGGCTCAGTCGAAAGACTGGGCCTTTCGTTTTATCTGTTGTTTG<br>TCGGTGAACGCTCTCCTGAGTAGGACAAATCCGCCGCCCTAGACCTAGG<br>CGTCTTCACCTCGAGTTAATTTTTAAAGTATGGGCAATCAATTGCTCCTG<br>TTAAAATTGCTTTAGAAATACTTTGGCAGCGGTTTGTTGTATTGAGTTTC<br>ATTTGCGCATTGGTTAAATGGAAAGTGACAGTACGCTCACTGCAGCCTA<br>ATATTTTTGAAATATCCCAAGAGCTTTTTCCTTCGCATGCCCACGCTAAA<br>CATTCTTTTTTCTCTTTTTGGTTAAATCGTTGTTTGATTTATTATTTGCTATA |

-continued

| Sequence Appendix |
|---|

SEQ
ID
NO: Identifier          SEQUENCES

```
                        TTTATTTTTCGATAATTATCAACTAGAGAAGGAACAATTAATGGTATGT
                        TCATACACGCATGTAAAAATAAACTATCTATATAGTTGTCTTTTTCTGAA
                        TGTGCAAAACTAAGCATTCCGAAGCCATTGTTAGCCGTATGAATAGGGA
                        AACTAAACCCAGTGATAAGACCTGATGTTTTCGCTTCTTTAATTACATTT
                        GGAGATTTTTTATTTACAGCATTGTTTTCAAATATATTCCAATTAATTGG
                        TGAATGATTGGAGTTAGAATAATCTACTATAGGATCATATTTTATTAAA
                        TTAGCGTCATCATAATATTGCCTCCATTTTTTAGGGTAATTATCTAGAAT
                        TGAAATATCAGATTTAACCATAGAATGAGGATAAATGATCGCGAGTAA
                        ATAATATTCACAATGTACCATTTTAGTCATATCAGATAAGCATTGATTA
                        ATATCATTATTGCTTCTACAAGCTTTAATTTTATTAATTATTCTGTATGT
                        GTCGTCGGCATTTATGTTTTTCATACCCATCTCTTTATCCTTACCTATTGT
                        TTGTCGCAAGTTTTGCGTGTTATATATCATTAAAACGGTAATGGATTGA
                        CATTTGATTCTAATAAATTGGATTTTTGTCACACTATTGTATCGCTGGGA
                        ATACAATTACTTAACATAAGCACCTGTAGGATCGTACAGGTTTACGCAA
                        GAAAATGGTTTGTTATAGTCGAATGAATTCATTAAAGAGGAGAAAGGT
                        ACCATGTCTAAAGGTGAAGAATTATTCACTGGTGTTGTCCCAATTTTGG
                        TTGAATTAGATGGTGATGTTAATGGTCACAAATTTTCTGTCTCCGGTGA
                        AGGTGAAGGTGATGCTACTTACGGTAAATTGACCTTAAAATTTATTTGT
                        ACTACTGGTAAATTGCCAGTTCCATGGCCAACCTTAGTCACTACTTTAA
                        CTTGGGGTGTTCAATGTTTTGCTAGATACCCAGATCATATGAAACAACA
                        TGACTTTTTCAAGTCTGCCATGCCAGAAGGTTATGTTCAAGAAAGAACT
                        ATTTTTTTCAAAGATGACGGTAACTACAAGACCAGAGCTGAAGTCAAGT
                        TTGAAGGTGATACCTTAGTTAATAGAATCGAATTAAAAGGTATTGATTT
                        TAAAGAAGATGGTAACATTTTAGGTCACAAATTGGAATACAACGCTATT
                        TCTGATAATGTTTACATCACTGCTGACAAACAAAAGAATGGTATCAAAG
                        CTAACTTCAAAATTAGACACAACATTGAAGATGGTGGTGTTCAATTAGC
                        TGACCATTATCAACAAAATACTCCAATTGGTGATGGTCCAGTCTTGTTA
                        CCAGACAACCATTACTTATCCACTCAATCTAAATTATCCAAAGATCCAA
                        ACGAAAAGAGAGACCACATGGTCTTGTTAGAATTTGTTACTGCTGCTGG
                        TATTACCCATGGTATGGATGAATTGTACAAAACTAGTGCAGCGAACGAC
                        GAAAATTACGCCCTTGCAGCGTGAAAGCTTAATTAGCTGATCTAGACGC
                        GTGCTAGAGGCATCAAATAAAACGAAAGGCTCAGTCGAAAGACTGGGC
                        CTTTCGTTTTATCTGTTGTTTGTCGGTGAACGCTCTCCTGAGTAGGACAA
                        ATCCGCCGCCCTAGACCTAGGGCGTTCGGCTGCGGCGAGCGGTATCAGC
                        TCACTCAAAGGCGGTAATACGGTTATCCACAGAATCAGGGGATAACGC
                        AGGAAAGAACATGTGAGCAAAAGGCCAGCAAAAGGCCAGGAACCGTA
                        AAAAGGCCGCGTTGCTGGCGTTTTTCCATAGGCTCCGCCCCCCTGACGA
                        GCATCACAAAAATCGACGCTCAAGTCAGAGGTGGCGAAACCCGACAGG
                        ACTATAAAGATACCAGGCGTTTCCCCCTGGAAGCTCCCTCGTGCGCTCT
                        CCTGTTCCGACCCTGCCGCTTACCGGATACCTGTCCGCCTTTCTCCCTTC
                        GGGAAGCGTGGCGCTTTCTCATAGCTCACGCTGTAGGTATCTCAGTTCG
                        GTGTAGGTCGTTCGCTCCAAGCTGGGCTGTGTGCACGAACCCCCCGTTC
                        AGCCCGACCGCTGCGCCTTATCCGGTAACTATCGTCTTGAGTCCAACCC
                        GGTAAGACACGACTTATCGCCACTGGCAGCAGCCACTGGTAACAGGAT
                        TAGCAGAGCGAGGTATGTAGGCGGTGCTACAGAGTTCTTGAAGTGGTG
                        GCCTAACTACGGCTACACTAGAAGGACAGTATTTGGTATCTGCGCTCTG
                        CTGAAGCCAGTTACCTTCGGAAAAAGAGTTGGTAGCTCTTGATCCGGCA
                        AACAAACCACCGCTGGTAGCGGTGGTTTTTTTGTTTGCAAGCAGCAGAT
                        TACGCGCAGAAAAAAAGGATCTCAAGAAGATCCTTTGATCTTTTCTACG
                        GGGTCTGACGCTCAGTGGAACGAAAACTCACGTTAAGGGATTTTGGTCA
                        TGACTAGTGCTTGGATTCTCACCAATAAAAAACGCCCGGCGGCAACCG
                        AGCGTTCTGAACAAATCCAGATGGAGTTCTGAGGTCATTACTGGATCTA
                        TCAACAGGAGTCCAAGCGAGCTCTCGAACCCCAGAGTCCCGCTCAGAA
                        GAACTCGTCAAGAAGGCGATAGAAGGCGATGCGCTGCGAATCGGGAGC
                        GGCGATACCGTAAAGCACGAGGAAGCGGTCAGCCCATTCGCCGCCAAG
                        CTCTTCAGCAATATCACGGGTAGCCAACGCTATGTCCTGATAGCGGTCC
                        GCCACACCCAGCCGGCCACAGTCGATGAATCCAGAAAAGCGGCCATTT
                        TCCACCATGATATTCGGCAAGCAGGCATCGCCATGGGTCACGACGAGA
                        TCCTCGCCGTCGGGCATGCGCGCCTTGAGCCTGGCGAACAGTTCGGCTG
                        GCGCGAGCCCCTGATGCTCTTCGTCCAGATCATCCTGATCGACAAGACC
                        GGCTTCCATCCGAGTACGTGCTCGCTCGATGCGATGTTTCGCTTGGTGG
                        TCGAATGGGCAGGTAGCCGGATCAAGCGTATGCAGCCGCCGCATTGCA
                        TCAGCCATGATGGATACTTTCTCGGCAGGAGCAAGGTGAGATGACAGG
                        AGATCCTGCCCCGGCACTTCGCCCAATAGCAGCCAGTCCCTTCCCGCTT
                        CAGTGACAACGTCGAGCACAGCTGCGCAAGGAACGCCCGTCGTGGCCA
                        GCCACGATAGCCGCGCTGCCTCGTCCTGCAGTTCATTCAGGGCACCGGA
                        CAGGTCGGTCTTGACAAAAAGAACCGGGCGCCCCTGCGCTGACAGCCG
                        GAACACGGCGGCATCAGAGCAGCCGATTGTCTGTTGTGCCCAGTCATAG
                        CCGAATAGCCTCTCCACCCAAGCGGCCGGAGAACCTGCGTGCAATCCAT
                        CTTGTTCAATCATGCGAAACGATCCTCATCCTGTCTCTTGATCAGATCTT
                        GATCCCCTGCGCCATCAGATCCTTGGCGGCAAGAAAGCCATCCAGTTTA
```

-continued

| Sequence Appendix | | |
|---|---|---|
| SEQ ID NO: | Identifier | SEQUENCES |
| | | CTTTGCAGGGCTTCCCAACCTTACCAGAGGGCGCCCCAGCTGGCAATTC CGACGTCTAAGAAACCATTATTATCATGACATTAACCTATAAAAATAGG CGTATCACGAGGCCCTTTCGTCTTCAC |
| 11 | >(3) pTD103- RpaR-RpaI- LAA-sfGFP | TCCTCATCCTGTCTCTTGATCAGATCTTGATCCCCTGCGCCATCAGATCC TTGGCGGCAAGAAAGCCATCCAGTTTACTTTGCAGGGCTTCCCAACCTT ACCAGAGGGCGCCCCAGCTGGCAATTCCGACGTCTAAGAAACCATTATT ATCATGACATTAACCTATAAAAATAGGCGTATCACGAGGCCCTTTCGTC TTCACCTCGAGTCACAAACGGATCAATCCGAGCGTCAATGCCTTGGCAA CCGCCGCGGTGCGGTTGGCGGCGTCGAGCTTGCGGGCGGCTTCGATCAG ATGGAATTTCACCGTGCGTTCGGTGATGCAGAGGATTACCGAGATTTCC CAGGCGGTCTTGCCCTGCGCTGCCCATTGCAGGATCTCGCACTCGCGCG GCGTGAGCCGGTTGCGCCGGATCGGCTTTGGCCGGCTGAGTGCGCGCA GGCGACTATGCGCGTAGATGCTGACCAGCTGCATCGCGCCGCGCGCGG CCGGGCTGAGGTCCGGATCCTTGCCGGCCATGCTGATCGCGGCGCTACC GTCGTCGTAGTGCAGCGGAATGCAGTAACCCTCGACCAGTCCGAATTCC GCCGCCCGGGTCATGACCCGGTGGGCGGCCGGATCACGGTCGCGGTCG TAGGGTGCATCGGACCATACGAAAGGATGAACCGTGGTAGCGCCGTGG CGCGGCACCGGATCGACCGCGCTGAAGTTTTCGCTGACATACAGATCGA ACCAGTCTCGCGGCCAGCCATTGGCCAGCGTCAGCTCCGGTAGTCCGGC ATTGCGCGACGGCAGGCCGGCCATGATGTAGGCGGTAAATCCGCAGCT CGCGATCAGCGATTCGAACCGGCTGATCAGCGCCGGCGCCTCGAGCCG TTCGACGGAATCGACGAATTCCAGCGCACGCCGTCCCCAAAGCTGATCT TCGCCGACGATCATACTATTGTATCGCTGGGAATACAATTACTTAACAT AAGCACCTGTAGGATCGTACAGGTTTACGCAAGAAAATGGTTTGTTATA GTCGAATGAATTCATTAAAGAGGAGAAAGGTACCATGCGTAAAGGCGA AGAGCTGTTCACTGGTGTCGTCCCTATTCTGGTGGAACTGGATGGTGAT GTCAACGGTCATAAGTTTTCCGTGCGTGGCGAGGGTGAAGGTGACGCA ACTAATGGTAAACTGACGCTGAAGTTCATCTGTACTACTGGTAAACTGC CGGTACCTTGGCCGACTCTGGTAACGACGCTGACTTATGGTGTTCAGTG CTTTGCTCGTTATCCGGACCATATGAAGCAGCATGACTTCTTCAAGTCC GCCATGCCGGAAGGCTATGTGCAGGAACGCACGATTTCCTTTAAGGATG ACGGCACGTACAAAACGCGTGCGGAAGTGAAATTTGAAGGCGATACCC TGGTAAACCGCATTGAGCTGAAAGGCATTGACTTTAAAGAAGACGGCA ATATCCTGGGCCATAAGCTGGAATACAATTTTAACAGCCACAATGTTTA CATCACCGCCGATAAACAAAAAAATGGCATTAAAGCGAATTTTAAAAT TCGCCACAACGTGGAGGATGGCAGCGTGCAGCTGGCTGATCACTACCA GCAAAACACTCCAATCGGTGATGGTCCTGTTCTGCTGCCAGACAATCAC TATCTGAGCACGCAAAGCGTTCTGTCTAAAGATCCGAACGAGAAACGC GATCATATGGTTCTGCTGGAGTTCGTAACCGCAGCGGGCATCACGCATG GTATGGATGAACTGTACAAATGAAAGCTTAATTAGCTGATCTAGACGCG TGCTAGAGGCATCAAATAAAACGAAAGGCTCAGTCGAAAGACTGGGCC TTTCGTTTTATCTGTTGTTTGTCGGTGAACGCTCTCCTGAGTAGGACAAA TCCGCCGCCCTAGACCTAGCCGTCTTCACCATGCATTCACAAACGGATC AATCCGAGCGTCAATGCCTTGGCAACCGCCGCGGTGCGGTTGGCGGCGT CGAGCTTGCGGGCGGCTTCGATCAGATGGAATTTCACCGTGCGTTCGGT GATGCAGAGGATTACCGAGATTTCCCAGGCGGTCTTGCCCTGCGCTGCC CATTGCAGGATCTCGCACTCGCGCGGCGTGAGCCGGTTGCGCCGGATCG GCTTTGGCCGGCTGAGTGCGCGCAGGCGACTATGCGCGTAGATGCTGAC CAGCTGCATCGCGCCGCGCGCGGCCGGGCTGAGGTCCGGATCCTTGCCG GCCATGCTGATCGCGGCGCTACCGTCGTCGTAGTGCAGCGGAATGCAGT AACCCTCGACCAGTCCGAATTCCGCCGCCCGGGTCATGACCCGGTGGGC GGCCGGATCACGGTCGCGGTCGTAGGGTGCATCGGACCATACGAAAGG ATGAACCGTGGTAGCGCCGTGGCGCGGCACCGGATCGACCGCGCTGAA GTTTTCGCTGACATACAGATCGAACCAGTCTCGCGGCCAGCCATTGGCC AGCGTCAGCTCCGGTAGTCCGGCATTGCGCGACGGCAGGCCGGCCATG ATGTAGGCGGTAAATCCGCAGCTCGCGATCAGCGATTCGAACCGGCTG ATCAGCGCCGGCGCCTCGAGCCGTTCGACGGAATCGACGAATTCCAGC GCACGCCGTCCCCAAAGCTGATCTTCGCCGACGATCATACTATTGTATC GCTGGGAATACAATTACTTAACATAAGCACCTGTAGGATCGTACAGGTT TACGCAAGAAAATGGTTTGTTATAGTCGAATGAATTCATTAAAGAGGA GAAAGGTACCATGCAGGTTCATGTCATCCGTCGAGAGAACCGCGCGCT CTATGCCGGTCTGCTCGAAAAGTACTTCCGCATCCGTCACCAGATCTAC GTCGTCGAGCGCGGCTGGAAGGAGCTCGATCGGCCGGATGGCCGCGAG ATCGATCAGTTCGACACCGAAGACGCCGTGTATCTGCTCGGCGTCGACA ATGACGACATCGTCGCCGGCATGCGGATGGTGCCGACCACGTCACCGA CGCTCCTCAGCGACGTCTTCCCGCAGCTTGCGCTGGCAGGCCCGGTGCG GCGGCCGGATGCCTACGAGCTGTCGCGGATCTTCGTGGTACCGCGCAAG CGCGGCGAGCATGGCGGCCCGCGCGCCGAAGCCGTGATCCAGGCGGCC GCGATGGAGTACGGCCTGTCGATCGGTCTGTCGGCCTTCACCATCGTGC TGGAGACCTGGTGGCTGCCGCGACTGGTGGACCAGGGCTGGAAGGCAA AGCCGCTCGGCCTGCCTCAGGACATCAACGGATTCTCGACCACCGCAGT GATCGTCGACGTCGACGACGACGCCTGGGTCGGCATCTGCAATCGCCGC |

-continued

| | | Sequence Appendix |
|---|---|---|
| SEQ ID NO: | Identifier | SEQUENCES |

|  |  | TCGGTGCCCGGACCCACGCTGGAATGGCGCGGGCTCGAAGCCATCCGC<br>CGTCATTCGCTTCCGGAATTCCAGGTGATTTCAGCAGCGAACGACGAAA<br>ATTACGCCCTTGCAGCGTAAGTGCTAGAGGCATCAAATAAAACGAAAG<br>GCTCAGTCGAAAGACTGGGCCTTTCGTTTTATCTGTTGTTTGTCGGTGAA<br>CGCTCTCCTGAGTAGGACAAATCCGCCGCCCTAGACCTAGGGCGTTCGG<br>CTGCGGCGAGCGGTATCAGCTCACTCAAAGGCGGTAATACGGTTATCCA<br>CAGAATCAGGGGATAACGCAGGAAAGAACATGTGAGCAAAAGGCCAG<br>CAAAAGGCCAGGAACCGTAAAAAGGCCGCGTTGCTGGCGTTTTTCCAT<br>AGGCTCCGCCCCCCTGACGAGCATCACAAAAATCGACGCTCAAGTCAG<br>AGGTGGCGAAACCCGACAGGACTATAAAGATACCAGGCGTTTCCCCCT<br>GGAAGCTCCCTCGTGCGCTCTCCTGTTCCGACCCTGCCGCTTACCGGAT<br>ACCTGTCCGCCTTTCTCCCTTCGGGAAGCGTGGCGCTTTCTCATAGCTCA<br>CGCTGTAGGTATCTCAGTTCGGTGTAGGTCGTTCGCTCCAAGCTGGGCT<br>GTGTGCACGAACCCCCCGTTCAGCCCGACCGCTGCGCCTTATCCGGTAA<br>CTATCGTCTTGAGTCCAACCCGGTAAGACACGACTTATCGCCACTGGCA<br>GCAGCCACTGGTAACAGGATTAGCAGAGCGAGGTATGTAGGCGGTGCT<br>ACAGAGTTCTTGAAGTGGTGGCCTAACTACGGCTACACTAGAAGGACA<br>GTATTTGGTATCTGCGCTCTGCTGAAGCCAGTTACCTTCGGAAAAAGAG<br>TTGGTAGCTCTTGATCCGGCAAACAAACCACCGCTGGTAGCGGTGGTTT<br>TTTTGTTTGCAAGCAGCAGATTACGCGCAGAAAAAAAGGATCTCAAGA<br>AGATCCTTTGATCTTTTCTACGGGGTCTGACGCTCAGTGGAACGAAAAC<br>TCACGTTAAGGGATTTTGGTCATGACTAGTGCTTGGATTCTCACCAATA<br>AAAAACGCCCGGCGGCAACCGAGCGTTCTGAACAAATCCAGATGGAGT<br>TCTGAGGTCATTACTGGATCTATCAACAGGAGTCCAAGCGAGCTCTCGA<br>ACCCCAGAGTCCCGCTCAGAAGAACTCGTCAAGAAGGCGATAGAAGGC<br>GATGCGCTGCGAATCGGGAGCGGCGATACCGTAAAGCACGAGGAAGCG<br>GTCAGCCCATTCGCCGCCAAGCTCTTCAGCAATATCACGGGTAGCCAAC<br>GCTATGTCCTGATAGCGGTCCGCCACACCCAGCCGGCCACAGTCGATGA<br>ATCCAGAAAAGCGGCCATTTTCCACCATGATATTCGGCAAGCAGGCATC<br>GCCATGGGTCACGACGAGATCCTCGCCGTCGGGCATGCGCGCCTTGAGC<br>CTGGCGAACAGTTCGGCTGGCGCGAGCCCCTGATGCTCTTCGTCCAGAT<br>CATCCTGATCGACAAGACCGGCTTCCATCCGAGTACGTGCTCGCTCGAT<br>GCGATGTTTCGCTTGGTGGTCGAATGGGCAGGTAGCCGGATCAAGCGTA<br>TGCAGCCGCCGCATTGCATCAGCCATGATGGATACTTTCTCGGCAGGAG<br>CAAGGTGAGATGACAGGAGATCCTGCCCCGGCACTTCGCCCAATAGCA<br>GCCAGTCCCTTCCCGCTTCAGTGACAACGTCGAGCACAGCTGCGCAAGG<br>AACGCCCGTCGTGGCCAGCCACGATAGCCGCGCTGCCTCGTCCTGCAGT<br>TCATTCAGGGCACCGGACAGGTCGGTCTTGACAAAAAGAACCGGGCGC<br>CCCTGCGCTGACAGCCGGAACACGGCGGCATCAGAGCAGCCGATTGTC<br>TGTTGTGCCCAGTCATAGCCGAATAGCCTCTCCACCCAAGCGGCCGGAG<br>AACCTGCGTGCAATCCATCTTGTTCAATCATGCGAAACGA |
| 12 | >pZA35\X174\<br>(+Lux | TTAATTTTTAAAGTATGGGCAATCAATTGCTCCTGTTAAAATTGCTTTAG<br>AAATACTTTGGCAGCGGTTTGTTGTATTGAGTTTCATTTGCGCATTGGTT<br>AAATGGAAAGTGACAGTACGCTCACTGCAGCCTAATATTTTTGAAATAT<br>CCCAAGAGCTTTTTCCTTCGCATGCCCACGCTAAACATTCTTTTTCTCTT<br>TTGGTTAAATCGTTGTTTGATTTATTATTTGCTATATTTATTTTTCGATAA<br>TTATCAACTAGAGAAGGAACAATTAATGGTATGTTCATACACGCATGTA<br>AAAATAAACTATCTATATAGTTGTCTTTTTCTGAATGTGCAAAACTAAG<br>CATTCCGAAGCCATTGTTAGCCGTATGAATAGGGAAACTAAACCCAGTG<br>ATAAGACCTGATGTTTTCGCTTCTTTAATTACATTTGGAGATTTTTTATT<br>TACAGCATTGTTTTCAAATATATTCCAATTAATTGGTGAATGATTGGAG<br>TTAGAATAATCTACTATAGGATCATATTTTATTAAATTAGCGTCATCATA<br>ATATTGCCTCCATTTTTTAGGGTAATTATCTAGAATTGAAATATCAGATT<br>TAACCATAGAATGAGGATAAATGATCGCGAGTAAATAATATTCACAAT<br>GTACCATTTTAGTCATATCAGATAAGCATTGATTAATATCATTATTGCTT<br>CTACAAGCTTTAATTTTATTAATTATTCTGTATGTGTCGTCGGCATTTAT<br>GtttttCATACCCATCTCTTTATCCTTACCTATTGTTTGTCGCAAGTTTTG<br>CGTGTTATATATCATTAAAACGGTAATGGATTGACATTTGATTCTAATA<br>AATTGGATTTTTGTCACACTATTGTATCGCTGGGAATACAATTACTTAAC<br>ATAAGCACCTGTAGGATCGTACAGGTTTACGCAAGAAATGGTTTGTTA<br>TAGTCGAATAAACGCAAGGGAGGTTGGTATGGTACGCTGGACTTTGTG<br>GGATACCCTCGCTTTCCTGCTCCTGTTGAGTTTATTGCTGCCGTCATTGC<br>TTATTATGTTCATCCCGTCAACATTCAAACGGCCTGTCTCATCATGGAA<br>GGCGCTGAATTTACGGAAAACATTATTAATGGCGTCGAGCGTCCGGTTA<br>AAGCCGCTGAATTGTTCGCGTTTACCTTGCGTGTACGCGCAGGAAACAC<br>TGACGTTCTTACTGACGCAGAAGAAAACGTGCGTCAAAAATTACGTGC<br>GGAAGGAGTGAACGCGTGCTAGAGGCATCAAATAAAACGAAAGGCTCA<br>GTCGAAAGACTGGGCCTTTCGTTTTATCTGTTGTTTGTCGGTGAACGCTC<br>TCCTGAGTAGGACAAATCCGCCGCCCTAGACCTAGGGGATATATTCCGC<br>TTCCTCGCTCACTGACTCGCTACGCTCGGTCGTTCGACTGCGGCGAGCG<br>GAAATGGCTTACGAACGGGCGGAGATTTCCTGGAAGATGCCAGGAAG<br>ATACTTAACAGGGAAGTGAGAGGGCCGCGGCAAAGCCGTTTTTCCATA |

Sequence Appendix

SEQ
ID
NO: Identifier      SEQUENCES

```
                    GGCTCCGCCCCCCTGACAAGCATCACGAAATCTGACGCTCAAATCAGTG
                    GTGGCGAAACCCGACAGGACTATAAAGATACCAGGCGTTTCCCCCTGG
                    CGGCTCCCTCGTGCGCTCTCCTGTTCCTGCCTTTCGGTTTACCGGTGTCA
                    TTCCGCTGTTATGGCCGCGTTTGTCTCATTCCACGCCTGACACTCAGTTC
                    CGGGTAGGCAGTTCGCTCCAAGCTGGACTGTATGCACGAACCCCCCGTT
                    CAGTCCGACCGCTGCGCCTTATCCGGTAACTATCGTCTTGAGTCCAACC
                    CGGAAAGACATGCAAAAGCACCACTGGCAGCAGCCACTGGTAATTGAT
                    TTAGAGGAGTTAGTCTTGAAGTCATGCGCCGGTTAAGGCTAAACTGAAA
                    GGACAAGTTTTGGTGACTGCGCTCCTCCAAGCCAGTTACCTCGGTTCAA
                    AGAGTTGGTAGCTCAGAGAACCTTCGAAAAACCGCCCTGCAAGGCGGT
                    TTTTTCGTTTTCAGAGCAAGAGATTACGCGCAGACCAAAACGATCTCAA
                    GAAGATCATCTTATTAATCAGATAAAATATTTCTAGATTTCAGTGCAAT
                    TTATCTCTTCAAATGTAGCACCTGAAGTCAGCCCCATACGATATAAGTT
                    GTTACTAGTGCTTGGATTCTCACCAATAAAAAACGCCCGGCGGCAACCG
                    AGCGTTCTGAACAAATCCAGATGGAGTTCTGAGGTCATTACTGGATCTA
                    TCAACAGGAGTCCAAGCGAGCTCGATATCAAATTACGCCCCGCCCTGCC
                    ACTCATCGCAGTACTGTTGTAATTCATTAAGCATTCTGCCGACATGGAA
                    GCCATCACAGACGGCATGATGAACCTGAATCGCCAGCGGCATCAGCAC
                    CTTGTCGCCTTGCGTATAATATTTGCCCATGGTGAAAACGGGGGCGAAG
                    AAGTTGTCCATATTGGCCACGTTTAAATCAAAACTGGTGAAACTCACCC
                    AGGGATTGGCTGAGACGAAAAACATATTCTCAATAAACCCTTTAGGGA
                    AATAGGCCAGGTTTTCACCGTAACACGCCACATCTTGCGAATATATGTG
                    TAGAAACTGCCGGAAATCGTCGTGGTATTCACTCCAGAGCGATGAAAA
                    CGTTTCAGTTTGCTCATGGAAAACGGTGTAACAAGGGTGAACACTATCC
                    CATATCACCAGCTCACCGTCTTTCATTGCCATACGGAATTCCGGATGAG
                    CATTCATCAGGCGGGCAAGAATGTGAATAAAGGCCGGATAAAACTTGT
                    GCTTATTTTTCTTTACGGTCTTTAAAAAGGCCGTAATATCCAGCTGAACG
                    GTCTGGTTATAGGTACATTGAGCAACTGACTGAAATGCCTCAAAATGTT
                    CTTTACGATGCCATTGGGATATATCAACGGTGGTATATCCAGTGATTTTT
                    TTCTCCATTTTAGCTTCCTTAGCTCCTGAAAATCTCGATAACTCAAAAAA
                    TACGCCCGGTAGTGATCTTATTTCATTATGGTGAAAGTTGGAACCTCTT
                    ACGTGCCGATCAACGTCTCATTTTCGCCAGATATCGACGTC
```

What is claimed is:

1. A method of inducing quorum sensing, the method comprising:
   - (a) culturing an *Escherichia coli* bacterial strain, wherein the *Escherichia coli* bacterial strain comprises
     - (i) a first nucleic acid sequence encoding p-coumaric acid-CoA ligase from *Nicotiana tabacum* (4CL2nt), wherein expression of the p-coumaric acid-CoA ligase first activator polypeptide results in production of coumaroyl-CoA, wherein the first nucleic acid sequence is operably linked to a pLux promoter;
     - (ii) a second nucleic acid sequence encoding an RpaI synthase, wherein expression of the RpaI synthase results in production of p-coumaroyl-homoserine lactone from coumaroyl-CoA, wherein the second nucleic acid sequence is operably linked to a pLux promoter;
     - (iii) a third nucleic acid sequence encoding an RpaR transcriptional regulator, wherein expression of the RpaR transcriptional regulator results in activation of a quorum sensing system, wherein the third nucleic acid sequence is operably linked to a pLux promoter; and
     - (iv) a fourth nucleic acid sequence encoding a reporter protein, wherein the second and third nucleic acid sequences together form the quorum sensing system responsive to p-coumaroyl-homoserine lactone the fourth nucleic acid sequence is operably linked to the J23106 constitutive promoter; and
   - (b) contacting the *Escherichia coli* bacterial strain with p-coumaric acid; and
   - (c) converting p-coumaric acid into p-coumaroyl-homoserine lactone via steps (i)-(ii), thereby inducing quorum sensing.

2. The method of claim 1, wherein the quorum sensing system comprises the Rpa quorum sensing components RpaI synthase and RpaR transcriptional regulator obtained from *Rhodopseudomonas palustris*.

3. A bacterial strain produced by the method of claim 1.

4. A set of nucleic acids comprising the nucleic acid sequences of claim 1.

5. A composition comprising the bacterial strain of claim 3.

6. The method of claim 1, wherein the first nucleic acid sequence comprises an amino acid sequence with at least 90% identity to SEQ ID 1.

7. The method of claim 1, wherein the reporter protein is a fluorescent protein selected from the group consisting of green fluorescent protein (GFP), superfolder GFP (sfGFP), or cyan fluorescent protein (CFP).

8. The method of claim 1, wherein the *Escherichia coli* bacterial strain further comprises a fifth nucleic acid sequence encoding a bacteriophage lytic protein capable of forming a lesion in the membrane of a host cell.

9. The method of claim 8, wherein the bacteriophage lytic protein is from bacteriophage ΦX174.

10. The method of claim 8, wherein the fifth nucleic acid sequence encoding the bacteriophage lytic protein is operably linked to a promoter that is transcriptionally regulated by the RpaR transcriptional regulator.

11. The method of claim 10, wherein expression of the bacteriophage lytic protein is sufficient to initiate synchronized lysis of the *Escherichia coli* bacterial strain, resulting in cyclic population death and cargo release.

12. The method of claim 1, wherein the step (b) contacting the *Escherichia coli* bacterial strain with p-coumaric acid comprises maintaining the concentration of p-coumaric acid between about 15 μM to 1 mM.

* * * * *

SEQUENCE LISTING

```
<160> NUMBER OF SEQ ID NOS: 12

<210> SEQ ID NO 1
<211> LENGTH: 1629
<212> TYPE: DNA
<213> ORGANISM: Artificial Sequence
<220> FEATURE:
<223> OTHER INFORMATION: Synthetic gene

<400> SEQUENCE: 1
atggagaaag acacgaagca agttgacatc atttttcgct cgaaactgcc ggacatttac      60
attccgaatc atctgccgct gcatagctac tgcttcgaga acatttctga attttctagc     120
cgtccgtgtc tgattaacgg tgccaataaa cagatctata cgtacgcgga cgtcgagttg     180
aacagccgta aggtcgcagc gggtctgcac aagcaaggca tccagcctaa agataccatc     240
atgattctgt tgccaaattc tccggagttt gtgtttgcgt ttatcggcgc aagctacctg     300
ggtgcgatta gcacgatggc aaatccgctg tttaccccgg ctgaggttgt taaacaagca     360
aaagccagca gcgcgaagat catcgtgacc caagcatgcc acgtcaacaa agttaaggac     420
tatgccttcg aaaatgacgt caagatcatt tgcatcgata gcgcgcctga aggttgtctg     480
catttcagcg ttctgacgca ggctaacgaa cacgatattc cggaagttga gattcagccg     540
gacgatgtgg tggccctgcc gtactccagc ggtaccaccg gcctgccgaa aggcgttatg     600
ctgacccaca agggcctggt gacgagcgtc gcccagcagg tcgatggtga aaacccgaac     660
ctgtacatcc acagcgaaga tgttatgctg tgtgttctgc cactgttcca catctattcc     720
```

```
ctgaacagcg tcctgctgtg cggcctgcgt gtgggcgctg ccattttgat tatgcagaag       780
tttgacattg tcagcttctt ggaactgatc caacgctaca aggtgacgat cggtccgttc       840
gtcccgccga ttgtttttggc cattgcaaaa agcccaatgg tggatgacta tgacctgtcg      900
agcgtgcgta ccgtgatgtc cggtgcagcg ccgctgggca aagagctgga ggataccgtt       960
cgtgcgaagt ttccgaatgc gaaactgggt caaggctacg gtatgactga agcaggtccg      1020
gtgctggcga tgtgcttggc gttcgcgaaa gagccgttcg aaatcaaaag cggtgcgtgc      1080
ggtaccgtgg tgcgtaatgc tgaaatgaaa attgtggatc cgaaaaccgg caacagcctg      1140
ccgcgcaacc agagcggtga gatttgtatt cgcggtgacc agattatgaa gggctacctg      1200
aatgacccgg aggccactgc gcgtacgatc gacaaagagg gttggctgta taccggcgac      1260
atcggttata tcgatgacga cgacgagctg ttcatcgttg atcgcctgaa agagttgatt      1320
aagtacaagg gtttccaagt tgcgcctgcg gaactggagg ctctgctgtt gaatcatccg      1380
aacattagcg atgcagcagt cgttccgatg aaggatgagc aggcgggtga agttccggtc      1440
gcgtttgttg tgcgtagcaa cggcagcacg atcaccgagg atgaggtaaa ggatttcatt      1500
tccaaacaag tcatcttcta taagcgtatc aagcgtgtgt ttttcgtcga tgcaatcccg      1560
aaaagcccgt ccggtaagat cctgcgcaaa gacttgcgtg cgaagctggc ggcaggtctg      1620
ccgaattag                                                                1629

<210> SEQ ID NO 2
<211> LENGTH: 57
<212> TYPE: DNA
<213> ORGANISM: Artificial Sequence
<220> FEATURE:
<223> OTHER INFORMATION: Synthetic promoter

<400> SEQUENCE: 2
ttcagaacgc tcggttgccg ccgggcgttt tttattggtg agaatccaag cactagt          57

<210> SEQ ID NO 3
<211> LENGTH: 59
<212> TYPE: DNA
<213> ORGANISM: Artificial Sequence
<220> FEATURE:
<223> OTHER INFORMATION: Synthetic UTR

<400> SEQUENCE: 3
tttacggcta gctcagtcct aggtatagtg ctagctggat ccaagaagga gatataacc        59

<210> SEQ ID NO 4
<211> LENGTH: 77
<212> TYPE: DNA
<213> ORGANISM: Artificial Sequence
<220> FEATURE:
<223> OTHER INFORMATION: Synthetic terminator

<400> SEQUENCE: 4
gcagcgaacg acgaaaatta cgcccttgca gcgtaacaga taaaaaaaat ccttagcttt        60
cgctaaggat gatttct                                                       77

<210> SEQ ID NO 5
<211> LENGTH: 797
<212> TYPE: DNA
<213> ORGANISM: Artificial Sequence
<220> FEATURE:
<223> OTHER INFORMATION: Synthetic origin
```

-continued

```
<400> SEQUENCE: 5
aacaacttat atcgtatggg gctgacttca ggtgctacat ttgaagagat aaattgcact      60
gaaatctaga aatattttat ctgattaata agatgatctt cttgagatcg ttttggtctg     120
cgcgtaatct cttgctctga aaacgaaaaa accgccttgc agggcggttt ttcgaaggtt     180
ctctgagcta ccaactcttt gaaccgaggt aactggcttg gaggagcgca gtcaccaaaa     240
cttgtccttt cagtttagcc ttaaccggcg catgacttca agactaactc ctctaaatca     300
attaccagtg gctgctgcca gtggtgcttt tgcatgtctt tccgggttgg actcaagacg     360
atagttaccg gataaggcgc agcggtcgga ctgaacgggg ggttcgtgca tacagtccag     420
cttggagcga actgcctacc cggaactgag tgtcaggcgt ggaatgagac aaacgcggcc     480
ataacagcgg aatgacaccg gtaaaccgaa aggcaggaac aggagagcgc acgagggagc     540
cgccaggggg aaacgcctgg tatctttata gtcctgtcgg gtttcgccac cactgatttg     600
agcgtcagat ttcgtgatgc ttgtcagggg ggcggagcct atggaaaaac ggctttgccg     660
cggccctctc acttccctgt taagtatctt cctggcatct tccaggaaat ctccgccccg     720
ttcgtaagcc atttccgctc gccgcagtcg aacgaccgag cgtagcgagt cagtgagcga     780
ggaagcggaa tatatcc                                                    797

<210> SEQ ID NO 6
<211> LENGTH: 121
<212> TYPE: DNA
<213> ORGANISM: Artificial Sequence
<220> FEATURE:
<223> OTHER INFORMATION: Synthetic promoter

<400> SEQUENCE: 6
tttgattcta ataaattgga tttttgtcac actattgtat cgctgggaat acaattactt      60
aacataagca cctgtaggat cgtacaggtt tacgcaagaa aatggtttgt tatagtcgaa     120
t                                                                     121

<210> SEQ ID NO 7
<211> LENGTH: 276
<212> TYPE: DNA
<213> ORGANISM: Artificial Sequence
<220> FEATURE:
<223> OTHER INFORMATION: Synthetic gene

<400> SEQUENCE: 7
atggtacgct ggactttgtg ggataccctc gctttcctgc tcctgttgag tttattgctg      60
ccgtcattgc ttattatgtt catcccgtca acattcaaac ggcctgtctc atcatggaag     120
gcgctgaatt tacggaaaac attattaatg gcgtcgagcg tccggttaaa gccgctgaat     180
tgttcgcgtt taccttgcgt gtacgcgcag gaaacactga cgttcttact gacgcagaag     240
aaaacgtgcg tcaaaaatta cgtgcggaag gagtga                               276

<210> SEQ ID NO 8
<211> LENGTH: 732
<212> TYPE: DNA
<213> ORGANISM: Artificial Sequence
<220> FEATURE:
<223> OTHER INFORMATION: Synthetic gene

<400> SEQUENCE: 8
atgatcgtcg gcgaagatca gctttgggga cggcgtgcgc tggaattcgt cgattccgtc      60
gaacggctcg aggcgccggc gctgatcagc cggttcgaat cgctgatcgc gagctgcgga     120
```

-continued

```
tttaccgcct acatcatggc cggcctgccg tcgcgcaatg ccggactacc ggagctgacg      180
ctggccaatg gctggccgcg agactggttc gatctgtatg tcagcgaaaa cttcagcgcg      240
gtcgatccgg tgccgcgcca cggcgctacc acggttcatc ctttcgtatg gtccgatgca      300
ccctacgacc gcgaccgtga tccggccgcc caccgggtca tgacccgggc ggcggaattc      360
ggactggtcg agggttactg cattccgctg cactacgacg acggtagcgc cgcgatcagc      420
atggccggca aggatccgga cctcagcccg gccgcgcgcg gcgcgatgca gctggtcagc      480
atctacgcgc atagtcgcct gcgcgcactc agccggccaa agccgatccg gcgcaaccgg      540
ctcacgccgc gcgagtgcga gatcctgcaa tgggcagcgc agggcaagac cgcctgggaa      600
atctcggtaa tcctctgcat caccgaacgc acggtgaaat tccatctgat cgaagccgcc      660
cgcaagctcg acgccgccaa ccgcaccgcg gcggttgcca aggcattgac gctcggattg      720
atccgtttgt ga                                                         732
```

<210> SEQ ID NO 9
<211> LENGTH: 795
<212> TYPE: DNA
<213> ORGANISM: Artificial Sequence
<220> FEATURE:
<223> OTHER INFORMATION: Synthetic gene

<400> SEQUENCE: 9

```
gatatctggc gaaaatgaga cgttgatcgg cacgtaagag gttccaactt tcaccataat       60
gaaataagat cactaccggg cgtatttttt gagttatcga gattttcagg agctaaggaa      120
gctaaaatgg agaaaaaaat cactggatat accaccgttg atatatccca atggcatcgt      180
aaagaacatt ttgaggcatt tcagtcagtt gctcaatgta cctataacca gaccgttcag      240
ctggatatta cggccttttt aaagaccgta agaaaaata agcacaagtt ttatccggcc      300
tttattcaca ttcttgcccg cctgatgaat gctcatccgg aattccgtat ggcaatgaaa      360
gacggtgagc tggtgatatg ggatagtgtt caccccttgtt acaccgtttt ccatgagcaa      420
actgaaacgt tttcatcgct ctggagtgaa taccacgacg atttccggca gtttctacac      480
atatattcgc aagatgtggc gtgttacggt gaaaacctgg cctatttccc taaagggttt      540
attgagaata tgtttttcgt ctcagccaat ccctgggtga gtttcaccag ttttgattta      600
aacgtggcca atatggacaa cttcttcgcc cccgttttca ccatgggcaa atattatacg      660
caaggcgaca aggtgctgat gccgctggcg attcaggttc atcatgccgt ctgtgatggc      720
ttccatgtcg gcagaatgct taatgaatta caacagtact gcgatgagtg gcagggcggg      780
gcgtaatttg atatc                                                      795
```

<210> SEQ ID NO 10
<211> LENGTH: 5569
<212> TYPE: DNA
<213> ORGANISM: Artificial Sequence
<220> FEATURE:
<223> OTHER INFORMATION: Synthetic construct

<400> SEQUENCE: 10

```
ctcgagttaa tttttaaagt atgggcaatc aattgctcct gttaaaattg ctttagaaat       60
actttggcag cggtttgttg tattgagttt catttgcgca ttggttaaat ggaaagtgac      120
agtacgctca ctgcagccta atattttttga aatatcccaa gagcttttc cttcgcatgc      180 ccacgctaaa cattctttttt ctcttttggt taaatcgttg tttgatttat tatttgctat      240
```

```
atttatttt  cgataattat  caactagaga  aggaacaatt  aatggtatgt  tcatacacgc  300
atgtaaaaat  aaactatcta  tatagttgtc  tttttctgaa  tgtgcaaaac  taagcattcc  360
gaagccattg  ttagccgtat  gaatagggaa  actaaaccca  gtgataagac  ctgatgtttt  420
cgcttcttta  attacatttg  gagattttt   atttacagca  ttgttttcaa  atatattcca  480
attaattggt  gaatgattgg  agttagaata  atctactata  ggatcatatt  ttattaaatt  540
agcgtcatca  taatattgcc  tccatttttt  agggtaatta  tctagaattg  aaatatcaga  600
tttaaccata  gaatgaggat  aaatgatcgc  gagtaaataa  tattcacaat  gtaccatttt  660
agtcatatca  gataagcatt  gattaatatc  attattgctt  ctacaagctt  taattttatt  720
aattattctg  tatgtgtcgt  cggcatttat  gtttttcata  cccatctctt  tatccttacc  780
tattgtttgt  cgcaagtttt  gcgtgttata  tatcattaaa  acggtaatgg  attgacattt  840
gattctaata  aattggattt  ttgtcacact  attgtatcgc  tgggaataca  attacttaac  900
ataagcacct  gtaggatcgt  acaggtttac  gcaagaaaat  ggtttgttat  agtcgaatga  960
attcattaaa  gaggagaaag  gtaccatgac  tataatgata  aaaaaatcgg  atttttttggc  1020 aattccatcg  gaggagtata  aaggtattct  aagtcttcgt  tatcaagtgt  ttaagcaaag  1080
acttgagtgg  gacttagttg  tagaaaataa  ccttgaatca  gatgagtatg  ataactcaaa  1140
tgcagaatat  atttatgctt  gtgatgatac  tgaaaatgta  agtggatgct  ggcgtttatt  1200
acctacaaca  ggtgattata  tgctgaaaag  tgttttttcct  gaattgcttg  gtcaacagag  1260
tgctcccaaa  gatcctaata  tagtcgaatt  aagtcgtttt  gctgtaggta  aaaatagctc  1320
aaagataaat  aactctgcta  gtgaaattac  aatgaaacta  tttgaagcta  tatataaaca  1380
cgctgttagt  caaggtatta  cagaatatgt  aacagtaaca  tcaacagcaa  tagagcgatt  1440
tttaaagcgt  attaaagttc  cttgtcatcg  tattggagac  aaagaaattc  atgtattagg  1500
tgatactaaa  tcggttgtat  tgtctatgcc  tattaatgaa  cagtttaaaa  aagcagtctt  1560
aaatgcagcg  aacgacgaaa  attacgccct  tgcagcgtaa  acgcgtgcta  gaggcatcaa  1620
ataaaacgaa  aggctcagtc  gaaagactgg  gcctttcgtt  ttatctgttg  tttgtcggtg  1680
aacgctctcc  tgagtaggac  aaatccgccg  ccctagacct  aggcgtcttc  acctcgagtt  1740 aattttttaaa  gtatgggcaa  tcaattgctc  ctgttaaaat  tgctttagaa  atactttggc  1800
agcggtttgt  tgtattgagt  ttcatttgcg  cattggttaa  atggaaagtg  acagtacgct  1860
cactgcagcc  taatattttt  gaaatatccc  aagagctttt  tccttcgcat  gcccacgcta  1920
aacattcttt  ttctcttttg  gttaaatcgt  tgtttgattt  attatttgct  atatttattt  1980
ttcgataatt  atcaactaga  gaaggaacaa  ttaatggtat  gttcatacac  gcatgtaaaa  2040
ataaactatc  tatatagttg  tcttttttctg  aatgtgcaaa  actaagcatt  ccgaagccat  2100
tgttagccgt  atgaataggg  aaactaaacc  cagtgataag  acctgatgtt  ttcgcttctt  2160
taattacatt  tggagatttt  ttatttacag  cattgttttc  aaatatattc  caattaattg  2220
gtgaatgatt  ggagttagaa  taatctacta  taggatcata  ttttattaaa  ttagcgtcat  2280
cataatattg  cctccatttt  ttagggtaat  tatctagaat  tgaaatatca  gatttaacca  2340
tagaatgagg  ataaatgatc  gcgagtaaat  aatattcaca  atgtaccatt  ttagtcatat  2400
cagataagca  ttgattaata  tcattattgc  ttctacaagc  tttaatttta  ttaattattc  2460
tgtatgtgtc  gtcggcattt  atgttttttca  tacccatctc  tttatcctta  cctattgttt  2520
gtcgcaagtt  ttgcgtgtta  tatatcatta  aaacggtaat  ggattgacat  ttgattctaa  2580
taaattggat  ttttgtcaca  ctattgtatc  gctgggaata  caattactta  acataagcac  2640
```

```
ctgtaggatc gtacaggttt acgcaagaaa atggtttgtt atagtcgaat gaattcatta   2700
aagaggagaa aggtaccatg tctaaaggtg aagaattatt cactggtgtt gtcccaattt   2760
tggttgaatt agatggtgat gttaatggtc acaaattttc tgtctccggt gaaggtgaag   2820
gtgatgctac ttacggtaaa ttgaccttaa aatttatttg tactactggt aaaattgccag  2880 ttccatggcc aaccttagtc actactttaa cttggggtgt tcaatgtttt gctagatacc   2940
cagatcatat gaaacaacat gactttttca agtctgccat gccagaaggt tatgttcaag   3000
aaagaactat ttttttcaaa gatgacggta actacaagac cagagctgaa gtcaagtttg   3060
aaggtgatac cttagttaat agaatcgaat taaaaggtat tgattttaaa gaagatggta   3120
acattttagg tcacaaattg gaatacaacg ctatttctga taatgtttac atcactgctg   3180
acaaacaaaa gaatggtatc aaagctaact tcaaaattag acacaacatt gaagatggtg   3240
gtgttcaatt agctgaccat tatcaacaaa atactccaat tggtgatggt ccagtcttgt   3300
taccagacaa ccattactta tccactcaat ctaaattatc caaagatcca aacgaaaaga   3360
gagaccacat ggtcttgtta gaatttgtta ctgctgctgg tattacccat ggtatggatg   3420
aattgtacaa aactagtgca gcgaacgacg aaaaattacgc ccttgcagcg tgaaagctta  3480
attagctgat ctagacgcgt gctagaggca tcaaataaaa cgaaaggctc agtcgaaaga   3540
ctgggccttt cgttttatct gttgtttgtc ggtgaacgct ctcctgagta ggacaaatcc   3600
gccgccctag acctagggcg ttcggctgcg gcgagcggta tcagctcact caaaggcggt   3660
aatacggtta tccacagaat caggggataa cgcaggaaag aacatgtgag caaaaggcca   3720
gcaaaaggcc aggaaccgta aaaaggccgc gttgctggcg tttttccata ggctccgccc   3780
ccctgacgag catcacaaaa atcgacgctc aagtcagagg tggcgaaacc cgacaggact   3840
ataaagatac caggcgtttc cccctggaag ctccctcgtg cgctctcctg ttccgaccct   3900
gccgcttacc ggatacctgt ccgcctttct cccttcggga agcgtggcgc tttctcatag   3960
ctcacgctgt aggtatctca gttcggtgta ggtcgttcgc tccaagctgg gctgtgtgca   4020
cgaacccccc gttcagcccg accgctgcgc cttatccggt aactatcgtc ttgagtccaa   4080
cccggtaaga cacgacttat cgccactggc agcagccact ggtaacagga ttagcagagc   4140
gaggtatgta ggcggtgcta cagagttctt gaagtggtgg cctaactacg gctacactag   4200
aaggacagta tttggtatct gcgctctgct gaagccagtt accttcggaa aaagagttgg   4260
tagctcttga tccggcaaac aaaccaccgc tggtagcggt ggtttttttg tttgcaagca   4320
gcagattacg cgcagaaaaa aaggatctca agaagatcct ttgatctttt ctacggggtc   4380
tgacgctcag tggaacgaaa actcacgtta agggattttg gtcatgacta gtgcttggat   4440
tctcaccaat aaaaaacgcc cggcggcaac cgagcgttct gaacaaatcc agatggagtt   4500
ctgaggtcat tactggatct atcaacagga gtccaagcga gctctcgaac cccagagtcc   4560
cgctcagaag aactcgtcaa gaaggcgata gaaggcgatg cgctgcgaat cgggagcggc   4620
gataccgtaa agcacgagga agcggtcagc ccattcgccg ccaagctctt cagcaatatc   4680
acgggtagcc aacgctatgt cctgatagcg gtccgccaca cccagccggc cacagtcgat   4740
gaatccagaa aagcggccat tttccaccat gatattcggc aagcaggcat cgccatgggt   4800
cacgacgaga tcctcgccgt cgggcatgcg cgccttgagc ctggcgaaca gttcggctgg   4860
cgcgagcccc tgatgctctt cgtccagatc atcctgatcg acaagaccgg cttccatccg   4920
agtacgtgct cgctcgatgc gatgtttcgc ttggtggtcg aatgggcagg tagccggatc   4980
```

-continued

```
aagcgtatgc agccgccgca ttgcatcagc catgatggat actttctcgg caggagcaag    5040
gtgagatgac aggagatcct gccccggcac ttcgcccaat agcagccagt cccttcccgc    5100
ttcagtgaca acgtcgagca cagctgcgca aggaacgccc gtcgtggcca gccacgatag    5160
ccgcgctgcc tcgtcctgca gttcattcag ggcaccggac aggtcggtct tgacaaaaag    5220
aaccgggcgc ccctgcgctg acagccggaa cacggcggca tcagagcagc cgattgtctg    5280
ttgtgcccag tcatagccga atagcctctc cacccaagcg gccggagaac ctgcgtgcaa    5340
tccatcttgt tcaatcatgc gaaacgatcc tcatcctgtc tcttgatcag atcttgatcc    5400
cctgcgccat cagatccttg gcggcaagaa agccatccag tttactttgc agggcttccc    5460
aaccttacca gagggcgccc cagctggcaa ttccgacgtc taagaaacca ttattatcat    5520
gacattaacc tataaaaata ggcgtatcac gaggcccttt cgtcttcac               5569
```

<210> SEQ ID NO 11
<211> LENGTH: 5344
<212> TYPE: DNA
<213> ORGANISM: Artificial Sequence
<220> FEATURE:
<223> OTHER INFORMATION: Synthetic construct

<400> SEQUENCE: 11

```
tcctcatcct gtctcttgat cagatcttga tcccctgcgc catcagatcc ttggcggcaa      60
gaaagccatc cagtttactt tgcagggctt cccaacctta ccagagggcg ccccagctgg     120
caattccgac gtctaagaaa ccattattat catgacatta acctataaaa ataggcgtat     180
cacgaggccc tttcgtcttc acctcgagtc acaaacggat caatccgagc gtcaatgcct     240
tggcaaccgc cgcggtgcgg ttggcggcgt cgagcttgcg ggcggcttcg atcagatgga     300
atttcaccgt gcgttcggtg atgcagagga ttaccgagat ttcccaggcg gtcttgccct     360
gcgctgccca ttgcaggatc tcgcactcgc gcggcgtgag ccggttgcgc cggatcggct     420
ttggccggct gagtgcgcgc aggcgactat gcgcgtagat gctgaccagc tgcatcgcgc     480
cgcgcgcggc cgggctgagg tccggatcct tgccggccat gctgatcgcg cgctaccgt     540 cgtcgtagtg cagcggaatg cagtaaccct cgaccagtcc gaattccgcc gcccgggtca     600
tgacccggtg ggcggccgga tcacggtcgc ggtcgtaggg tgcatcggac catacgaaag     660
gatgaaccgt ggtagcgccg tggcgcggca ccggatcgac cgcgctgaag ttttcgctga     720
catacagatc gaaccagtct cgcggccagc cattggccag cgtcagctcc ggtagtccgg     780
cattgcgcga cggcaggccg gccatgatgt aggcggtaaa tccgcagctc gcgatcagcg     840
attcgaaccg gctgatcagc gccggcgcct cgagccgttc gacggaatcg acgaattcca     900
gcgcacgccg tccccaaagc tgatcttcgc gacgatcat actattgtat cgctgggaat     960
acaattactt aacataagca cctgtaggat cgtacaggtt tacgcaagaa aatggtttgt    1020
tatagtcgaa tgaattcatt aaagaggaga aaggtaccat gcgtaaaggc gaagagctgt    1080
tcactggtgt cgtccctatt ctggtggaac tggatgtgta tgtcaacggt cataagtttt    1140
ccgtgcgtgg cgagggtgaa ggtgacgcaa ctaatggtaa actgacgctg aagttcatct    1200
gtactactgg taaactgccg gtaccttggc cgactctggt aacgacgctg acttatggtg    1260
ttcagtgctt tgctcgttat ccggaccata tgaagcagca tgacttcttc aagtccgcca    1320
tgccggaagg ctatgtgcag gaacgcacga tttcctttaa ggatgacggc acgtacaaaa    1380
cgcgtgcgga agtgaaattt gaaggcgata ccctggtaaa ccgcattgag ctgaaaggca    1440
ttgactttaa agaagacggc aatatcctgg gccataagct ggaatacaat tttaacagcc    1500
```

-continued

```
acaatgttta catcaccgcc gataaacaaa aaaatggcat taaagcgaat tttaaaattc   1560
gccacaacgt ggaggatggc agcgtgcagc tggctgatca ctaccagcaa aacactccaa   1620
tcggtgatgg tcctgttctg ctgccagaca atcactatct gagcacgcaa agcgttctgt   1680
ctaaagatcc gaacgagaaa cgcgatcata tggttctgct ggagttcgta accgcagcgg   1740
gcatcacgca tggtatggat gaactgtaca aatgaaagct taattagctg atctagacgc   1800
gtgctagagg catcaaataa aacgaaaggc tcagtcgaaa gactgggcct ttcgttttat   1860
ctgttgtttg tcggtgaacg ctctcctgag taggacaaat ccgccgccct agacctagcc   1920
gtcttcacca tgcattcaca aacggatcaa tccgagcgtc aatgccttgg caaccgccgc   1980
ggtgcggttg gcggcgtcga gcttgcgggc ggcttcgatc agatggaatt tcaccgtgcg   2040
ttcggtgatg cagaggatta ccgagatttc ccaggcggtc ttgccctgcg ctgcccattg   2100
caggatctcg cactcgcgcg gcgtgagccg gttgcgccgg atcggctttg gccggctgag   2160
tgcgcgcagg cgactatgcg cgtagatgct gaccagctgc atcgcgccgc gcgcggccgg   2220
gctgaggtcc ggatccttgc cggccatgct gatcgcggcg ctaccgtcgt cgtagtgcag   2280
cggaatgcag taaccctcga ccagtccgaa ttccgccgcc cgggtcatga cccggtgggc   2340
ggccggatca cggtcgcggt cgtagggtgc atcggaccat acgaaaggat gaaccgtggt   2400
agcgccgtgg cgcggcaccg gatcgaccgc gctgaagttt tcgctgacat acagatcgaa   2460
ccagtctcgc ggccagccat tggccagcgt cagctccggt agtccggcat tgcgcgacgg   2520
caggccggcc atgatgtagg cggtaaatcc gcagctcgcg atcagcgatt cgaaccggct   2580
gatcagcgcc ggcgcctcga gccgttcgac ggaatcgacg aattccagcg cacgccgtcc   2640
ccaaagctga tcttcgccga cgatcatact attgtatcgc tgggaataca attacttaac   2700
ataagcacct gtaggatcgt acaggtttac gcaagaaaat ggtttgttat agtcgaatga   2760
attcattaaa gaggagaaag gtaccatgca ggttcatgtc atccgtcgag agaaccgcgc   2820
gctctatgcc ggtctgctcg aaaagtactt ccgcatccgt caccagatct acgtcgtcga   2880
gcgcggctgg aaggagctcg atcggccgga tggccgcgag atcgatcagt cgacaccga   2940 agacgccgtg tatctgctcg gcgtcgacaa tgacgacatc gtcgccggca tgcggatggt   3000
gccgaccacg tcaccgacgc tcctcagcga cgtcttcccg cagcttgcgc tggcaggccc   3060
ggtgcggcgg ccggatgcct acgagctgtc gcggatcttc gtggtaccgc gcaagcgcgg   3120
cgagcatggc ggcccgcgcg ccgaagccgt gatccaggcg gccgcgatgg agtacggcct   3180
gtcgatcggt ctgtcggcct tcaccatcgt gctggagacc tggtggctgc cgcgactggt   3240
ggaccagggc tggaaggcaa agccgctcgg cctgcctcag gacatcaacg gattctcgac   3300
caccgcagtg atcgtcgacg tcgacgacga cgcctgggtc ggcatctgca atcgccgctc   3360
ggtgcccgga cccacgctgg aatggcgcgg gctcgaagcc atccgccgtc attcgcttcc   3420
ggaattccag gtgatttcag cagcgaacga cgaaaattac gcccttgcag cgtaagtgct   3480
agaggcatca aataaaacga aaggctcagt cgaaagactg ggcctttcgt tttatctgtt   3540
gtttgtcggt gaacgctctc ctgagtagga caaatccgcc gccctagacc tagggcgttc   3600
ggctgcggcg agcggtatca gctcactcaa aggcggtaat acggttatcc acagaatcag   3660
gggataacgc aggaaagaac atgtgagcaa aaggccagca aaaggccagg aaccgtaaaa   3720
aggccgcgtt gctggcgttt ttccataggc tccgcccccc tgacgagcat cacaaaaatc   3780
gacgctcaag tcagaggtgg cgaaacccga caggactata aagataccag gcgtttcccc   3840
```

```
ctggaagctc cctcgtgcgc tctcctgttc cgaccctgcc gcttaccgga tacctgtccg     3900
cctttctccc ttcgggaagc gtggcgcttt ctcatagctc acgctgtagg tatctcagtt     3960
cggtgtaggt cgttcgctcc aagctgggct gtgtgcacga accccccgtt cagcccgacc     4020
gctgcgcctt atccggtaac tatcgtcttg agtccaaccc ggtaagacac gacttatcgc     4080
cactggcagc agccactggt aacaggatta gcagagcgag gtatgtaggc ggtgctacag     4140
agttcttgaa gtggtggcct aactacggct acactagaag gacagtattt ggtatctgcg     4200
ctctgctgaa gccagttacc ttcggaaaaa gagttggtag ctcttgatcc ggcaaacaaa     4260
ccaccgctgg tagcggtggt ttttttgttt gcaagcagca gattacgcgc agaaaaaaag     4320
gatctcaaga agatcctttg atcttttcta cggggtctga cgctcagtgg aacgaaaact     4380
cacgttaagg gattttggtc atgactagtg cttggattct caccaataaa aaacgcccgg     4440
cggcaaccga gcgttctgaa caaatccaga tggagttctg aggtcattac tggatctatc     4500
aacaggagtc caagcgagct ctcgaacccc agagtcccgc tcagaagaac tcgtcaagaa     4560
ggcgatagaa ggcgatgcgc tgcgaatcgg gagcggcgat accgtaaagc acgaggaagc     4620
ggtcagccca ttcgccgcca agctcttcag caatatcacg ggtagccaac gctatgtcct     4680
gatagcggtc cgccacaccc agccggccac agtcgatgaa tccagaaaag cggccatttt     4740
ccaccatgat attcggcaag caggcatcgc catgggtcac gacgagatcc tcgccgtcgg     4800
gcatgcgcgc cttgagcctg gcgaacagtt cggctggcgc gagcccctga tgctcttcgt     4860
ccagatcatc ctgatcgaca agaccggctt ccatccgagt acgtgctcgc tcgatgcgat     4920
gtttcgcttg gtggtcgaat gggcaggtag ccggatcaag cgtatgcagc cgccgcattg     4980
catcagccat gatggatact ttctcggcag gagcaaggtg agatgacagg agatcctgcc     5040
ccggcacttc gcccaatagc agccagtccc ttcccgcttc agtgacaacg tcgagcacag     5100
ctgcgcaagg aacgcccgtc gtggccagcc acgatagccg cgctgcctcg tcctgcagtt     5160
cattcagggc accggacagg tcggtcttga caaaaagaac cgggcgcccc tgcgctgaca     5220
gccggaacac ggcggcatca gagcagccga ttgtctgttg tgcccagtca tagccgaata     5280
gcctctccac ccaagcggcc ggagaacctg cgtgcaatcc atcttgttca atcatgcgaa     5340
acga                                                                  5344
```

<210> SEQ ID NO 12
<211> LENGTH: 3086
<212> TYPE: DNA
<213> ORGANISM: Artificial Sequence
<220> FEATURE:
<223> OTHER INFORMATION: Synthetic construct

<400> SEQUENCE: 12

```
ttaattttta aagtatgggc aatcaattgc tcctgttaaa attgctttag aaatactttg       60
gcagcggttt gttgtattga gtttcatttg cgcattggtt aaatggaaag tgacagtacg      120
ctcactgcag cctaatattt ttgaaatatc ccaagagctt tttccttcgc atgcccacgc      180
taaacattct ttttctcttt tggttaaatc gttgtttgat ttattatttg ctatatttat      240
ttttcgataa ttatcaacta gagaaggaac aattaatggt atgttcatac acgcatgtaa      300
aaataaacta tctatatagt tgtctttttc tgaatgtgca aaactaagca ttccgaagcc      360
attgttagcc gtatgaatag ggaaactaaa cccagtgata agacctgatg tttttcgcttc     420 tttaattaca tttggagatt ttttatttac agcattgttt tcaaatatat tccaattaat      480
tggtgaatga ttggagttag aataatctac ataggatca tattttatta aattagcgtc       540
```

-continued

```
atcataatat tgcctccatt ttttagggta attatctaga attgaaatat cagatttaac    600
catagaatga ggataaatga tcgcgagtaa ataatattca caatgtacca ttttagtcat    660
atcagataag cattgattaa tatcattatt gcttctacaa gctttaattt tattaattat    720
tctgtatgtg tcgtcggcat ttatgttttt catacccatc tctttatcct tacctattgt    780
ttgtcgcaag ttttgcgtgt tatatatcat taaaacggta atggattgac atttgattct    840
aataaattgg atttttgtca cactattgta tcgctgggaa tacaattact taacataagc    900
acctgtagga tcgtacaggt ttacgcaaga aaatggtttg ttatagtcga ataaacgcaa    960
gggaggttgg tatggtacgc tggactttgt gggataccct cgctttcctg ctcctgttga   1020
gtttattgct gccgtcattg cttattatgt tcatcccgtc aacattcaaa cggcctgtct   1080
catcatggaa ggcgctgaat ttacggaaaa cattattaat ggcgtcgagc gtccggttaa   1140
agccgctgaa ttgttcgcgt ttaccttgcg tgtacgcgca ggaaacactg acgttcttac   1200
tgacgcagaa gaaacgtgc gtcaaaaatt acgtgcggaa ggagtgaacg cgtgctagag   1260
gcatcaaata aaacgaaagg ctcagtcgaa agactgggcc tttcgtttta tctgttgttt   1320
gtcggtgaac gctctcctga gtaggacaaa tccgccgccc tagacctagg ggatatattc   1380
cgcttcctcg ctcactgact cgctacgctc ggtcgttcga ctgcggcgag cggaaatggc   1440
ttacgaacgg ggcggagatt tcctggaaga tgccaggaag atacttaaca gggaagtgag   1500
agggccgcgg caaagccgtt tttccatagg ctccgccccc ctgacaagca tcacgaaatc   1560
tgacgctcaa atcagtggtg gcgaaacccg acaggactat aaagatacca ggcgtttccc   1620
cctggcggct ccctcgtgcg ctctcctgtt cctgcctttc ggtttaccgg tgtcattccg   1680
ctgttatggc cgcgtttgtc tcattccacg cctgacactc agttccgggt aggcagttcg   1740
ctccaagctg gactgtatgc acgaacccc cgttcagtcc gaccgctgcg ccttatccgg   1800
taactatcgt cttgagtcca acccggaaag acatgcaaaa gcaccactgg cagcagccac   1860
tggtaattga tttagaggag ttagtcttga agtcatgcgc cggttaaggc taaactgaaa   1920
ggacaagttt tggtgactgc gctcctccaa gccagttacc tcggttcaaa gagttggtag   1980
ctcagagaac cttcgaaaaa ccgccctgca aggcggtttt ttcgtttcca gagcaagaga   2040
ttacgcgcag accaaaacga tctcaagaag atcatcttat taatcagata aaatatttct   2100
agatttcagt gcaatttatc tcttcaaatg tagcacctga agtcagcccc atacgatata   2160
agttgttact agtgcttgga ttctcaccaa taaaaaacgc ccggcggcaa ccgagcgttc   2220
tgaacaaatc cagatggagt tctgaggtca ttactggatc tatcaacagg agtccaagcg   2280
agctcgatat caaattacgc cccgccctgc cactcatcgc agtactgttg taattcatta   2340
agcattctgc cgacatggaa gccatcacag acggcatgat gaacctgaat cgccagcggc   2400
atcagcacct gtcgccttg cgtataatat ttgcccatgg tgaaaacggg ggcgaagaag   2460
ttgtccatat tggccacgtt aaatcaaaa ctggtgaaac tcacccaggg attggctgag   2520
acgaaaaaca tattctcaat aaaccctta gggaaatagg ccaggttttc accgtaacac   2580
gccacatctt gcgaatatat gtgtagaaac tgccggaaat cgtcgtggta ttcactccag   2640
agcgatgaaa acgtttcagt ttgctcatgg aaaacggtgt aacaagggtg aacactatcc   2700
catatcacca gctcaccgtc tttcattgcc atacggaatt ccggatgagc attcatcagg   2760
cgggcaagaa tgtgaataaa ggccggataa aacttgtgct tatttttctt tacggtcttt   2820
aaaaaggccg taatatccag ctgaacggtc tggttatagg tacattgagc aactgactga   2880
```

-continued

```
aatgcctcaa aatgttcttt acgatgccat tgggatatat caacggtggt atatccagtg    2940 attttttct ccattttagc ttccttagct cctgaaaatc tcgataactc aaaaaatacg     3000
cccggtagtg atcttatttc attatggtga aagttggaac ctcttacgtg ccgatcaacg    3060
tctcattttc gccagatatc gacgtc                                         3086
```